US012365877B2

(12) United States Patent
Retting et al.

(10) Patent No.: US 12,365,877 B2
(45) Date of Patent: Jul. 22, 2025

(54) ENGINEERED INTESTINAL TISSUE AND USES THEREOF

(71) Applicant: Organovo, Inc., San Diego, CA (US)

(72) Inventors: Kelsey Nicole Retting, San Diego, CA (US); Deborah Lynn Greene Nguyen, San Diego, CA (US); Lauran Madden, San Diego, CA (US)

(73) Assignee: Organovo, Inc., San Diego, CA (US)

( * ) Notice: Subject to any disclaimer, the term of this patent is extended or adjusted under 35 U.S.C. 154(b) by 173 days.

(21) Appl. No.: 17/695,538

(22) Filed: Mar. 15, 2022

(65) Prior Publication Data

US 2022/0204941 A1    Jun. 30, 2022

Related U.S. Application Data

(62) Division of application No. 16/349,109, filed as application No. PCT/US2017/061016 on Nov. 10, 2017, now Pat. No. 11,655,456.

(60) Provisional application No. 62/420,024, filed on Nov. 10, 2016.

(51) Int. Cl.
| | | |
|---|---|---|
| *C12N 5/071* | (2010.01) | |
| *A61K 35/15* | (2015.01) | |
| *A61K 35/38* | (2015.01) | |
| *C12N 5/078* | (2010.01) | |
| *G01N 33/50* | (2006.01) | |

(52) U.S. Cl.
CPC ............ *C12N 5/0679* (2013.01); *A61K 35/15* (2013.01); *A61K 35/38* (2013.01); *C12N 5/0634* (2013.01); *C12N 5/0697* (2013.01); *G01N 33/5088* (2013.01); *C12N 2502/1335* (2013.01); *C12N 2502/23* (2013.01); *C12N 2513/00* (2013.01); *C12N 2533/30* (2013.01); *C12N 2533/54* (2013.01); *C12N 2535/00* (2013.01)

(58) Field of Classification Search
CPC .......... C12N 5/0679; C12N 2502/1335; C12N 2502/23; C12N 2513/00; G01N 33/5088
See application file for complete search history.

(56) References Cited

U.S. PATENT DOCUMENTS

| | | |
|---|---|---|
| 6,663,821 B2 | 12/2003 | Seward |
| 7,051,654 B2 | 5/2006 | Boland et al. |
| 8,143,055 B2 | 3/2012 | Forgacs et al. |
| 8,728,807 B2 | 5/2014 | Forgacs et al. |
| 8,931,880 B2 | 1/2015 | Murphy et al. |
| 9,149,952 B2 | 10/2015 | Murphy et al. |
| 9,227,339 B2 | 1/2016 | Murphy et al. |
| 9,315,043 B2 | 4/2016 | Murphy et al. |
| 9,499,779 B2 | 11/2016 | Murphy et al. |
| 9,855,369 B2 | 1/2018 | Murphy et al. |
| 10,174,276 B2 | 1/2019 | Murphy et al. |
| 10,967,560 B2 | 4/2021 | Murphy et al. |
| 11,655,456 B2 | 5/2023 | Retting et al. |
| 2004/0023907 A1 | 2/2004 | Dieterich et al. |
| 2013/0164339 A1 | 6/2013 | Murphy et al. |
| 2013/0190210 A1 | 7/2013 | Murphy et al. |
| 2014/0038279 A1* | 2/2014 | Ingber .................... C12N 5/068 435/297.2 |
| 2015/0004273 A1 | 1/2015 | Forgacs et al. |
| 2015/0037445 A1 | 2/2015 | Murphy et al. |
| 2015/0093932 A1 | 4/2015 | Ning et al. |
| 2015/0282885 A1 | 10/2015 | King et al. |
| 2016/0040132 A1 | 2/2016 | Sears et al. |
| 2016/0097039 A1 | 4/2016 | Nguyen et al. |
| 2016/0122723 A1 | 5/2016 | Retting et al. |
| 2017/0130192 A1 | 5/2017 | Retting et al. |
| 2017/0199507 A1 | 7/2017 | Murphy et al. |
| 2018/0265839 A1 | 9/2018 | Retting et al. |
| 2018/0313822 A1 | 11/2018 | Murphy et al. |
| 2020/0197152 A1 | 6/2020 | Murphy et al. |
| 2021/0008788 A1 | 1/2021 | Murphy et al. |
| 2021/0123906 A1 | 4/2021 | Murphy et al. |
| 2021/0291432 A1 | 9/2021 | Murphy et al. |
| 2022/0009156 A1 | 1/2022 | Murphy et al. |
| 2022/0009157 A1 | 1/2022 | Murphy et al. |
| 2022/0009158 A1 | 1/2022 | Murphy et al. |
| 2022/0195380 A1 | 6/2022 | Retting et al. |
| 2022/0204942 A1 | 6/2022 | Retting et al. |

FOREIGN PATENT DOCUMENTS

| | | |
|---|---|---|
| CN | 103255097 A | 8/2013 |
| JP | 2004500855 A | 1/2004 |
| JP | 2014531204 A | 11/2014 |

(Continued)

OTHER PUBLICATIONS

Mills et al., (2016) Physiologically relevant human tissue models for infectious diseases. Drug Discovery Today, 21(9), 1540-1552 (Year: 2016).*
Chen et al., (2015) Robust bioengineered 3D functional human intestinal epithelium. Scientific Reports, 5: 13708 (Year: 2015).*
Abbasi, K., et al., "A Novel Rho-like Protein TbRHP Is Involved in Spindle Formation and Mitosis in Trypanosomes," PLOS One 6(11):e26890, Public Library of Science, United States (2011).
Akbari, P., et al., "Galacto-oligosaccharides Protect the Intestinal Barrier by Maintaining the Tight Junction Network and Modulating the Inflammatory Responses After a Challenge With the Mycotoxin Deoxynivalenol in Human Caco-2 Cell Monolayers and B6C3F1 Mice," The Journal of Nutrition 145(7):1604-1613, American Society for Nutrition, United States (Jul. 2015).
Alqahtani, S., et al., "Experimental Models for Predicting Drug Absorption and Metabolism," Expert Opinion on Drug Metabolism & Toxicology 9(10):1241-1254, Informa Healthcare, England (Oct. 2013).

(Continued)

*Primary Examiner* — Kara D Johnson
(74) *Attorney, Agent, or Firm* — Sterne, Kessler, Goldstein & Fox P.L.L.C.

(57) ABSTRACT

Disclosed are methods of assessing the ability of a candidate therapeutic agent to reverse, reduce or prevent intestinal injury by a potential toxic agent using a three-dimensional, engineered, bioprinted, biological intestinal tissue model. Also disclosed are methods of assessing the effect of an agent on intestinal function, the method comprising contacting the agent with a three-dimensional, engineered, bioprinted, biological intestinal tissue model.

22 Claims, 50 Drawing Sheets

(56) References Cited

FOREIGN PATENT DOCUMENTS

| WO | WO-03018752 A2 | 3/2003 | |
|---|---|---|---|
| WO | WO-2005081970 A2 | 9/2005 | |
| WO | WO-2009030482 A1 * | 3/2009 | ......... G01N 33/5029 |
| WO | WO-2010008905 A2 | 1/2010 | |
| WO | WO-2012054195 A2 | 4/2012 | |
| WO | WO-2013040087 A2 | 3/2013 | |
| WO | WO-2013158508 A1 | 10/2013 | |
| WO | WO-2015017579 A1 | 2/2015 | |
| WO | WO-2016057571 A1 | 4/2016 | |
| WO | WO-2016073782 A1 | 5/2016 | |
| WO | WO-2017083402 A1 | 5/2017 | |
| WO | WO-2020229982 A1 | 11/2020 | |

OTHER PUBLICATIONS

Andrade, M.C., et al., "Cell Surface Markers for T and B Lymphocytes Activation and Adhesion as Putative Prognostic Biomarkers for Head and Neck Squamous Cell Carcinoma," Human Immunology 74(12): 1563-1574, Elsevier/North-Holland, United States (Dec. 2013).

Angel, C.E., et al., "Distinctive Localization of Antigen-presenting Cells in Human Lymph Nodes," Blood 113(6):1257-1267, Elsevier, United States (Feb. 2009).

Aprile, G., et al., "Treatment-related Gastrointestinal Toxicities and Advanced Colorectal or Pancreatic Cancer: A Critical Update," World Journal of Gastroenterology 21(41):11793-11803, Baishideng Publishing Group, United States (Nov. 2015).

Beebe, D., et al., "Functional Hydrogel Structures for Autonomous Flow Control Inside Microfluidic Channels," Nature 404(6778):588-590, Nature Publishing Group, England (Apr. 2000).

Bentz, J., et al., "Variability in P-glycoprotein Inhibitory Potency ($IC_{50}$ Using Various in Vitro Experimental Systems: Implications for Universal Digoxin Drug-drug Interaction Risk Assessment Decision Criteria," Drug Metabolism and Disposition: The Biological Fate of Chemicals 41(7):1347-1366, American Society for Pharmacology and Experimental Therapeutics, United States (Jul. 2013).

Boelsterli, U.A., et al., "Multiple NSAID-induced Hits Injure the Small Intestine: Underlying Mechanisms and Novel Strategies," Toxicological Sciences 131(2):654-667, Oxford University Press, United States (Feb. 2013).

Chang, S.K., et al., "Localization of Mucin (MUC2 and MUC3) Messenger RNA and Peptide Expression in Human Normal Intestine and Colon Cancer," Gastroenterology 107(1):28-36, W.B. Saunders, United States (Jul. 1994).

Chantret, I., et al., "Epithelial Polarity, Villin Expression, and Enterocytic Differentiation of Cultured Human Colon Carcinoma Cells: a Survey of Twenty Cell Lines," Cancer research 48(7):1936-1942, American Association for Cancer Research, United States (Apr. 1988).

Chen, Y., et al., "Robust bioengineered functional human intestinal epithelium," Scientific Reports 5:13708, Springer Nature Limited, United Kingdom (2015).

Chia, H.N. and Wu, B.M., "Recent Advances in 3D Printing of Biomaterials," Journal of Biological Engineering 9:4, BioMed Central, England (Mar. 2015).

Cui, W., et al., "Tumor Necrosis Factor Alpha Increases Epithelial Barrier Permeability by Disrupting Tight Junctions in Caco-2 Cells," Brazilian Journal of Medical and Biological Research 43(4):330-337, Brazilian Association of Scientific Dissemination, Brazil (Apr. 2010).

Dorofeyev, A.E., et al., "Mucosal Barrier in Ulcerative Colitis and Crohn's Disease," Gastroenterology Research and Practice 2013:431231, Hindawi Publishing Corporation, Egypt (2013).

Egerod, K.L., et al., "A Major Lineage of Enteroendocrine Cells Coexpress CCK, Secretin, GIP, GLP-1, PYY, and Neurotensin but Not Somatostatin," Endocrinology 153(12):5782-5795, Oxford University Press, United States (Dec. 2012).

Essawy, M., et al., "Myofibroblasts and the Progression of Diabetic Nephropathy," Nephrology, dialysis, transplantation 12(1):43-50, Oxford University Press, England (Jan. 1997).

Fan, X.S., et al., "Expression of Lgr5 in Human Colorectal Carcinogenesis and Its Potential Correlation With Beta-catenin," International Journal of Colorectal Disease 25(5):583-590, Springer-Verlag, Germany (May 2010).

Farris, A.B., et al., "Morphometric and Visual Evaluation of Fibrosis in Renal Biopsies," Journal of the American Society of Nephrology 22(1):176-186, American Society of Nephrology, United States (Jan. 2011).

Fatehullah, A., et al., "Organoids as an in Vitro Model of Human Development and Disease," Nature Cell Biology 18(3):246-254, Macmillan Magazines Ltd., England (Mar. 2016).

Greifenberg, V., et al., "Myeloid-derived Suppressor Cell Activation by Combined LPS and IFN-gamma Treatment Impairs DC Development," European Journal of Immunology 39(10):2865-2876, Wiley-VCH, Germany (Oct. 2009).

Hilgendorf, C., et al., "Expression of Thirty-six Drug Transporter Genes in Human Intestine, Liver, Kidney, and Organotypic Cell Lines," Drug Metabolism and Disposition: The Biological Fate of Chemicals 35(8):1333-1340, American Society for Pharmacology and Experimental Therapeutics, United States (Aug. 2007).

International Search Report and Written Opinion for International Application No. PCT/US2017/061016, ISA/US, United States, mailed on Jan. 25, 2018, 11 pages.

Jones, C.R., et al., "Gut Wall Metabolism. Application of Pre-Clinical Models for the Prediction of Human Drug Absorption and First-Pass Elimination," The AAPS Journal 18(3):589-604, American Association of Pharmaceutical Scientists, United States (May 2016).

Kauffman, A.L., et al., "Alternative Functional in Vitro Models of Human Intestinal Epithelia," Frontiers in Pharmacology 4:79, pp. 1-8, Frontiers Media, Switzerland (Jul. 2013).

Kelly, O.G., et al., "Cell-surface Markers for the Isolation of Pancreatic Cell Types Derived From Human Embryonic Stem Cells," Nature Biotechnology 29(8):750-766, Nature America Publishing, United States (Jul. 2011).

Kim, R.B., et al., "Interrelationship Between Substrates and Inhibitors of Human CYP3A and P-glycoprotein," Pharmaceutical Research 16(3):408-414, Kluwer Academic/Plenum Publishers, United States (Mar. 1999).

King, S.M., et al., "3D Proximal Tubule Tissues Recapitulate Key Aspects of Renal Physiology to Enable Nephrotoxicity Testing," Frontiers in Physiology 8:123, Frontiers Research Foundation, Switzerland (Mar. 2017).

Kragh, M., et al., "Divergent Response Profile in Activated Cord Blood T Cells From First-born Child Implies Birth-order-associated in Utero Immune Programming," Allergy 71(3):323-332, Wiley-Blackwell, Denmark (Mar. 2016).

Kudo, M., et al., "H(+)/peptide Transporter (PEPT2) Is Expressed in Human Epidermal Keratinocytes and Is Involved in Skin Oligopeptide Transport," Biochemical and Biophysical Research Communications 475(4):335-341, Elsevier, United States (Jul. 2016).

Kumar, S., "Measurement of Caspase Activity in Cells Undergoing Apoptosis," Methods in Molecular Biology 282:19-30, Humana Press, United States (2004).

Kwon, J.H., et al., "Colonic Epithelial Cells Are a Major Site of Macrophage Inflammatory Protein 3alpha (MIP-3alpha) Production in Normal Colon and Inflammatory Bowel Disease," Gut 51(6):818-826, British Medical Association, England (Dec. 2002).

Lahar, N., et al., "Intestinal Subepithelial Myofibroblasts Support in Vitro and in Vivo Growth of Human Small Intestinal Epithelium," PLOS One 6(11):e26898, Public Library of Science, United States (2011).

Li, M., et al., "Precision-cut Intestinal Slices: Alternative Model for Drug Transport, Metabolism, and Toxicology Research," Expert Opinion on Drug Metabolism & Toxicology 12(2):175-190, Informa Healthcare, England (2016).

Meixlsperger, S., et al., "CD141+ Dendritic Cells Produce Prominent Amounts of IFN-α After DsRNA Recognition and Can Be Targeted via DEC-205 in Humanized Mice," Blood 121(25):5034-5044, Elsevier, United States (Jun. 2013).

(56) References Cited

OTHER PUBLICATIONS

Mogensen, T.H., "Pathogen Recognition and Inflammatory Signaling in Innate Immune Defenses," Clinical Microbiology Reviews 22(2):240-273, American Society For Microbiology, United Status (Apr. 2009).

Musther, H., et al., "Animal Versus Human Oral Drug Bioavailability: Do They Correlate?," European Journal of Pharmaceutical Sciences 57(100):280-291, Elsevier Science B.V, Netherlands (Jun. 2014).

Nguyen, D.G., et al., "Bioprinted 3D Primary Liver Tissues Allow Assessment of Organ-Level Response to Clinical Drug Induced Toxicity In Vitro," PLOS One 11(7):e0158674, Public Library of Science, United States (Jul. 2016).

Notohara, K., et al., "Solid-pseudopapillary Tumor of the Pancreas: Immunohistochemical Localization of Neuroendocrine Markers and CD10," The American journal of surgical pathology 24(10):1361-1371, Wolters Kluwer Health, Inc., United States (Oct. 2000).

Oboshi, W., et al., "Flow Cytometric Evaluation of Surface CD56 Expression on Activated Natural Killer Cells as Functional Marker," The Journal of Medical Investigation 63(3-4):199-203, University of Tokushima School of Medicine, Japan (2016).

Paine, M.F., et al., "Characterization of interintestinal and intraintestinal variations in human CYP3A-dependent metabolism," The Journal of Pharmacology and Experimental Therapeutics 283(3):1552-1562, American Society for Pharmacology and Experimental Therapeutics, United States (Dec. 1997).

Pantenburg, B., et al., "Intestinal Immune Response to Human *Cryptosporidium* sp. Infection," Infection and Immunity 76(1):23-29, American Society For Microbiology, United Status (Jan. 2008).

Parton, R.G., et al., "Meeting of the Apical and Basolateral Endocytic Pathways of the Madin-darby Canine Kidney Cell in Late Endosomes," The Journal of cell biology 109(6 Pt 2):3259-3272, Rockefeller University Press, United States (Dec. 1989).

Paul, E.C., et al., "Conditionally Immortalized Intestinal Epithelial Cells: Novel Approach for Study of Differentiated Enterocytes," The American Journal of Physiology 265(1 Pt 1):C266-278, American Physiological Society, United States (Jul. 1993).

Pereira, C., et al., "Dissecting Stromal-epithelial Interactions in a 3D in Vitro Cellularized Intestinal Model for Permeability Studies," Biomaterials 56:36-45, Elsevier Science, Netherlands (Jul. 2015).

Peters, S.A., et al., "Predicting Drug Extraction in the Human Gut Wall: Assessing Contributions from Drug Metabolizing Enzymes and Transporter Proteins using Preclinical Models," Clinical Pharmacokinetics 55(6):673-696, Adis, part of Springer Science+Business Media, Switzerland (Jun. 2016).

Peyrin-Biroulet, L., "Anti-TNF Therapy in Inflammatory Bowel Diseases: A Huge Review," Minerva Gastroenterologica E Dietologica 56(2):233-243, Edizioni Minerva Medica, Italy (Jun. 2010).

Pfeffer, P.E., et al., "Carbon Uptake and the Metabolism and Transport of Lipids in an Arbuscular Mycorrhiza," Plant Physiology 120(2):587-598, American Society of Plant Biologists, United States (Jun. 1999).

Powell, D.W., et al., "Myofibroblasts. II. Intestinal Subepithelial Myofibroblasts," The American Journal of Physiology 277(2):C183-201, American Physiological Society, United States (Aug. 1999).

Prueksaritanont, T., et al., "Comparative Studies of Drug-metabolizing Enzymes in Dog, Monkey, and Human Small Intestines, and in Caco-2 Cells," Drug Metabolism and Disposition: The Biological Fate of Chemicals 24(6):634-642, American Society for Pharmacology and Experimental Therapeutics, United States (Jun. 1996).

Rampersad, S.N., "Multiple Applications of Alamar Blue as an Indicator of Metabolic Function and Cellular Health in Cell Viability Bioassays," Sensors 12(9):12347-12360, Basel, Switzerland (2012).

Rao, R.K., et al., "Tyrosine Phosphorylation and Dissociation of Occludin-ZO-1 and E-cadherin-beta-catenin Complexes From the Cytoskeleton by Oxidative Stress," The Biochemical journal 368(Pt 2):471-481, Portland Press on behalf of the Biochemical Society, England (Dec. 2002).

Reading, C.L., et al., "Expression of Unusual Immunophenotype Combinations in Acute Myelogenous Leukemia," Blood 81(11):3083-3090, Elsevier, United States (Jun. 1993).

Rieder, F., et al., "Animal Models of Intestinal Fibrosis: New Tools for the Understanding of Pathogenesis and Therapy of Human Disease," American Journal of Physiology. Gastrointestinal and Liver Physiology 303(7):G786-G801, American Physiological Society, United States (Oct. 2012).

Sanes, R.J., et al., "Molecular Heterogeneity of Basal Laminae: Isoforms of Laminin and Collagen IV at the Neuromuscular Junction and Elsewhere," The Journal of Cell Biology 111(4):1685-1699, Rockefeller University Press, United States (Oct. 1990).

Sato, T., et al., "Single Lgr5 Stem Cells Build Crypt-villus Structures in Vitro Without a Mesenchymal Nich," Nature 459(7244):262-265, Nature Publishing Group, England (May 2009).

Sato, T., et al., "Long-term Expansion of Epithelial Organoids From Human Colon, Adenoma, Adenocarcinoma, and Barrett's Epithelium," Gastroenterology 141(5):1762-1772, W.B. Saunders, United States (Nov. 2011).

Schweinlin, M., et al., "Development of an Advanced Primary Human In Vitro Model of the Small Intestine," Tissue Engineering. Part C, Methods 22(9):873-883, Mary Ann Liebert, Inc., United States (Sep. 2016).

Shi, Y. and Cheng, D., "Beyond Triglyceride Synthesis: The Dynamic Functional Roles of MGAT and DGAT Enzymes in Energy Metabolism," American Journal of Physiology. Endocrinology and Metabolism 297(1):E10-E18, American Physiological Society, United States (Jul. 2009).

Sinagoga, K.L. and Wells, J.M., "Generating Human Intestinal Tissues From Pluripotent Stem Cells to Study Development and Disease," The EMBO Journal 34(9):1149-1163, Wiley Blackwell, England (May 2015).

Speca, S., et al., "Cellular and Molecular Mechanisms of Intestinal Fibrosis," World Journal of Gastroenterology 18(28):3635-3661, Baishideng Publishing Group, United States (Jul. 2012).

Spence, J.R., et al., "Directed Differentiation of Human Pluripotent Stem Cells Into Intestinal Tissue in Vitro," Nature 470(7332):105-109, Nature Publishing Group, England (Feb. 2011).

Srinivasan, B., et al., "Teer Measurement Techniques for in Vitro Barrier Model Systems," Journal of laboratory automation 20(2):107-126, Sage, United States (Apr. 2015).

Sticova, E., et al., "Down-regulation of OATP1B Proteins Correlates With Hyperbilirubinemia in Advanced Cholestasis," International Journal of Clinical and Experimental Pathology 8(5):5252-5262, e-Century Pub. Corp., United States (May 2015).

Sundaramurthi, D., et al., "3D bioprinting technology for regenerative medicine applications," International Journal of Bioprinting 2(2):9-26, WHIOCE Publishing, Singapore (2016).

Susewind, J., et al., "A 3D Co-culture of Three Human Cell Lines to Model the Inflamed Intestinal Mucosa for Safety Testing of Nanomaterials," Nanotoxicology 10(1):53-62, Informa Healthcare, England (2016).

Taipalensuu, J., et al., "Correlation of Gene Expression of Ten Drug Efflux Proteins of the ATP-binding Cassette Transporter Family in Normal Human Jejunum and in Human Intestinal Epithelial Caco-2 Cell Monolayers," The Journal of Pharmacology and Experimental Therapeutics 299(1):164-170, American Society for Pharmacology and Experimental Therapeutics, United States (Oct. 2001).

Takenaka, T., et al., "Application of a Human Intestinal Epithelial Cell Monolayer to the Prediction of Oral Drug Absorption in Humans as a Superior Alternative to the Caco-2 Cell Monolayer," Journal of Pharmaceutical Sciences 105(2):915-924, Elsevier, United States (Feb. 2016).

Takenaka, T., et al., "Human Small Intestinal Epithelial Cells Differentiated From Adult Intestinal Stem Cells as a Novel System for Predicting Oral Drug Absorption in Humans," Drug Metabolism and Disposition: The Biological Fate of Chemicals 42(11):1947-1954, American Society for Pharmacology and Experimental Therapeutics, United States (Nov. 2014).

Tomisato, W., et al., "NSAIDs Induce Both Necrosis and Apoptosis in Guinea Pig Gastric Mucosal Cells in Primary Culture," American

(56) References Cited

OTHER PUBLICATIONS

Journal of Physiology. Gastrointestinal and Liver Physiology 281(4):G1092-1100, American Physiological Society, United States (Oct. 2001).

Van De Kerkhof, E.G., et al., "Innovative Methods to Study Human Intestinal Drug Metabolism in Vitro: Precision-cut Slices Compared With Ussing Chamber Preparations," Drug Metabolism and Disposition: The Biological Fate of Chemicals 34(11):1893-1902, American Society for Pharmacology and Experimental Therapeutics, United States (Nov. 2006).

Vandussen, K.L., et al., "Development of an Enhanced Human Gastrointestinal Epithelial Culture System to Facilitate Patient-based Assays," Gut 64(6):911-920, British Medical Association, England (Jun. 2015).

Venugopal, R., et al., "Inflammasome Inhibition Suppresses Alveolar Cell Permeability Through Retention of Neuregulin-1 (NRG-1)," Cellular Physiology and Biochemistry 36(5):2012-2024, Cell Physiol Biochem Press GmbH & Co KG, Germany (2015).

Wang, X., et al., "Cloning and Variation of Ground State Intestinal Stem Cells," Nature 522(7555):173-178, Nature Publishing Group, England (Jun. 2015).

Watson, C.L., et al., "An in Vivo Model of Human Small Intestine Using Pluripotent Stem Cells," Nature Medicine 20(11):1310-1314, Nature Publishing Company, United States (Nov. 2014).

Welti, R. and Wang, X., "Lipid Species Profiling: A High-throughput Approach to Identify Lipid Compositional Changes and Determine the Function of Genes Involved in Lipid Metabolism and Signaling," Current Opinion in Plant Biology 7(3):337-344, Current Biology Ltd., England (Jun. 2004).

Weng, Z., et al., "The Novel Flavone Tetramethoxyluteolin Is a Potent Inhibitor of Human Mast Cells," The Journal of Allergy and Clinical Immunology 135(4):1044-1052, Mosby, United States (Apr. 2015).

Whitehead, R.H., et al., "Establishment of Conditionally Immortalized Epithelial Cell Lines From Both Colon and Small Intestine of Adult H-2Kb-tsA58 Transgenic Mice," Proceedings of the National Academy of Sciences of the United States of America 90(2):587-591, National Academy of Sciences, United States (Jan. 1993).

Yamaura, Y., et al., "Functional Comparison of Human Colonic Carcinoma Cell Lines and Primary Small Intestinal Epithelial Cells for Investigations of Intestinal Drug Permeability and First-Pass Metabolism," Drug Metabolism and Disposition: The Biological Fate of Chemicals 44(3):329-335, American Society for Pharmacology and Experimental Therapeutics, United States (Mar. 2016).

Yin, X., et al., "Niche-independent High-purity Cultures of Lgr5+ Intestinal Stem Cells and Their Progeny," Nature Methods 11(1):106-112, Nature Pub. Group, United States (Jan. 2014).

Zhao, X., et al., "Spontaneous Immortalization of Mouse Liver Sinusoidal Endothelial Cells," International Journal of Molecular Medicine 35(3):617-624, D.A. Spandidos, Greece (Mar. 2015).

Madden, L.R., et al., "Bioprinted 3D Primary Human Intestinal Tissues Model Aspects of Native Physiology and ADME/Tox Functions," iScience 2:156-167, CellPress, United States (Apr. 2018).

Office Action mailed Mar. 8, 2022, in U.S. Appl. No. 16/349,109, Retting, K. N., et al., filed May 10, 2019, 8 pages.

* cited by examiner

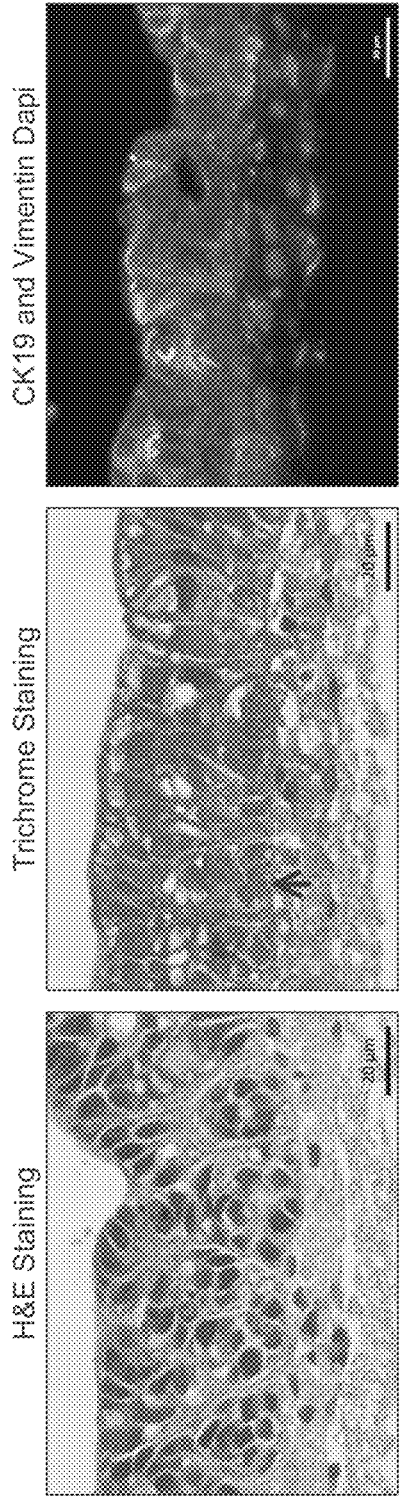
FIG. 2A  H&E Staining
FIG. 2B  Trichrome Staining
FIG. 2C  CK19 and Vimentin Dapi
FIG. 2D  CK19 and Collagen IV Dapi
FIG. 2E  Villin Dapi
FIG. 2F  E-Cadherin Dapi

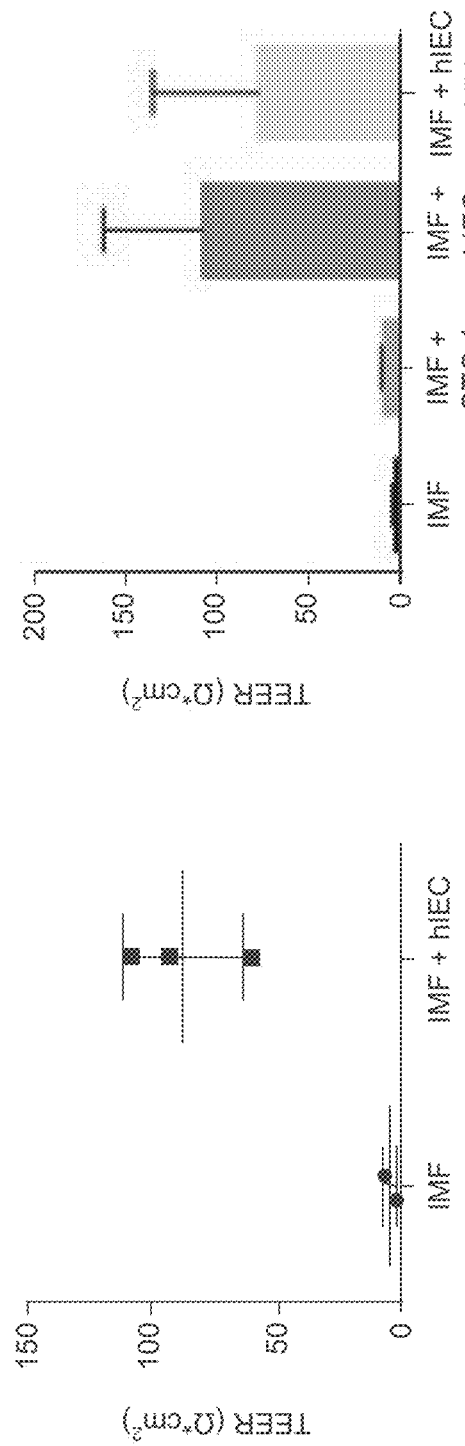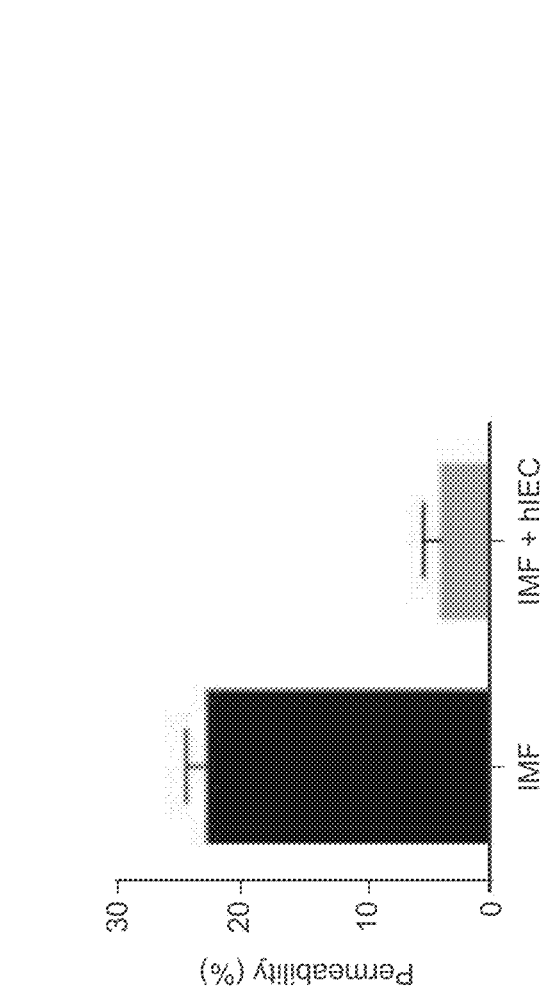
FIG. 19A
FIG. 19B
FIG. 19C

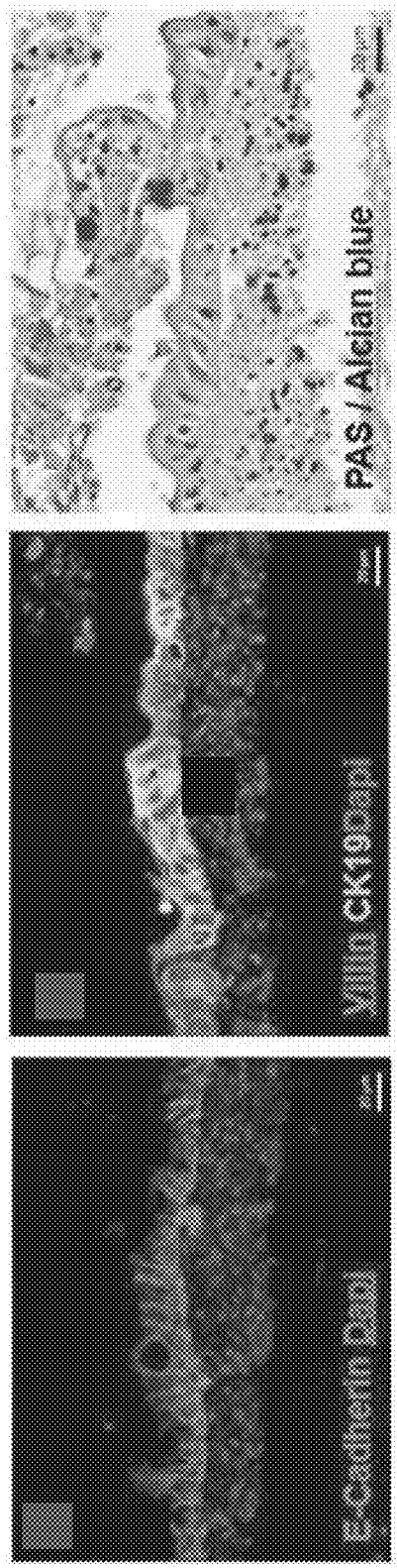

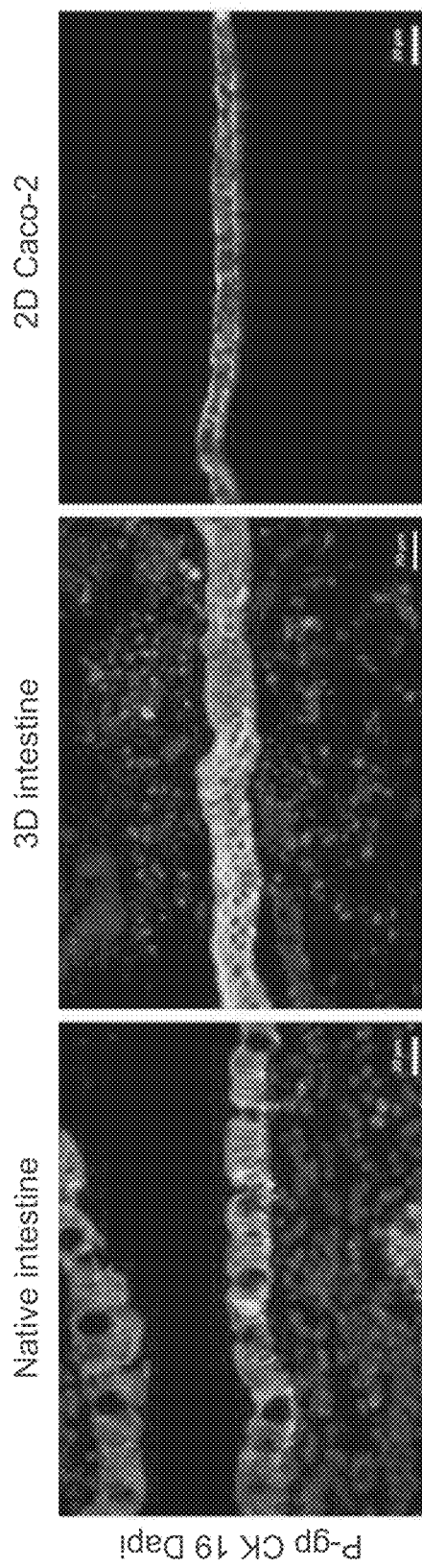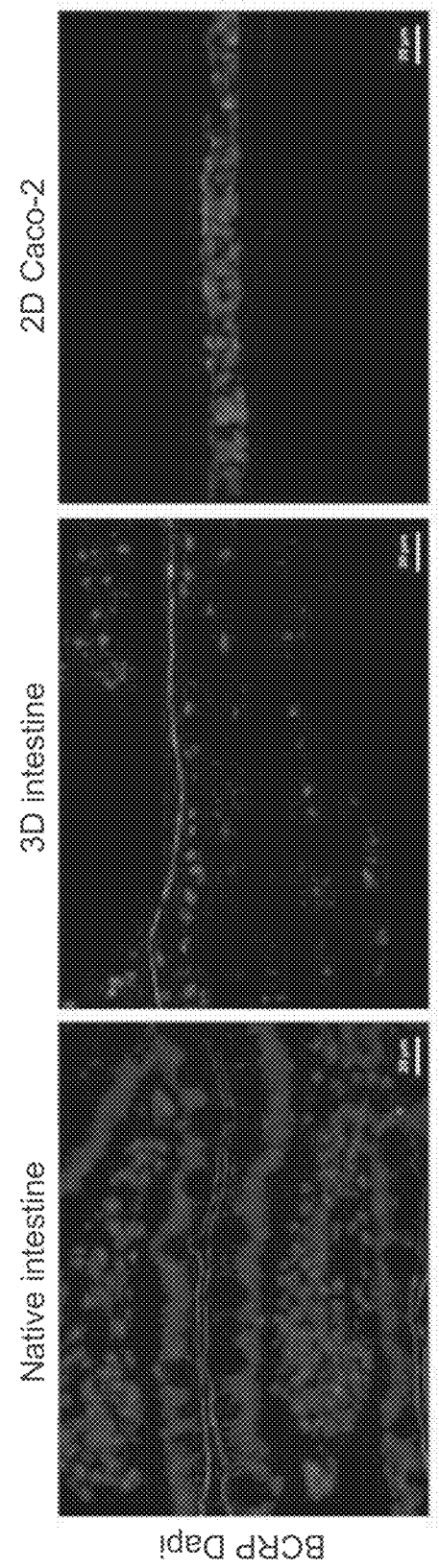
FIG. 25A
FIG. 25B

| | Untreated | | Ketoconazole | | Rifampicin | |
|---|---|---|---|---|---|---|
| | pmol/min/mg | | pmol/min/mg | % untreated | pmol/min/mg | % untreated |
| Donor 1 | 19.3 ± 1.9 | | 2.7 ± 0.2 | 13.9 ± 1.0 | 26.2 ± 3.9 | 136 ± 20 |
| Donor 2 | 2.85 ± 0.59 | | 0.81 ± 0.2 | 28.4 ± 7.5 | 10.1 ± 2.0 | 355 ± 69 |
| Donor 3 | 3.6 ± 3.6 | | 0.67 ± 0.1 | 18.6 ± 3.4 | 10.1 ± 0.9 | 281 ± 25 |

FIG. 32

ENGINEERED INTESTINAL TISSUE AND USES THEREOF

BACKGROUND OF THE INVENTION

Field of the Invention

The invention is in the field of intestinal tissue models and their use in assays. Disclosed are methods of assessing the ability of a candidate therapeutic agent to reverse, reduce or prevent intestinal injury by a potential toxic agent using a three-dimensional, engineered, bioprinted, biological intestinal tissue model. Also disclosed are methods of assessing the effect of an agent on intestinal function, the method comprising contacting the agent with a three-dimensional, engineered, bioprinted, biological intestinal tissue model.

Background Art

The intestinal mucosa plays a crucial role in regulating absorption, first-pass metabolism, clearance, drug-drug interactions, and can be a site of drug induced toxicity. Current in vitro systems and preclinical models utilized in drug development do not adequately recapitulate the complexities of native human intestinal tissue, leading to low safety and efficacy predictability and attrition in drug development.

Current preclinical models are limited in their ability to capture the complexities and function of human intestinal tissue [1-5]. Systemic availability, diminished efficacy, and off target effects remain challenges to the successful prediction of candidate drugs and contribute to attrition in drug development. Many predictive challenges can be attributed to the lack of preclinical tools to model the complexities of intestinal function in vitro [1-3]. Oral delivery is the most common method for drug administration. The intestine plays a crucial role in the extent of absorption of orally administered drugs and first-pass metabolism. The intestine also serves as critical site of off target toxicity for compounds such as NSAIDS [4] and chemotherapeutic agents [5], and serves as a site of drug-drug interactions [2, 6]. Standard 2D systems lack the complexity to accurately model outcomes such as low bioavailability, the result of a combination of low permeability and interplay of metabolic enzymes with influx and efflux transporters in the intestinal epithelium [3]. The predominant in vitro models used to study intestinal bioavailability and toxicity include intestinal microsomes and 2D monolayers. Microsomes are a convenient tool for the initial assessment of metabolism, but cannot model cellular level outcomes.

2D cell monolayer models lack native context of cell-cell and cell-matrix interactions and are phenotypically limited, while genetic disparity of animal models may not provide a high correlation with human outcomes [16]. Current in vitro intestinal models include 2D cell monolayer models of cell lines originating from colorectal and duodenal tumors (e.g., Caco-2, HT-29, HT29-18N2 and HuTu80). However, altered metabolism in tumor cells compared to normal tissue is a major disadvantage of these models. And, these tumor models do not represent features of native intestinal epithelium. The Caco-2 cell line is the most established cell model used to mimic passive transport and predict intestinal absorption. Limitations of the Caco-2 model include a lack of P-450 metabolizing enzyme expression and activity, lack of robust intestinal transporter expression and function, variation with passage number, and inconsistencies between clones in the line. Other 2D models include intestinal epithelial cells which, along with other cell lines, may have limited intestinal epithelial function due in part to their isolation from the other specialized epithelial cell types (ex: goblet cells, Paneth cells) as well as from the other supportive cell types present in the intestinal wall.

Limitations of commonly used cell lines have sparked the development of methods to use primary human intestinal cells. Monocultures of primary intestinal epithelial cells more closely resemble in vivo tissue but may have limited intestinal epithelial function in part to their isolation from the other supportive cell types present in the intestinal wall. In addition, testing in isolated epithelial monocultures prevents the ability to see effects on the interstitial and immune cells present in native tissue.

More complex 3D structures include intestinal segments and gut organoids derived from whole tissues or biopsies. The discovery of organoids to expand primary human intestinal cells [9, 10] or differentiate pluripotent stem cells [11] revealed another path to model the intestine in vitro. Organoids can be derived from all regions of the intestinal tract [12] and have been applied to many areas of intestinal research including organ development, disease modeling, and regenerative medicine [13, 14]. These structures suffer from low availability (from humans), limited viable lifespan in vitro, and may lack in vivo organ physiology. Notably, the closed lumens and the inward orientation of epithelia in intestinal organoids makes the apical surface relatively inaccessible for the direct stimulation they would normally experience in vivo, and makes organoids incompatible with most standard ADMF/Tox assays.

Intestinal slices derived from human tissue can provide the correct cellular architecture and complexity as well as level of metabolic activity of native tissue. Intestinal slices, however, have limited viability ex vivo and only function for about 24 hours. Furthermore, these tissues are not compatible with cryopreservation, which limits their use to short term studies [15].

Animal models are frequently used to estimate compound bioavailability, however genetic differences can lead to disparity in expression of metabolic enzymes and transporters compared to humans which can result in poor prediction [2, 3, 16].

To overcome existing limitations of the current in vitro systems, a n automated bioprinting platform was utilized to develop a reproducible, highly cellular 3D primary human tissue model to recapitulate key aspects of the architecture of the native intestinal mucosa. Compared to standard 2D monolayer cultures, the 3D bioprinted intestinal tissue models create a more physiologically relevant environment, allowing for cells to establish cell-cell and cell-matrix interactions found in native tissue. The model, which incorporates a polarized intestinal epithelium supported by an interstitial tissue layer, is compatible with both histological and standard biochemical ADMF/Tox readouts.

The 3D bioprinted intestinal tissues exhibit native-like layered architecture, including polarized epithelial morphology and physiological barrier function maintained for over two weeks in culture. The 3D bioprinted intestinal tissues express key P450 metabolic enzymes and transporters with similar endogenous levels compared to native intestine and demonstrate functional activity of both CYP2C9 and CYP3A4 enzymes and P-gp and BCRP efflux transporters. In addition, the bioprinted intestinal tissues respond to known toxicants indomethacin and TNFα with reduced barrier function, increased cytotoxicity, and changes in gene expression and cell morphology. The fully human primary cell-derived tissue combined with the reproducibility of the bioprinting platform and compatibility with standard assay approaches make this system a novel and practical in vitro tool for ADME-Tox applications across drug development.

SUMMARY OF THE INVENTION

The present invention provides intestinal tissue models that offer advantages over existing in vitro assay systems by providing an intestinal epithelial cell layer on top of a layer of intestinal interstitial tissue comprising myofibroblasts and, optionally, other key cell types such as myeloid immune cells, smooth muscle cells, endothelial cells and neurons. These intestinal tissue models allow one to see the impact of treatments in a more holistic system. And, the intestinal tissue models support epithelial morphology and function for an extended period of time in culture, thus enabling chronic studies of treatments. Because of their multi-cellularity and architecture, the intestinal tissue constructs provide a unique system to study multi-faceted processes including secretion, transport, cell-cell interactions and pathogenic processes, including inflammation and cancer.

The intestinal tissue models are valuable alternatives to animal models in the pharmaceutical industry for ADME-TOX applications in the lead optimization stage of drug development as well as disease modeling across all phases of drug discovery. In one embodiment, the intestinal tissue models described herein incorporate both epithelium and lamina propria to approximate the intestinal mucosa. In another embodiment, the tissue constructs comprise primary human intestinal epithelial cells in an epithelial compartment supported by primary human myofibroblasts in an interstitial compartment. The complexity of the model is optionally increased by incorporating additional specialized cell types, for example, enteroendocrine cells, into the epithelial layer to model endocrine function while goblet cells can be added to model mucosal barrier function. Additional complexity is achieved by the addition of immune cells or a submucosal compartment comprising endothelial cells and smooth muscle cells. An advantage of disclosed intestinal tissue constructs is that they are more physiologically relevant compared to tissue constructs having two-dimensional environment. The multi-cellularity and architecture of the tissues provide a unique opportunity to study complex multi-faceted processes of cells in a three-dimensional conformation including secretion, transport, cell-cell interactions and pathogenic processes. Through these interactions, three-dimensional tissues differentiate in a different manner than cells cultured in a two-dimensional monolayer, activating new signaling pathways and extracellular matrix interactions.

The intestinal tissue models described herein provide an opportunity to accurately study how compounds affect the intestinal tissue as well as to model pathogenic processes in the intestine. The intestinal tissue models disclosed herein are useful for predicting toxicity of pharmaceutical compounds earlier in the drug development process. By incorporating both diseased (ex: inflamed or tumor tissue) and normal cell compartments into the same tissue, the impact of therapeutic agents on both healthy and diseased tissue can be assessed in the same tissue system. Intestinal tissue constructs comprising primary cells are especially useful for personalized medicine.

Unexpectedly, the intestinal tissue models described herein made with only primary epithelial cells in the layer of intestinal epithelial cells express chromogranin A, secrete glucagon-like peptide-1 (GLP-1) and mucus, manifest the formation of goblet cells and secondary structure characteristic of native intestinal tissue, tissue thickening in culture, and CYP3A4 activity. This indicates that functional enteroendrocrine cells were produced.

In one embodiment, the invention provides a three-dimensional, engineered, bioprinted, biological intestinal tissue model comprising:
  (i) a layer of intestinal interstitial tissue comprising myofibroblasts; and
  (ii) a layer of intestinal epithelial cells on the layer of intestinal interstitial tissue, to form the three-dimensional, engineered, biological intestinal tissue model.

In some embodiments, at least one of the layer of intestinal interstitial tissue comprises myofibroblasts and layer of intestinal epithelial cells further comprises at least one type of immune cells. In some embodiments, the immune cells are myeloid cells. In some embodiments, the myeloid cells are monocytes, macrophages, neutrophils, basophils, eosinophils, dendritic cells or megakaryocytes. In some embodiments the immune cells are lymphoid cells. In some embodiments, the immune cells are present in at least one of (a) the interstitial layer, (b) the epithelial cell layer, (c) between the interstitial layer and the epithelial cell layer, (d) on top of the epithelial cell layer, and (e) below the interstitial cell layer.

In some embodiments, the layer of intestinal epithelial cells comprises primary epithelial cells from a healthy donor. In some embodiments, the layer of intestinal epithelial cells comprises primary epithelial cells from a diseased donor. In some embodiments, the diseased donor has celiac disease, Crohn's disease, ulcerative colitis, irritable bowel syndrome, hemorrhoids, diverticulitis, inflammatory bowel disease, microscopic colitis, lymphocytic colitis, collagenous colitis, an endocrine disorder, a metabolic disorder, obesity, diabetes, dyslipidemia, intestinal or colorectal cancer.

In some embodiments, the layer of intestinal epithelial cells further comprises at least one stem cell population. In some embodiments, the at least one stem cell population is capable of differentiating. In some embodiments, the intestinal tissue model further comprises tumor(s), tumor fragment(s), tumor cells or immortalized cells. In some embodiments, the tumor(s), tumor fragment(s), tumor cells or immortalized cells are colorectal tumor(s), tumor fragment(s), tumor cells or immortalized cells. In some embodiments, the tumor(s), tumor fragment(s), tumor cells or immortalized cells are present in a layer or compartment within the intestinal tissue model.

In some embodiments, the layer of intestinal epithelial cells and layer of interstitial tissue comprises primary epithelial cells from a healthy donor. In some embodiments, the layer of intestinal epithelial cells and layer of interstitial tissue comprises primary epithelial cells from a diseased donor.

In some embodiments, the intestinal tissue model exhibits at least one of the following:
  (a) apical staining of villin;
  (b) tight junctions;
  (c) an apical brush border;
  (d) villi-like structures on the epithelial surface;
  (e) a basal lamina between the layer of interstitial tissue and layer of epithelial cells;
  (f) secretes mucus;
  (g) expresses CYP3A4;
  (h) expresses p-glycoprotein;
  (i) expresses glucagon-like peptide-1;
  (j) expresses BCRP;

(k) contains enteroendocrine cells; and
(l) contains goblet cells.

In some embodiments, the tissue model does not comprise fully mature, perfusable vasculature. In some embodiments, the tissue model does not comprise red blood cells. In some embodiments, the tissue model is not innervated, e.g. by the central nervous system.

In some embodiments, the layer of intestinal interstitial tissue comprising myofibroblasts and/or the layer of intestinal epithelial cells is substantially a monolayer. In some embodiments, the intestinal tissue model further comprises a biocompatible membrane in contact with the intestinal tissue layer. In some embodiments, the model is at least 2 cell layers thick.

In some embodiments, the intestinal tissue model comprises a plurality of the intestinal tissue models are configured to form an array. In some embodiments, the array is present in the wells of a microtiter plate. In some embodiments, the intestinal model is in culture subject to static culture conditions. In some embodiments, the intestinal model is in culture subject to non-static culture conditions.

In some embodiments, the intestinal tissue model comprises at least one first region that comprises normal layers of intestinal interstitial tissue and intestinal epithelial cells and at least one second region that comprises layers of intestinal interstitial tissue and intestinal epithelial cells, wherein at least one of the layers of the second region comprises cells from a diseased donor.

Also provided is a non-human animal model of an intestinal disorder or injury comprising a non-human animal implanted therein the intestinal tissue model. In some embodiments, the non-human animal is an immunodeficient rodent.

Also provided is a method of assessing the ability of a candidate therapeutic agent to reverse, reduce, induce or prevent an intestinal disorder or injury, the method comprising:
(a) contacting the intestinal tissue model or the non-human animal model with the candidate therapeutic agent, wherein the intestinal tissue model has a phenotype of an intestinal disorder or injury;
(b) determining the viability or functionality of the intestinal tissue cells; and
(c) assessing the ability of the candidate therapeutic agent to reverse, reduce, induce or prevent an intestinal disorder or injury based on the determined viability or functionality of the intestinal tissue cells compared to a control intestinal tissue model that has not been contacted with the candidate therapeutic agent.

In some embodiments, the phenotype of an intestinal disorder or injury is induced by contacting the intestinal tissue model with a treatment, compound, or infectious agent that gives rise to the phenotype. In some embodiments, the phenotype of an intestinal disorder or injury is the presence of tumor(s), tumor fragment(s), tumor cells, or immortalized cells in the intestinal tissue model. In some embodiments, the ability of a candidate therapeutic agent to reverse, reduce, induce or prevent an intestinal disorder or injury is reduced tumor(s), tumor fragment(s), tumor cells, or immortalized cells invasion or metastasis.

Also provided is a method of assessing the ability of a candidate therapeutic agent to reverse, reduce, induce or prevent an intestinal disorder or injury, the method comprising:
(a) contacting the intestinal tissue model or the non-human animal model with the candidate therapeutic agent;
(b) determining the viability or functionality of the intestinal tissue cells; and
(c) assessing the ability of the candidate therapeutic agent to reverse, reduce, induce or prevent an intestinal disorder or injury based on the determined viability or functionality of the intestinal tissue cells compared to a control intestinal tissue model that has not been contacted with the candidate therapeutic agent.

In some embodiments, the epithelial cells and/or the myofibroblasts of the intestinal tissue model are obtained from a diseased donor. In some embodiments, the diseased donor has celiac disease, Crohn's disease, ulcerative colitis, irritable bowel syndrome, hemorrhoids, diverticulititis, inflammatory bowel disease, microscopic colitis, lymphocytic colitis, collagenous colitis, an endocrine disorder, a metabolic disorders, obesity, diabetes, dyslipidemia, intestinal or colorectal cancer. In some embodiments, the intestinal disorder or injury is inflammation. In some embodiments, the intestinal disorder or injury is a physical injury and the intestinal tissue model is subjected to physical disruption prior to being contacted with the candidate therapeutic agent. In some embodiments, the intestinal disorder or injury is a fibrotic disorder. In some embodiments, the intestinal disorder or injury is an infectious disease. In some embodiments, the intestinal disorder or injury is cancer. In some embodiments, the cancer is colorectal cancer.

In some embodiments, the intestinal tissue model is contacted with a potential toxic agent prior to being contacted with the candidate therapeutic agent. In some embodiments, the potential toxic agent is a toxin, a therapeutic agent, an antimicrobial agent, a metal, an microorganism (e.g., bacteria, virus, parasite, fungus), or an environmental agent. In some embodiments, the potential toxic agent is an antiviral, an analgesic agent, an antidepressant agent, a diuretic agent, or a proton pump inhibitor. In some embodiments, the potential toxic agent is a cytokine, a chemokine, a small molecule drug, a large molecule drug, a protein or a peptide. In some embodiments, the potential toxic agent is a chemotherapeutic agent. In some embodiments, the potential toxic agent is ibuprofen, acetaminophen, lithium, acyclovir, amphotericin B, and aminoglycoside, a beta lactams, foscavir, ganciclovir, pentamidine, a quinolone, a sulfonamide, vancomycin, rifampin, adefovir, indinavir, didofovir, tenofovir, methotrexate, lansoprazole, omeprazole, pantopraxole, allopurinol, phenytoin, ifosfamide, gentamycin, or zoledronate. In some embodiments, the potential toxic agent is radiation. In some embodiments, the potential toxic agent is an immune activator or modulator.

In some embodiments, the viability or functionality of the intestinal tissue cells is determined by measuring an indicator of metabolic activity. In some embodiments, the indicator of metabolic activity is resazurin reduction, tetrazolium salt reduction or ATP level in the intestinal tissue model compared to a control. In some embodiments, the viability or functionality of the intestinal tissue model is barrier function compared to a control. In some embodiments, the viability or functionality of the intestinal tissue model is drug efflux compared to a control. In some embodiments, the viability or functionality of the intestinal tissue model is cytochrome P450 3A4 (CYP3A4) activity compared to a control. In some embodiments, the viability or functionality of the intestinal tissue model is RNA or protein expression compared to a control. In some embodiments, the viability or functionality of the intestinal tissue model is peptide secretion compared to a control. In some embodiments, the peptide is a cytokine. In some embodiments, the viability or functionality of the intestinal tissue model is determined by histology compared to a control. In some embodiments, the viability or functionality of the intestinal tissue cells is determined by identifying regeneration of the intestinal tissue cells compared to a control. In some embodiments, the viability or functionality of the intestinal tissue cells is determined by measuring mucus secretion compared to a control. In some embodiments, the viability or functionality of the intestinal tissue cells is determined by measuring transporter activity compared to a control. In some embodiments, the viability or functionality of the intestinal tissue cells is determined by measuring enzyme activity compared to a control. In some embodiments, the viability or functionality of the intestinal tissue cells is determined by measuring triglyceride synthesis compared to a control. In some embodiments, the viability or functionality of the intestinal tissue cells is determined by measuring chylomicron secretion activity compared to a control. In some embodiments, the viability or functionality of the intestinal tissue cells is determined by measuring collagen production compared to a control. In some embodiments, the viability or functionality of the intestinal tissue epithelial cells is measured over time. In some embodiments, provided is a method to reverse or reduce injury by a toxic agent, and the intestinal tissue model is contacted first with the toxic agent and then with the candidate therapeutic agent. In some embodiments, provided is a method to reduce or prevent injury by a toxic agent, and the intestinal tissue model is contacted first with the candidate therapeutic agent and then with the toxic agent.

In some embodiments, the intestinal tissue model has been cultured in a cell culture medium prior to being contacted with the candidate therapeutic agent and the toxic agent. In some embodiments, the intestinal tissue model has been cultured for at least 3 days in the cell culture medium.

Also provided is a method of assessing the effect of a potential toxic agent on intestinal function, the method comprising:
(a) contacting the agent with the three-dimensional, engineered, bioprinted, biological intestinal tissue model; and
(b) measuring the effect of the agent on the viability or functionality of the intestinal tissue model cells.

In some embodiments, provided is a method to reverse or reduce injury by a toxic agent, and the intestinal tissue model is contacted first with the toxic agent and then the potential toxic agent is removed.

Also provided is a method of assessing the kinetics of intestinal absorption of an agent, the method comprising:
(a) contacting the agent with the three-dimensional, engineered, bioprinted, biological intestinal tissue model; and
(b) measuring the kinetics of absorption by the intestinal tissue model.

Also provided is method of predicting the effective dosing concentration and dosing schedule of a candidate therapeutic agent, the method comprising:
(a) contacting varying concentrations or amounts of the agent with the three-dimensional, engineered, bioprinted, biological intestinal tissue model; and
(b) measuring the effect of the agent on the viability or functionality of the intestinal tissue model cells over time; and
(c) measuring the recovery of the intestinal tissue model cells over time to determine the minimum timing between doses that provide efficacy.

In some embodiments, the method further comprises:
(d) removing the agent; and
(e) assessing whether the absence of the agent results in improved viability or functionality of the intestinal tissue model.

Also provided is a method of making the intestinal tissue model, the method comprising:
(a) depositing a layer comprising intestinal myofibroblasts onto a biocompatible surface; and
(b) depositing a layer of intestinal epithelial cells onto the layer of intestinal myofibroblasts.

In some embodiments, at least one of the intestinal myofibroblasts and intestinal epithelial cells are deposited by bioprinting. In some embodiments, at least one of the intestinal myofibroblasts and intestinal epithelial cells are deposited by ink-jet printing. In some embodiments, at least one of the intestinal myofibroblasts and intestinal epithelial cells are deposited by extrusion. In some embodiments, at least one of the intestinal myofibroblasts and intestinal epithelial cells are deposited by microvalve printing (MSV). In some embodiments, at least one of the intestinal myofibroblasts and intestinal epithelial cells are deposited by inkjet printing. In some embodiments, at least one of the intestinal myofibroblasts and intestinal epithelial cells are deposited as part of a bio-ink. In some embodiments, the bio-ink comprises a hydrogel. In some embodiments, the hydrogel is collagen. In some embodiments, the method further comprises depositing immune cells. In some embodiments, the immune cells are T cells, B cells, macrophages, dendritic cells, basophils, mast cells or eosinophils. In some embodiments, the immune cells are deposited as part of at least one of the intestinal tissue layers. In some embodiments, the immune cells are deposited in at least one of (a) the interstitial layer, (b) the epithelial cell layer, (c) between the interstitial layer and the epithelial cell layer, (d) on top of the epithelial cell layer, and (e) below the interstitial cell layer. In some embodiments, the immune cells are deposited as a layer or compartment. In some embodiments, the intestinal tissue model is deposited into the wells of a microtiter plate. In some embodiments, the method further comprises culturing the intestinal tissue model in cell culture media. In some embodiments, the intestinal tissue model is cultured for at least 3 days in the cell culture media. In some embodiments, the biocompatible surface is in the well of a microtiter plate.

BRIEF DESCRIPTION OF THE DRAWINGS

FIGS. 2A-2F are micrographs showing 3D printed tissues with Caco-2, demonstrating key architectural and tissue-specific features of the Caco-2 bioprinted 3D gut tissue. FIG. 2A shows bi-layered structure by H&E staining; FIG. 2B shows Trichrome staining of the 3D bioprinted tissues; FIG. 2C shows CK19 (epithelial) and Vimentin (fibroblast) co-staining; FIG. 2D shows CK19 and collagen IV co-staining; FIG. 2E shows Villin staining identifying the brush border; FIG. 2F shows E-Cadherin staining on epithelial cells indicating the tight junctions. Basal lamina can be seen in Trichrome staining in FIG. 2B (arrow) and collagen IV staining in FIG. 2D.

FIG. 3A shows histology time course of 3D bioprinted tissues with IMF interstitium supporting Caco-2/STC-1 epithelial cells. FIG. 3B shows PCNA and CK19 co-staining. PCNA staining shows that cells are proliferating, indicating that 3D Caco-2 tissues are highly viable in culture. FIG. 3C shows the lack of mucin production by Alcian blue/PAS staining and Mucin 2/CK19 co-staining, respectively.

FIG. 11A shows that 3D bi-layered tissues with correct architecture achieved using primary hIEC. Images at culture Day 9 reveal distinct epithelial layer with secondary structure formation. FIG. 11B shows that epithelial cells in 3D bi-layered tissues form tight junctions and polarize with expression patterning similar to native tissue. FIG. 11C shows that bioprinted gut tissues with primary hIEC in the epithelium demonstate correct architecture. Bi-layered tissues with correct expression pattern of IMF and hIEC markers maintained over 17-day culture period. FIG. 11D shows that bioprinted gut tissues have sustained viability and resemble native intestine.

FIG. 13A shows that, in 3D tissues with primary human intestinal epithelia cells cultured for 9 days, all transporters and enzymes analyzed are induced to levels higher than primary IEC as 3D tissues mature. P-gp exhibits the highest baseline expression in primary IEC while P-gp and CYP3A4 are the highest expressed genes in 3D tissues at Day 9. FIG. 13B are bar graphs showing gene expression as a ratio to CK19 expression (e.g., $2^{-(\Delta\Delta Ct)}$ PGP/$2^{-(\Delta\Delta Ct)}$ CK19) to remove any differences in total cell number. Relative fold change comparing expression at Day 9 to Day 0 shows induction in all genes as 3D tissues mature. Bioprinting approach creates reproducible tissues with low construct variability (n=3) per time point.

FIGS. 16A-16B are micrographs showing that 3D tissues printed with 100% STC-1 cells in the epithelial layer with no primary intestinal epithelial cells. Tissues demonstrate bi-layered architecture. Mouse STC-1 cells lack epithelial tight junctions and form invasive aggregates that may disrupt surrounding epithelium and increase barrier function variability. SV40 is used as a marker for STC-1 cells based on the transgenic mouse strain which this cell line was derived from. FIG. 16A shows modeling enteroendocrine function through incorporation of the mouse STC-1 cell line to bioprinted 3D gut tissues. Mouse intestinal cell line that secretes gut hormones CCK, GLP-1, GLP-2, GIP, and PYY are derived from tumors of double transgenic mice for SV40 large T antigen and polyoma virus small T antigen. Mouse STC-1 cell line is added to 3D tissue epithelium to model gut enteroendocrine function. STC-1 cells do not behave like epithelial cells. STC-1 cells alone form a thick layer, lack epithelial markers and tight junction formation. FIG. 16B shows that when incorporated with primary intestinal cells, STC-1 cells form invasive aggregates. STC-1 cells may disrupt surrounding epithelium.

FIG. 17A shows that, despite unusual behavior, tissues with STC-1 cells maintain correct architecture and expression pattering. FIG. 17B shows that tissues with STC-1 cells also develop a mucosal barrier. Arrows indicate the apical brush border and asterisk (*) indicates goblet cells and mucus.

FIGS. 19A-19C are bar graphs demonstrating barrier function in 3D tissues fabricated with primary intestinal epithelial cells. TEER and Lucifer yellow permeability are measured 10 days post epithelial seeding. Barrier function requires primary intestinal epithelial cells (hIEC). Tissues with only myofibroblasts (IMF) and STC-1 cells do not demonstrate barrier function.

FIGS. 20A-20B show that key transporters are present and induced over time in culture as tissues mature. Transporters regulating drug disposition (P-gp and BCRP) and the key bile acid transporter ASBT are highly expressed and increase over time. The data shows a clear advantage of 3D hIEC tissues over tissues with gold standard Caco-2 (FIG. 20B). Transporters regulating drug disposition (P-gp and BCRP) and the key bile acid transporter ASBT are highly expressed. Apical efflux transporter BCRP and influx transporter PEPT1 are highly upregulated over time (FIG. 20C). FIG. 20C shows that key metabolic enzymes are induced over time. Highly expressed CES2 is a major enzyme in the intestine and responsible for metabolism of various xenobiotics. Major Phase I cytochrome P450 enzyme CYP3A4 is highly induced (150×) with sustained expression over time. CYP3A4 expression in primary IECs is superior to Caco-2 cells (Caco-2 cells do not express CYP3A4). Major Phase II enzyme UGT1A1 is also highly expressed and induced over time. FIG. 20D shows gene expression of lipid biology. Transporters for fatty acids and cholesterol are expressed at low levels except NPC1L1 which is responsible for free cholesterol uptake. Enzymes involved in fat processing are highly expressed and increase from Day 0 then maintain to Day 17. FIG. 20E shows that key endocrine markers are present and induced as tissues mature. Key secreted peptides CCK, GCG, GIP, PYY, and SST are expressed and increase with time. These markers are also present in tissues that lack STC-1 cells, suggesting that enteroendocrine cells are present in hIEC tissues.

FIGS. 22A-22I show the architecture of a 3D bioprinted intestinal tissue. FIG. 22A show a bi-layered architecture is achieved by bioprinting an interstitial layer containing adult human intestinal myofibroblasts (IMF) followed by adult human intestinal epithelial cells (hIEC). FIGS. 22B-22C show that the vimentin expressing interstitial cells and CK19 expressing epithelial compartments remain separate over 17 days in culture. FIGS. 22D-22E show epithelial cells stained for tight junction E-Cadherin (FIG. 22D) and apical villin (FIG. 22E). FIGS. 22F-22G show mucus production from goblet cells is observed throughout culture. FIGS. 22H-22I show lysozyme stained Paneth cells (FIG. 22H) and chromogranin expressing enteroendocrine cells (FIG. 22I) are also present.

FIG. 23A shows general intestinal markers for intestinal epithelial lineage (LGR5, CDX2) and tight junctions are similar among the three groups. Epithelial subtype markers are highest for native and 3D bioprinted intestinal tissue. Drug inducible transcription factors VDR, NR1I2 (PXR), and NR1I3 (CAR) are similar for normal intestinal tissue function and 3D intestinal tissue. FIG. 23B shows native and 3D bioprinted intestinal tissue express all metabolic enzymes analyzed, including phase I cytochrome P450s, the majority of which Caco-2 cells lack. Genes regulating fatty acid metabolism DGAT1, MOGAT1, and MTTP are near equivalent in normal intestinal tissue function and 3D bioprinted intestinal tissue. FIG. 23C shows transporters are expressed by all three groups, with variation in the level. For efflux transporters, 3D bioprinted intestinal tissue is most similar to normal intestine tissue function while Caco-2 under express ABCB1 (P-gp) and ABCG2 (BCRP) while overexpressing ABCC2 (MRP2) and ABCC3 (MRP3). Uptake transporters SLC15A1 (PEPT1) and SLCO2B1 (OATP2B1) are similarly expressed by native and 3D bioprinted intestinal tissue, not by Caco-2 monolayers. Bile acid transporters vary for all three groups.

FIG. 24A shows trans-epithelial electrical resistance (TEER) was measured for 3D bioprinted intestinal tissue from day 6 to 21, showing increase early in culture, with maintenance of barrier function within physiological levels (dotted lines) after day 10 (n=24). Caco-2 monolayer at day 21 has TEER above physiological values. FIG. 24B shows permeability of test compounds was measured in the apical to basal direction, and shows distinction between low (Lucifer yellow, mitoxantrone), moderate (digoxin), and high (propranolol) permeability compounds.

FIGS. 25A-25D show P-gp and BCRP transporter function in 3D bioprinted intestinal tissue. FIGS. 25A-25B show P-gp and BCRP are apically localized in 3D bioprinted intestinal tissue, similar to normal intestine tissue function. Expression in Caco-2 monolayers in patchy at the apical surface. FIG. 25C shows P-gp substrate digoxin had greater permeability in the B to A direction with efflux ratio of 2.1. In the presence of P-gp inhibitor Zosuquidar, efflux ratio of digoxin was reduced to 1.2. FIG. 25D show BCRP/P-gp substrate topotecan had efflux ratio of 8.8 under control conditions. BCRP inhibition by Ko143 reduced B to A transport and efflux ratio decreased to 3.6. Dual inhibition of P-gp and BCRP resulted in ablation of transport with efflux ratio of 1.4. Level of significance: ****$P<0.0001$ by two-way ANOVA.

FIG. 26A shows CYP2C9 basal activity was validated by a luciferin activity assay and was reduced by inhibitor sulfaphenazole. FIGS. 26B-26C show that CYP3A4 activity was shown by luciferin activity assay (FIG. 26B) and midazolam hydroxylation (FIG. 26C), both of which were inhibited by ketoconazole. FIG. 26D shows that CYP3A4 induction via rifampicin treatment was detected by increased midazolam metabolism. FIG. 26E shows that rifampicin treatment increased gene expression of PXR regulated CYPs, ABCB1 (P-gp), and UGT1A1 but not control genes CK19 and ECAD. Level of significance: **$P<0.0001$. *$P<0.001$, **$P<0.01$ by two-way ANOVA.

FIG. 27A shows TEER measurements of tissues following 24 hour incubation with vehicle or varying doses of indomethacin (Indo), show dose response decrease in TEER with increasing indomethacin. FIG. 27B shows LDH activity increased with increasing indomethacin dose, suggesting increased cytotoxicity. FIG. 27C shows prostaglandin E, synthesis decreased to similar levels for all indomethacin doses tested, confirming drug activity. FIG. 27D shows histology of indomethacin treated tissues shows disruption of the epithelium and distorted nuclear staining at higher doses of indomethacin, accompanied by a reduction in E-Cadherin, a marker of barrier function. Level of significance: ****$P<0.0001$ by one-way ANOVA.

FIG. 28A shows that 3D bioprinted tissues treated with TNFα for 24 hours showed increased epithelial disorganization compared to controls. FIG. 28B shows increased LDH activity correlated with changes in cell morphology following TNFα treatment. FIG. 28c shows a subset of genes related to inflammation, COX2, IL8, and TNFα were upregulated in response to TNFα treatment. Level of significance: *$P<0.001$ by t-test in b; $P<0.01$, ****$P<0.0001$ by two-way ANOVA in c.

FIG. 32 shows inter-individual variability in midazolam metabolism of 3D bioprinted intestine tissues.

DETAILED DESCRIPTION OF THE INVENTION

Certain Definitions

Figure 1A:
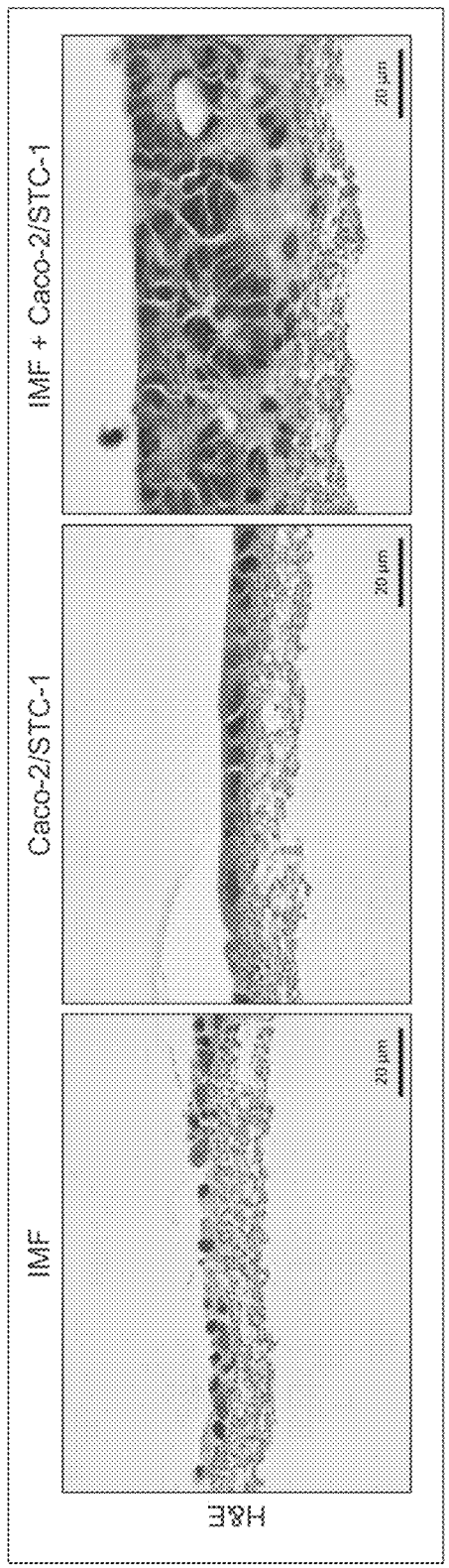
FIGS. 1A-1B illustrate a histological comparison by H&E staining (FIG. 1A) and Trichrome staining (FIG. 1B) of bioprinted intestinal tissue constructs with myofibroblasts (IMF) tissue alone, 2D Caco-2/STC-1 monolayers, and 3D tissues comprised of both layers (IMF+Caco-2/STC-1) at Day 7 (full culture time 11 days). Seeded alone, both IMF and epithelial cells (Caco-2/STC-1) form monolayers in culture over 11 days. When bioprinted together, the epithelial cells form secondary structures and the IMF produce more collagen as seen in Trichrome staining (blue).

Unless otherwise defined, all technical terms used herein have the same meaning as commonly understood by one of ordinary skill in the art to which this invention belongs. As used in this specification and the appended claims, the singular forms "a," "an," and "the" include plural references unless the context clearly dictates otherwise. Any reference to "or" herein is intended to encompass "and/or" unless otherwise stated.

As used herein, "about" means ±10% of the recited value. For example, about 10 includes 9-11.

As used herein, "array" means a scientific tool including an association of multiple elements spatially arranged to allow a plurality of tests to be performed on a sample, one or more tests to be performed on a plurality of samples, or both. In some embodiments, a plurality of the intestinal tissue models are configured to form an array. In some embodiments, the arrays are adapted for, or compatible with, screening methods and devices, including those associated with medium- or high-throughput screening. In further embodiments, an array allows a plurality of tests to be performed simultaneously. In further embodiments, an array allows a plurality of samples to be tested simultaneously. In some embodiments, the arrays are cellular microarrays. In further embodiments, a cellular microarray is a laboratory tool that allows for the multiplex interrogation of living cells on the surface of a solid support. In other embodiments, the arrays are tissue microarrays. In further embodiments, tissue microarrays include a plurality of separate tissues or tissue samples assembled in an array to allow the performance of multiple biochemical, metabolic, molecular, or histological analyses. In some embodiments, the array is present in the wells of a microtiter plate. Microtiter places are commercially available from Sigma Aldrich and other suppliers and are available in 6, 12, 24, 48, 96, 384 and 1546 sample well formats arranged in a rectangular matrix, although higher numbers of wells are possible.

As used herein, "assay" means a procedure for testing or measuring the presence or activity of a substance (e.g., a chemical, molecule, biochemical, protein, peptide, hormone, or drug, etc.) in an organic or biologic sample (e.g., cell aggregate, tissue, organ, organism, etc.).

As used herein, "basal lamina" means a layer comprising collagen between the intestinal interstitial tissue layer and the epithelial cell layer. Other layers may also be present in the intestinal tissue model.

As used herein, "biocompatible membrane" means a membrane that is not toxic to tissue.

As used herein, "bio-ink" means a liquid, semi-solid, or solid composition for use in bioprinting. In some embodiments, bio-ink comprises cell solutions, cell aggregates, cell-comprising gels, multicellular bodies, or tissues. In some embodiments, the bio-ink additionally comprises non-cellular materials that provide specific biomechanical properties that enable bioprinting. In some embodiments, the bio-ink comprises an extrusion compound. In some cases, the extrusion compound is engineered to be removed after the bioprinting process. In other embodiments, at least some portion of the extrusion compound remains entrained with the cells post-printing and is not removed.

As used herein, "bioprinting" means utilizing three-dimensional, precise deposition of cells (e.g., cell solutions, cell-containing gels, cell suspensions, cell concentrations, multicellular aggregates, multicellular bodies, etc.) via methodology that is compatible with an automated or semi-automated, computer-aided, three-dimensional prototyping device (e.g., a bioprinter). Suitable bioprinters include the Novogen Bioprinter® from Organovo, Inc. (San Diego, CA) and those described in U.S. Pat. No. 9,149,952 and U.S. Publ Appl. Nos. 2015/0093932, 2015/0004273, and 2015/0037445.

Bioprinting may be carried out by ink-jet printing (see, U.S. Pat. No. 7,051,654) and/or by extrusion printing (see, U.S. Pat. Nos. 9,149,952, 8,931,880, 9,227,339, 8,143,055, 8,728,807, and 9,315,043, and U.S. Published Appl. Nos. 2013/0190210, 2013/0164339, 2015/0282885, 2016/0040132, 2016/0097039, and 2016/0122723). In another embodiment, bioprinting may be carried out by microvalve printing, e.g., with a microfluidic device comprising a microvalve. See, for example, Beebe, D. J., Moore, J. S., Bauer, J. M., Yu, Q., Liu, R. H., Devadoss, C., Jo, B., 2000, "Functional hydrogel structures for autonomous flow control inside microfluidic channels", Nature 404, 588-590; and U.S. Pat. No. 6,663,821.

As used herein, "layer" means an association of cells in X and Y planes that is one or multiple cells thick. In some embodiments, the intestinal tissue model described herein includes at least two layers. In other embodiments, the intestinal tissue model described herein include a multiple of the two layers. In various embodiments, a layer forms a contiguous, substantially contiguous, or non-contiguous sheet of cells. In some embodiments, each layer of intestinal tissue model described herein comprises multiple cells in the X, Y, and Z axes.

As used herein, "polarized" means spatially asymmetric.

As used herein, "scaffold" refers to synthetic scaffolds such as polymer scaffolds and porous hydrogels, non-synthetic scaffolds such as pre-formed extracellular matrix layers, dead cell layers, and decellularized tissues, and any other type of pre-formed scaffold that is integral to the physical structure of the engineered tissue and not able to be removed from the tissue without damage/destruction of said tissue. In further embodiments, decellularized tissue scaffolds include decellularized native tissues or decellularized cellular material generated by cultured cells in any manner; for example, cell layers that are allowed to die or are decellularized, leaving behind the extracellular matrix (ECM) they produced while living. The term "scaffoldless," therefore, is intended to imply that pre-formed scaffold is not an integral part of the engineered tissue at the time of use, either having been removed or remaining as an inert component of the engineered tissue. "Scaffoldless" is used interchangeably with "scaffold-free" and "free of preformed scaffold."

As used herein a "subject" is an organism of any mammalian species including but not limited to humans, primates, apes, monkey, dogs, cats, mice, rats, rabbits, pigs, horses and others. A subject can be any mammalian species alive or dead. Subject includes recently deceased subjects or biopsy samples taken from a living subject.

A "non-human animal" may be any species other than human. In one embodiment, a non-human animal is a mammal. In another embodiment, a non-human animal is a vertebrate. In another embodiment, a non-human animal is selected from the group consisting of murine, ovine, canine, bovine, porcine and non-human primates.

As used herein "therapeutic substance" means any molecule, biologic, compound or composition that is approved to treat a disease, under investigation to treat a disease, or that elicits a biological response such as changes in DNA, RNA, peptide, polypeptide or protein.

As used herein, "tissue" means an aggregate of cells.

As used herein "viable" means that at least 50% of the cells are alive. In other embodiments, viable cells are at least 60%, 70%, 80%, 90%, 95%, 97% or more of cells in a bio-ink or tissue layer as determined by at least one test of viability. Tests for viability are known in the art, and include the alamarBlue™ Assay performed according to the manufacturer's protocol (Thermo Fisher, Carlsbad, CA).

Composition of the Intestinal Tissue Model

In some embodiments, the cells within the tissue model are organized spatially to recapitulate the laminar architecture of intestinal tissue; a polarized epithelium is present on top of a layer of interstitial tissue comprising intestinal myofibroblasts. In some embodiments, the intestinal tissue model further comprises a brush border on the epithelial cells.

In particular, non-limiting embodiments, the engineered intestinal tissues described herein comprise two major parts: 1) a interstitial layer comprising myofibroblasts; and 2) a polarized epithelial layer comprising epithelial cells. The layers may be deposited any known method of bioprinting including by ink-spray, extrusion, microvalve printing (MSV), laser-based bioprinting, and manual placement of the cells. In one embodiment, the cells are deposited using the Novogen MMX Bioprinter in such a way that the epithelial layer is apical to the myofibroblast layer. In another embodiment, structures are created by spatially-controlled deposition of cells mixed with a thermo-responsive hydrogel that degrades over time (Novogel® 2.0) and/or with deposition of aerosolized cellular materials by compressed gas propulsion (inkjet spray). In this embodiment, the two layers together model the wall of an intestinal tissue. This configuration is critical for modeling in vivo tissues and predicting native tissue responses. Response of the epithelial layer is predictive of native tissue response to drugs, chemicals, nutrients or biological agents, and may provide information relative to toxicity, efficacy, absorption, inflammation, or homeostasis.

In a particular embodiment, a myofibroblast layer is bioprinted, using continuous deposition techniques. In this embodiment, an epithelial layer is bioprinted, using ink-jet, microvalve, or extrusion deposition techniques onto the myofibroblast layer. A substantially contiguous layer of epithelium is consistent with in vivo tissues and is critical to replicate a physiologically relevant architecture. Ink-jet and microvalve deposition techniques provide the ability to deposit one or more thin layers of epithelial cells onto the potentially irregular surface of the myofibroblast layer. In such embodiments, ink-jet or microvalve deposition of the epithelial layer is optionally performed immediately after bioprinting of the myofibroblast layer or after the myofibroblast layer has been allowed to mature.

In some embodiments, the cells are bioprinted. In further embodiments, the bioprinted cells are cohered to form the engineered intestinal tissue models. In still further embodiments, the engineered intestinal tissue models are free or substantially free of pre-formed scaffold at the time of fabrication or the time of use. In some cases, bioprinting allows fabrication of tissues that mimic the appropriate cellularity of native tissue.

In some embodiments, the three-dimensional, engineered intestinal tissue models described herein are distinguished from tissues fabricated by prior technologies by virtue of the fact that they are three-dimensional, free of pre-formed scaffolds, consist essentially of cells, and/or have a high cell density (e.g., greater than 30% cellular, greater than 40% cellular, greater than 50% cellular, greater than 60% cellular, greater than 70% cellular, greater than 80% cellular, greater than 90% cellular, or greater than 95% cellular).

In some embodiments, the three-dimensional, engineered intestinal tissue models described herein are distinguished from native (e.g., non-engineered) tissues by virtue of the fact that they are non-innervated (e.g., substantially free of nervous tissue), substantially free of mature vasculature, and/or substantially free of blood components. For example, in various embodiments, the three-dimensional, engineered intestinal tissue models are free of plasma, red blood cells, platelets, and the like and/or endogenously-generated plasma, red blood cells, platelets, and the like.

In some embodiments, the model is not tubular in shape like a naturally occurring intestinal tissue, but is planar or sheet-like, this advantageously allows for in vitro assays and analysis. In some embodiments, the epithelial cells are not of human origin. In certain embodiments, the engineered intestinal tissue model lacks undifferentiated cells. In certain embodiments, the engineered intestinal tissue model lacks undifferentiated intestinal cells. In some embodiments, the three-dimensional, engineered intestinal tissue models described herein are distinguished from native intestinal tissue tissues in that they are substantially planar. In certain embodiments, the three-dimensional, engineered intestinal tissue models described herein possess functional improvements over native intestinal tissues; one example is high viability after a sustained amount of time in culture up for 14 days or more in culture. In some embodiments, the cells used in the intestinal tissue model are transformed or immortalized. In some embodiments, the cells used in the intestinal tissue model are transgenic and contain protein fusions with fluorescent proteins, like enhanced green fluorescent protein (EGFP), green fluorescent protein (GFP), red fluorescent protein (RFP), yellow fluorescent protein (YFP), or cyan fluorescent protein (CFP). In some embodiments, the cells used in the intestinal tissue model are transgenic and contain reporter constructs with fluorescent proteins; like EGFP, GFP, RFP, YFP, GFP; or luminescent proteins like firefly or renilla luciferase. In certain embodiments, any of the cells contain a deletion or insertion of 1, 2, 3, 4, 5, 6, 7, 8, 9, 10 genes or more. In some embodiments, the 3D intestinal tissue models are chimeras, wherein at least one cell is from a different mammalian species than any other cell of the 3D intestinal tissue model. In some embodiments, the 3D intestinal tissue models are chimeras, wherein at least one cell is form a different human donor than any other cell of the 3D intestinal tissue model. In another embodiment, the intestinal tissue models comprise cells derived from tumors and/or derived from induced pluripotent cells (iPSCs) and/or embryonic stem cells. Examples of tumor cells that may be in the intestinal tissue models include colorectal tumor cells.

There are key differences between the present intestinal tissue models and current in vitro models. The Caco-2 cell line is the most established cell model used to mimic passive transport and predict intestinal absorption and is considered the gold standard to model the intestinal barrier in vitro. Limitations of the Caco-2 model include lack of P-450 metabolizing enzyme activity (including key intestinal metabolic enzyme CYP3A4), lack of mucus production thus preventing accurate modeling of the mucosal barrier, variation with passage number, and inconsistencies between clones of the cell line (Table 1). Other 2D models may include primary intestinal epithelial cells which, along with cell lines, may have limited intestinal epithelial function due in part to their isolation from either other specialized epithelial cell types or from the other supportive cell types present in the intestinal wall. In addition, testing in isolated epithelial monocultures prevents the ability to see effects on the interstitial and immune cells present in native tissue.

TABLE 1

Key differences demonstrating the superiority of 3D tissue model compared to traditional 2D Caco-2 monolayer model.

| Feature | 2D Caco-2 monolayer | 3D Tissue Model |
| --- | --- | --- |
| Tissue-like cell density | yes | Yes |
| Epithelial tight junction formation | yes | Yes |
| Barrier Function | yes (artificially high) | yes (physiological levels) |
| Epithelial polarization | yes | yes |
| Transporter expression | yes (limited) | yes (high) |
| Mucus production | no | Yes |
| Presence of goblet cells | no | Yes |
| Presence of enteroendocrine cells | no | Yes |
| Presence of mucosal interstitial cells | no | Yes |
| Presence of immune cells | no | Yes |
| GLP-1 secretion | no | Yes |
| Metabolic enzyme (CYP3A4) expression | No | Yes |
| Metabolic enzyme (CYP3A4) activity | No | Yes |

More complex 3D structures including intestinal segments and gut organoids derived from whole tissue or biopsies have limited availability when derived from human tissue, have limited viable lifespan in vitro, and may lack in vivo organ physiology. Notably, these tissues are not laminar in structure and the inward orientation of epithelia in intestinal organoids makes the apical surface relatively inaccessible for direct stimulation or for assessing absorption. The 3D bioprinted intestinal tissues provide advantages over existing in vitro assay systems by incorporating multiple cell types including an intestinal epithelial cell layer on top of a layer of intestinal interstitial tissue comprising myofibroblast cells and, optionally, immune cells, smooth muscle cells, endothelial cells, or neurons. Furthermore, the model demonstrates tissue-like 3D architecture and functionality over an extended time in culture, thus enabling more chronic studies with clinically relevant endpoints. By including human primary cells, the intestinal tissue model can serve as an important adjunct, or in some cases, replacement of animal studies in which species differences in function hamper interpretations.

There are key differences between the tissue constructs and native tissues. Bioprinted tissue constructs differ from native gut which comprises centrally-innervated nervous and vascular tissue. Bioprinted tissue constructs differ from other 3D engineered methods that may employ scaffolds as use of scaffolds prevent achievement of tissue-like density and 3D dimensions, and those systems have limited spatial organization. Bioprinted tissue constructs differ from ex vivo-cultured tissue explants/slices/intestinal segments with regard to incorporation of blood, mature perfusable vascular components, and appendages. Tissue explants have the advantage of containing all resident cell types of the mucosa, submucosa, muscularis, and serosa as well as appendages; however, there are limited options for experimental manipulation of host genetics as well as restricted availability of such tissue samples. In addition, ex vivo tissue slices are only viable <14 days in culture and bioprinted tissue constructs can be maintained for greater than 14 days.

TABLE 2

Comparison of 2D, 3D bioprinted, and in vivo tissues

| | 2D Epithelial Monolayer | 3D Cell-Seeded Scaffolds | Ex Vivo Tissue Slices | In Vivo Native Tissues | 3D Bioprinted Tissues |
|---|---|---|---|---|---|
| Tissue-like cell density | yes | limited | yes | yes | yes |
| True 3D > 250 um in X, Y, Z axes | no | limited | yes | yes | yes |
| Multiple tissue-specific cell types | no | yes | yes | yes | yes |
| Spatially controlled cell compartments | no | limited | yes | yes | yes |
| Long term (>14 days) viability | no | yes | no | yes | yes |
| Incorporates mature neural and/or vascular systems | no | no | yes | yes | no |

Cellular Inputs

In some embodiments, the engineered tissues, arrays, and methods described herein include a plurality of cell types. In some embodiments, the intestinal tissue models comprise a layer of mammalian interstitial tissue comprising myofibroblasts and a layer of mammalian epithelial cells. In various embodiments, suitable epithelial cells are derived from human intestine (see, e.g., PLoS ONE 6.11:e26890 (2011), PMC. Web 28 Sep. 2016, or Sato et al., Nature 459:262-5 (2009)), or from directed differentiation of induced pluripotent stem cells (iPSC) or human embryonic stem cells (hES).

In some embodiments, the myofibroblasts are intestinal tissue myofibroblasts. In various embodiments, the intestinal tissue myofibroblasts are derived from primary cells isolated from human intestine. In some embodiments, the myofibroblasts are dermal or vascular in origin. In some embodiments, one or more of the cellular components are derived from a non-human mammal. In other embodiments, one or more of the cellular components are derived from a human. In other embodiments, the myofibroblasts are derived from normal tissue, diseased tissue or tumor tissue (e.g., colorectal tumor tissue).

Intestinal epithelial cells can be isolated from various regions of the gut including the duodenum, jejunum, ileum, and colon to more accurately mimic function of specific intestinal regions. Additional cell types can be incorporated into the intestinal constructs to provide additional functional features. Cell types can include alternative human intestinal cell lines (e.g. HT-29, HT29-18N2, and/or HuTu80 cell lines). Such cell lines may be considered for high throughput applications including 96 well platforms. In one embodiment, these cell lines are added as an epithelial layer in place of or in combination with primary intestinal epithelial cells.

In one embodiment, an immune component is incorporated into the intestinal tissue model by adding primary myeloid cells (e.g. monocytes, macrophages, and/or dendritic cells) and/or lymphoid cells/white blood cells (e.g. PBMC, neutrophils, T-cells, and/or B-cells, etc.). Such intestinal tissue model can be used to model disease phenotypes (IBD, colitis, Crohn's) and inflammation, as well as immune-oncology models. Immune cells can be incorporated into the myofibroblast interstitial layer by mixing directly with the myofibroblast bioink, by addition as a monolayer to the printing surface followed by printing of interstitial tissue on top, by addition as a printed layer or compartment adjacent to or embedded within the interstitial layer, and/or added as a mixture within the epithelium. In one embodiment, lymphoid cells are bioprinted as a compartmentalized aggregate just below the epithelial layer to mimic the native intestinal physiology of a Peyer's patch. In another embodiment, specialized intestinal epithelial cells (e.g. enteroendocrine, goblet, M, and/or Paneth cells) are incorporated into the epithelium to model specific intestinal functions. In another embodiment, enteroendocrine cells are added or generated from stem cells to model endocrine functions (e.g. GLP-1, PYY, CCK, and/or SST peptide secretion). In another embodiment, goblet cells are added to model mucosal barrier function for absorption, distribution, metabolism and excretion (ADME) and/or toxicology testing and/or study of microbiome interactions. In another embodiment, M cells and Paneth cells are added to modulate immune function. In another embodiment, primary human endothelial cells (e.g. HUVEC) are added to model the intestine microvasculature and incorporated into the interstitial layer or as an additional submucosal layer. In another embodiment, the intestinal tissue model comprises additional cells such as lymphatic endothelial cells and/or smooth muscle cells either in one or both layers of interstitial tissue and epithelial cells or as one or more separate layers. In another embodiment, neuronal cells are incorporated into a submucosal layer to model the enteric nervous system. Specialized cells may be derived from directed differentiation of stem cell populations within primary isolates or from iPS cells. Furthermore, primary cells or iPS cells can be derived from diseased donors to model intestinal diseases (e.g. addressing the genetic basis of IBD, colitis, and Crohn's disease).

In another embodiment, the intestinal tissue model may comprise multiple compartments across the x-y axis, e.g., wherein one compartment comprises normal tissue and an adjacent compartment comprises tissue with diseased cells, e.g., cells obtained from an individual having an intestinal disease or disorder. Such multi-compartment intestinal tissue constructions allows for the testing of candidate therapeutic treatments against normal and diseased tissue in the same construct that may be in a single tissue well.

In another embodiment, the intestinal tissue model is laminar, but contains secondary structures that mimic villi and/or crypts. In other embodiments, the intestinal tissue model comprises lumen-like structures or tubes that do not contain tissue but may contain cell culture media.

In another embodiment, the intestinal tissue model may comprise tumor(s), tumor fragment(s), tumor cells or immortalized cells in one or more layers or compartments of the intestinal tissue model. Such a tissue construct allows the testing of candidate therapeutic treatments on the tumor or cells as well as the study of tumor cell invasion and metastasis. Examples of tumor and tumor cells include intestinal adenocarcinoma cells, intestinal sarcoma cells, gastrointestinal stromal cells, carcinoid cancer cells, and intestinal lymphoma cells. In some embodiments, the tumor and tumor cells include but are not limited to Caco-2, HT-29, HT29-18N2, HuTu80 and STC-1 cells.

In another embodiment, the intestinal tissue model comprising tumor cells may be used as a diseased tissue model that may be implanted in a non-human animal as an in vivo model of cancer. In one embodiment, the tumor cells are colorectal cells. In another embodiment, the non-human animal is selected from the group consisting of may be any species including but not limited to murine, ovine, canine, bovine, porcine and any non-human primates. In a particular embodiment, the non-human animal is a rodent. In another particular embodiment, the non-human animal is an immunodeficient rodent. In a more specific embodiment, the animal is a NOD SCID gamma mouse. The intestinal tissue model may be implanted in any part of the non-human animal. In one embodiment, the intestinal tissue model is implanted in the peritoneum of the non-human animal.

Expression of markers associated with special cell types can include but are not limited to; myeloid cell markers (CD14, CD68, CD206), lymphoid cell markers (CD4. CD8, CD19, CD15), enteroendocrine markers (CHGA, GLP-1, PYY, CCK), goblet cell markers (MUC2), vascular markers (CD31), and stem cell markers in primary isolates (LGR5).

In some embodiments, the layer of interstitial tissue comprising myofibroblasts is substantially a monolayer. In some embodiments, the layer of interstitial tissue comprising myofibroblasts comprises a monolayer over 95% of its surface area. In some embodiments, the layer of interstitial tissue comprising myofibroblasts comprises a monolayer over 90% of its surface area. In some embodiments, the layer of interstitial tissue comprising myofibroblasts comprises a monolayer over 80% of its surface area. In some embodiments, the layer of interstitial tissue comprising myofibroblasts is greater than 1 cell thick. In some embodiments, the layer of interstitial tissue comprising myofibroblasts is greater than 2 cells thick. In some embodiments, the layer of interstitial tissue comprising myofibroblasts is greater than 3 cells thick. In some embodiments, the layer of interstitial tissue comprising myofibroblasts is greater than 4 cells thick. In some embodiments, the layer of interstitial tissue comprising myofibroblasts is greater than 5 cells thick. In some embodiments, the layer of interstitial tissue comprising myofibroblasts is greater than 10 cells thick. In some embodiments, the layer of interstitial tissue comprising myofibroblasts is greater than 20 cells thick. In some embodiments, the layer of interstitial tissue comprising myofibroblasts is greater than 50 cells thick. In some embodiments, the layer of interstitial tissue comprising myofibroblasts is greater than 100 cells thick. In some embodiments, the layer of interstitial tissue comprising myofibroblasts is 2-100 cells thick. In some embodiments, the layer of interstitial tissue comprising myofibroblasts is greater than 20 µm thick. In some embodiments, the layer of interstitial tissue comprising myofibroblasts is greater than 30 um thick. In some embodiments, the layer of interstitial tissue comprising myofibroblasts is greater than 40 µm thick. In some embodiments, the layer of interstitial tissue comprising myofibroblasts is greater than 50 µm thick. In some embodiments, the layer of interstitial tissue comprising myofibroblasts is greater than 100 µm thick. In some embodiments, the layer of interstitial tissue comprising myofibroblasts is greater than 200 µm thick. In some embodiments, the layer of interstitial tissue comprising myofibroblasts is greater than 500 µm thick. In some embodiments, the layer of interstitial tissue comprising myofibroblasts is greater than 600 µm thick. In some embodiments, the layer of interstitial tissue comprising myofibroblasts is greater than 1000 µm thick. In some embodiments, the layer of interstitial tissue comprising myofibroblasts is 20 µm-1000 µm thick. In some embodiments, the layer of interstitial tissue comprising myofibroblasts is less than 20 µm thick. In some embodiments, the layer of interstitial tissue comprising myofibroblasts is less than 30 µm thick. In some embodiments, the layer of interstitial tissue comprising myofibroblasts is less than 40 µm thick. In some embodiments, the layer of interstitial tissue comprising myofibroblasts is less than 50 µm thick. In some embodiments, the layer of interstitial tissue comprising myofibroblasts is less than 100 µm thick. In some embodiments, the layer of interstitial tissue comprising myofibroblasts is less than 200 µm thick. In some embodiments, the layer of interstitial tissue comprising myofibroblasts is less than 500 µm thick. In some embodiments, the layer of interstitial tissue comprising myofibroblasts is less than 600 µm thick. In some embodiments, the layer of interstitial tissue comprising myofibroblasts is less than 1000 µm thick.

In some embodiments, the intestinal tissue models comprise a layer of epithelial tissue comprising mammalian epithelial cells. In further embodiments, the epithelial cells are intestinal tissue epithelial cells (e.g., human intestinal epithelial cells). In still further embodiments, suitable intestinal tissue epithelial cells are primary isolates or cells derived from the directed differentiation of stem cells (e.g., iPSC-derived and/or human embryonic stem cell (hES)-derived). In some embodiments, the intestinal tissue epithelial cells are immortalized human cells. Methods to generate immortalized intestinal epithelial cells are described in, for example, Paul E C, Hochman J. Quaroni A (1993). Conditionally immortalized intestinal epithelial cells: novel approach for study of differentiated enterocytes. *Am J Physiol.* 265(1 Pt 1):C266-78 and Whitehead R H, VanEeden P E, Noble M D, Ataliotis P, Jat P S (1993). Establishment of conditionally immortalized epithelial cell lines from both colon and small intestine of adult H-2Kb-tsA58 transgenic mice. *Proc Natl Acad Sci* USA. 90(2):587-91. In other embodiments, the intestinal tissue epithelial cells are immortalized cells such as Ca Ski or HT-29 cells.

In some embodiments, the epithelial cells are derived from a non-human mammal such as, for example, rat, mouse, pig, or primate. In other embodiments, the epithelial cells are derived from a human.

In some embodiments, the layer of epithelial tissue consists essentially of intestinal tissue epithelial cells. In some embodiments, the layer of epithelial tissue consists essentially of primary intestinal tissue epithelial cells. In some embodiments, the layer of epithelial tissue consists essentially of intestinal tissue epithelial cells. In some embodiments, the layer of epithelial tissue consists essentially of primary intestinal tissue epithelial cells. In some embodiments, the layer of intestinal tissue is substantially a monolayer. In some embodiments, intestinal tissue epithelial cells are the only cells present in the layer of intestinal epithelial tissue. In some embodiments, the layer of epithelial tissue comprises tumor cells. In some embodiments, the layer of epithelial tissue comprises intestinal carcinoma, sarcoma, lymphoma and/or adenocarcinoma cells. In some embodiments, the layer of epithelial tissue comprises a monolayer over 95% of its surface area. In some embodiments, the layer of epithelial tissue comprises a monolayer over 90% of its surface area. In some embodiments, the layer of epithelial tissue comprises a monolayer over 80% of its surface area. In some embodiments, the layer of epithelial tissue is greater than 1 cell thick. In some embodiments, the layer of epithelial tissue is greater than 2 cells thick. In some embodiments, the layer of epithelial tissue is greater than 3 cells thick. In some embodiments, the layer of epithelial tissue is greater than 4 cells thick. In some embodiments, the layer of epithelial tissue is greater than 5 cells thick. In some embodiments, the layer of epithelial tissue is greater than 10 cells thick. In some embodiments, the layer of epithelial tissue is greater than 20 cells thick. In some embodiments, the layer of epithelial tissue is greater than 50 cells thick. In some embodiments, the layer of epithelial tissue is greater than 100 cells thick. In some embodiments, the layer of epithelial tissue is 2-100 cells thick. In some embodiments, the layer of epithelial tissue is greater than 20 µm thick. In some embodiments, the layer of epithelial tissue is greater than 30 µm thick. In some embodiments, the layer of epithelial tissue is greater than 40 µm thick. In some embodiments, the layer of epithelial tissue is greater than 50 µm thick. In some embodiments, the layer of epithelial tissue is greater than 100 µm thick. In some embodiments, the layer of epithelial tissue is greater than 200 µm thick. In some embodiments, the layer of epithelial tissue is greater than 500 µm thick. In some embodiments, the layer of interstitial tissue is greater than 00 µm thick. In some embodiments, the layer of epithelial tissue is greater than 1000 µm thick. In some embodiments, the layer of epithelial tissue is 20-1000 µm thick. In some embodiments, the layer of epithelial tissue is less than 1000 µm thick. In some embodiments, the layer of interstitial tissue is less than 600 µm thick. In some embodiments, the layer of epithelial tissue is less than 500 µm thick. In some embodiments, the layer of epithelial tissue is less than 200 µm thick. In some embodiments, the layer of epithelial tissue is less than 100 m thick. In some embodiments, the layer of epithelial tissue is less than 50 µm thick. In some embodiments, the layer of epithelial tissue is less than 40 µm thick. In some embodiments, the layer of epithelial tissue is less than 30 µm thick. In some embodiments, the layer of epithelial tissue is less than 20 µm thick.

Optionally, the intestinal tissue models comprise other cell types (e.g., GPL-1-producing cells, immune cells, endothelial cells, smooth muscle cells, neuronal cells, etc.). In some embodiments, the immune cells are T cells. In some embodiments, the immune cells are B cells. In some embodiments, the immune cells are NK cells. In some embodiments, the immune cells are dendritic cells. In some embodiments, the immune cells are macrophage cells.

A wide range of cell ratios are suitable. In some embodiments, the epithelial layer comprises, consists of, or consists essentially of intestinal tissue epithelial cells. In some embodiments, the myofibroblast cells are the only cells present in the layer of myofibroblast interstitial tissue. In some embodiments, the myofibroblasts and epithelial cells are present in the intestinal model in specific ratios. Suitable proportions of myofibroblasts include, by way of non-limiting examples, about 5, 10, 15, 20, 25, 30, 35, 40, 45, 50, 55, 60, 65, 70, 75, 80, 85, 90, and 95% myofibroblasts, including increments therein. Suitable proportions of epithelial cells include, by way of non-limiting examples, about 5, 10, 15, 20, 25, 30, 35, 40, 45, 50, 55, 60, 65, 70, 75, 80, 85, 90, and 95% epithelial cells, including increments therein. In certain embodiments, the ratio of myofibroblast to epithelial cells is at least 5:95, 10:90, 15:85, 20:80, 25:75, 30:70, 35:65, 40:60, 45:65, 50:50, 55:45, 60:40, 65:35, 70:30, 75:25, 80:20, 85:15, 90:10 or 95:5, including increments therein. In certain embodiments, the ratio of myofibroblast to epithelial cells is 5:95 to 95:5. In certain embodiments, the ratio of myofibroblast to epithelial cells is no more than 5:95, 10:90, 15:85, 20:80, 25:75, 30:70, 35:65, 40:60, 45:65, 50:50, 55:45, 60:40, 65:35, 70:30, 75:25, 80:20, 85:15, 90:10 or 95:5, including increments therein. In certain embodiments, the ratio of myofibroblast to epithelial cells is about 50:50. In certain embodiments, the ratio of myofibroblast to epithelial cells is from about 60:40 to about 40:60.

A wide range of cell concentrations are suitable for bio-inks. Bio-inks are suitably prepared for continuous deposition bioprinting techniques with concentrations of cells including, by way of non-limiting examples, about 1, 2, 3, 4, 5, 6, 7, 8, 9, 10, 20, 30, 40, 50, 60, 70, 80, 90, 100, 110, 120, 130, 140, 150, 160, 170, 180, 190, 200, 225, 250, 275, 300, or more, million cells per milliliter of bio-ink. In a particular embodiment, bio-ink prepared for continuous deposition bioprinting comprises about 100-200 million cells/mL. Bio-inks are suitably prepared for ink-jet deposition bioprinting techniques with concentrations of cells including, by way of non-limiting examples, about 0.25, 0.5, 1, 2, 3, 5, 10, 15 or more, million cells per milliliter of bio-ink. In a particular embodiment, bio-ink prepared for ink-jet deposition bioprinting comprises about 1-5 million cells/mL. In a particular embodiment, bio-ink prepared for ink-jet deposition bioprinting comprises about 1-4 million cells/mL. In a particular embodiment, bio-ink prepared for ink-jet deposition bioprinting comprises about 1-3 million cells/mL. In a particular embodiment, bio-ink prepared for ink-jet deposition bioprinting comprises about 1-2 million cells/mL.

In certain embodiments, the intestinal tissue bio-ink comprises between 50 million and 1 billion cells per milliliter. In certain embodiments, the intestinal tissue bio-ink comprises between 50 million and 900 million cells per milliliter. In certain embodiments, the intestinal tissue bio-ink comprises between 50 million and 800 million cells per milliliter. In certain embodiments, the intestinal tissue bio-ink comprises between 50 million and 700 million cells per milliliter. In certain embodiments, the intestinal tissue bio-ink comprises between 50 million and 600 million cells per milliliter. In certain embodiments, the intestinal tissue bio-ink comprises between 50 million and 500 million cells per milliliter. In certain embodiments, the intestinal tissue bio-ink comprises between 50 million and 400 million cells per milliliter. In certain embodiments, the intestinal tissue bio-ink comprises between 50 million and 300 million cells per milliliter. In certain embodiments, the intestinal tissue bio-ink comprises between 50 million and 200 million cells per milliliter. In certain embodiments, the intestinal tissue bio-ink comprises between 75 million and 600 million cells per milliliter. In certain embodiments, the intestinal tissue bio-ink comprises between 100 million and 600 million cells per milliliter. In certain embodiments, the intestinal tissue bio-ink comprises between 100 million and 500 million cells per milliliter. In certain embodiments, the intestinal tissue bio-ink comprises between 100 million and 400 million cells per milliliter. In certain embodiments, the intestinal tissue bio-ink comprises between 100 million and 300 million cells per milliliter. In certain embodiments, the intestinal tissue bio-ink comprises between 100 million and 200 million cells per milliliter. In certain embodiments, the intestinal tissue bio-ink comprises between 100 million and 150 million cells per milliliter.

In certain embodiments, the bio-ink is a viscous liquid. In certain embodiments, the bio-ink is a semi-solid. In certain embodiments, the bio-ink is a solid. In certain embodiments, the viscosity of the bio-ink is greater than 100 centipoise. In certain embodiments, the viscosity of the bio-ink is greater than 200 centipoise. In certain embodiments, the viscosity of the bio-ink is greater than 50) centipoise. In certain embodiments, the viscosity of the bio-ink is greater than 1,000 centipoise. In certain embodiments, the viscosity of the bio-ink is greater than 2,000 centipoise. In certain embodiments, the viscosity of the bio-ink is greater than 5,000 centipoise. In certain embodiments, the viscosity of the bio-ink is greater than 10,000 centipoise. In certain embodiments, the viscosity of the bio-ink is greater than 20,000 centipoise. In certain embodiments, the viscosity of the bio-ink is greater than 50,000 centipoise. In certain embodiments, the viscosity of the bio-ink is greater than 100,000 centipoise. In certain embodiments, the viscosity of the bio-ink is less than 100 centipoise. In certain embodiments, the viscosity of the bio-ink is less than 200 centipoise. In certain embodiments, the viscosity of the bio-ink is less than 500 centipoise. In certain embodiments, the viscosity of the bio-ink is less than 1,000 centipoise. In certain embodiments, the viscosity of the bio-ink is less than 2,000 centipoise. In certain embodiments, the viscosity of the bio-ink is less than 5,000 centipoise. In certain embodiments, the viscosity of the bio-ink is less than 10,000 centipoise. In certain embodiments, the viscosity of the bio-ink is less than 20,000 centipoise. In certain embodiments, the viscosity of the bio-ink is less than 50,000 centipoise. In certain embodiments, the viscosity of the bio-ink is less than 100,000 centipoise. In certain embodiments, the viscosity of the bio-ink is 100-100,000 centipoise.

Architectural Features of the Intestinal Tissue Model

The intestinal models of the present disclosure can be architecturally arranged in many configurations. In certain embodiments, the epithelial tissue and interstitial tissue comprising myofibroblasts are separate architecturally distinct layers that are in direct contact or separated by 1, 2, 3, 4, 5, 6, 7, 8, 9, 10, 15, 20 μm or more, including increments therein. In certain embodiments, the separation is due to the secretion and deposition of collagen between the two layers to form a basal lamina, which for the purposes of this disclosure is considered contact. In normal physiological tissue cells and cell layers are polarized to have an apical (lumen facing) surface and a basolateral surface, which faces other cells or tissue matrix. For the purposes of the intestinal tissue models disclosed herein the basolateral surface refers to a surface that faces another cell, an extracellular matrix or the surface of a biocompatible membrane or culture vessel. For the purposes of the intestinal tissue models disclosed herein the apical surface refers to a surface that faces away from the surface of a biocompatible membrane or culture vessel. In some embodiments, the intestinal tissue epithelial cells are polarized. In some embodiments, the layer of intestinal tissue possesses an apical and basolateral surface.

In one embodiment, one or bioinks may comprise a cellular mixture of some proportion of intestinal myofibroblasts, intestinal epithelial cells, Caco-2 epithelial cells, and STC-1 enteroendocrine cells and may contain a biomaterial support. In another embodiment, a bioink comprising primary intestinal myofibroblasts in Novogel® is printed to produce a tissue mimicking the mucosal interstitial layer. In another embodiment, a bioink comprising primary intestinal myofibroblasts in collagen is printed to produce a tissue mimicking the mucosal interstitial layer. In another embodiment, a cellular suspension comprising primary intestinal epithelial cells, Caco-2 cells, STC-1 cells or a mixture of these cell types is added to produce a tissue to mimic the epithelium. In one embodiment, the cellular suspension is manually added on top of the printed mucosal interstitial tissue to create a layered structure. In another embodiment, the manual addition of cell suspension is automated and bioprinted as a spray (e.g. by ink jet deposition (see U.S. Pat. No. 7,051,654) or microsolenoid (MSV) or extruded onto a printed tissue. The epithelial layer may be deposited as a single cell suspension or as cell aggregates. The epithelial layer may be deposited in growth media or in a bioink containing matrix materials. In one embodiment, the cells are mixed with basement membrane components including collagen 4, laminin, and heparin sulfate proteoglycans to improve contact between the epidermal and interstitial layers. In another embodiment, the epithelial layer may be deposited in growth media or in a bioink containing matrix materials subsequent to the deposition of a layer of basement membrane components.

In some embodiments, the intestinal tissue model further comprises a biocompatible membrane. In certain embodiments, the basolateral surface of the interstitial tissue comprising myofibroblasts is the surface attached to a biocompatible membrane or culture vessel; and the apical surface of the interstitial tissue comprising myofibroblasts interstitial tissue comprising is the surface not attached to a biocompatible membrane or culture vessel. In certain embodiments, the epithelial tissue layer is deposited onto and forms a layer on the apical surface of the interstitial tissue comprising myofibroblasts, thus forming two architecturally distinct layers. In certain embodiments, the epithelial tissue and interstitial tissue comprising myofibroblasts are in continuous contact. In certain embodiments, between 99%-100% of the epithelial tissue layer is in continuous contact with the interstitial tissue comprising myofibroblasts. In certain embodiments, between 95%-100% of the epithelial tissue layer is in continuous contact with the interstitial tissue comprising myofibroblasts. In certain embodiments, between 90%-100% of the epithelial tissue layer is in continuous contact with the interstitial tissue comprising myofibroblasts. In certain embodiments, 50-99% of the epithelial tissue layer is in continuous contact with the interstitial tissue comprising myofibroblasts. In certain embodiments, between 80%-100% of the epithelial tissue layer is in continuous contact with the interstitial tissue comprising myofibroblasts. In certain embodiments, between 70%-100% of the epithelial tissue layer is in continuous contact with the interstitial tissue comprising myofibroblasts. In certain embodiments, between 60%-100% of the epithelial tissue layer is in continuous contact with the interstitial tissue comprising myofibroblasts. In certain embodiments, between 50%-100% of the epithelial tissue layer is in continuous contact with the interstitial tissue comprising myofibroblasts. In certain embodiments, less than 99% of the epithelial tissue layer is in continuous contact with the interstitial tissue comprising myofibroblasts. In certain embodiments, less than 98% of the epithelial tissue layer is in continuous contact with the interstitial tissue comprising myofibroblasts. In certain embodiments, less than 97% of the epithelial tissue layer is in continuous contact with the interstitial tissue comprising myofibroblasts. In certain embodiments, less than 95% of the epithelial tissue layer is in continuous contact with the interstitial tissue comprising myofibroblasts. In certain embodiments, less than 90% of the epithelial tissue layer is in continuous contact with the interstitial tissue comprising myofibroblasts. In certain embodiments, less than 80% of the epithelial tissue layer is in continuous contact with the interstitial tissue comprising myofibroblasts. In certain embodiments, the epithelial tissue layer completely covers the apical surface of the interstitial tissue comprising myofibroblasts. In certain embodiments, the epithelial tissue layer covers between 99%-100% of the apical surface of the interstitial tissue comprising myofibroblasts. In certain embodiments, the epithelial tissue layer covers between 95%-1000% of the apical surface of the interstitial tissue comprising myofibroblasts. In certain embodiments, the epithelial tissue layer covers between 90%-100% of the apical surface of the interstitial tissue comprising myofibroblasts. In certain embodiments, the epithelial tissue layer covers between 80%-100° % of the apical surface of the interstitial tissue comprising myofibroblasts. In certain embodiments, the epithelial tissue layer covers between 70%-100% of the apical surface of the interstitial tissue comprising myofibroblasts. In certain embodiments, the epithelial tissue layer covers between 60%-1000% of the apical surface of the interstitial tissue comprising myofibroblasts. In certain embodiments, the epithelial tissue layer covers between 50%-100% of the apical surface of the interstitial tissue comprising myofibroblasts. In certain embodiments, the epithelial tissue layer covers less than 99% of the apical surface of the interstitial tissue comprising myofibroblasts. In certain embodiments, the epithelial tissue layer covers less than 98% of the apical surface of the interstitial tissue comprising myofibroblasts. In certain embodiments, the epithelial tissue layer covers less than 97% of the apical surface of the interstitial tissue comprising myofibroblasts. In certain embodiments, the epithelial tissue layer covers less than 95% of the apical surface of the interstitial tissue comprising myofibroblasts. In certain embodiments, the epithelial tissue layer covers less than 90% of the apical surface of the interstitial tissue comprising myofibroblasts. In certain embodiments, the epithelial tissue layer covers less than 80% of the apical surface of the interstitial tissue comprising myofibroblasts. In certain embodiments, the epithelial tissue layer covers less than 70% of the apical surface of the interstitial tissue comprising myofibroblasts. In certain embodiments, the epithelial tissue layer covers 50-99% of the apical surface of the interstitial tissue comprising myofibroblasts.

The intestinal tissue construct produced as described herein comprises one or more of the following features:

It comprises a bi-layer structure comprising a layer of intestinal epithelial cells on top of a supporting layer of intestinal mucosal interstitium comprising myofibroblasts, one or both layers optionally further comprising one or more other cells including immune cells.

It comprises one or more of the intestinal epithelial cell markers CK8, CK18 and CK19. Methods for detecting CK8, CK18 and CK19 markers are disclosed by Notohara K, Hamazaki S, Tsukayama C, Nakamoto S, Kawabata K, Mizobuchi K, Sakamoto K, Okada S (2000). Solid-pseudopapillary tumor of the pancreas: immunohistochemical localization of neuroendocrine markers and CD10. *Am. J Surg Pathol.* 24(10):1361-71.

It comprises one or more of the intestinal mofibroblast markers vimentin and a-sma. Methods for detecting vimentin and a-sma markers are disclosed by Essawy M, Soylemezoglu O, Muchaneta-Kubara E C, Shortland J, Brown C B, el Nahas A M (1997). Myofibroblasts and the progression of diabetic nephropathy. *Nephrol Dial Transplant* 12(1):43-50.

It manifests polarization of the intestinal epithelial cell with the formation of intracellular tight junctions. The tight junctions are identified by detecting E-Cadherin and/or ZO-1. Methods for detecting Cadherin and ZO-1 are disclosed by Radhakrishna K RAO, Shyamali BASUROY, Vijay U. RAO, Karl J. KARNAKY, Jr and Akshav GUPTA (2002). Tyrosine phosphorylation and dissociation of occludin-ZO-1 and E-cadherin-β-catenin complexes from the cytoskeleton by oxidative stress. *Biochem. J.* 368:471-481.

It manifests basolateral markers on the epithelial cells. Methods for detecting basolateral markers are disclosed by Parton R G, Prydz K, Bomsel M, Simons K, Griffiths G. (1989). Meeting of the apical and basolateral endocytic pathways of the Madin-Darby canine kidney cell in late endosomes. *J Cell Biol.* 109(6 Pt 2):3259-72.

It manifests brush boarder formation (villin). Methods for detecting brush boarder formation are disclosed by Chantret I, Barbat A, Dussaulx E, Brattain M G, Zweibaum A. (1988). Epithelial polarity, villin expression, and enterocytic differentiation of cultured human colon carcinoma cells: a survey of twenty cell lines. *Cancer Res.* 1988 48(7):1936-42.

It manifests mucosal barrier formation. Methods for detecting mucosal barrier formation are disclosed by Dorofeyev A E L, Vasilenko I V, Rassokhina O A, Kondratiuk R B (2013). Mucosal barrier in ulcerative colitis and Crohn's disease. *Gastroenterol Res Pract.* Epub 2013 May 7.

It expresses one or more of the transporters/enzymes P-gp/MDR1, CYP3A4, BCRP, MRP2, MRP3, PEPT1, OATPB1, ASBT, MDT1, OCTN2, OSTalpha, OSTbeta, CES2, CYP2C19, CYP2C8, CYP2C9, CYP2J2, CYP2S1, CYP4F12, GSTP1, UGT1A1. Methods for detecting P-gp/MDR1, CYP3A4, BCRP, MRP2, MRP3, PEPT1, and OATPB1 are disclosed by Taipalensuu J, Törnblom H, Lindberg G, Einarsson C. Sjöqvist F. Melhus H, Garberg P. Sjöström B, Lundgren B, Artursson P (2001). Correlation of gene expression of ten drug efflux proteins of the ATP-binding cassette transporter family in normal human jejunum and in human intestinal epithelial Caco-2 cell monolayers. *J Pharmacol Exp Ther.* 299(1):164-70; Sticova E, Lodererova A, van de Steeg E, Frankova S, Kollar M, Lanska V. Kotalova R, Dedic T, Schinkel A H, Jirsa M (2015). Down-regulation of OATP1B proteins correlates with hyperbilirubinemia in advanced cholestasis. *Int J Clin Exp Pathol.* 8(5):5252-5262; and Kudo M. Katayoshi T, Kobayashi-Nakamura K, Akagawa M, Tsuji-Naito K (2016). H+/peptide transporter (PEPT2) is expressed in human epidermal keratinocytes and is involved in skin oligopeptide transport. *Biochem Biophys Res Commun.* 475(4):335-341.

It manifests a basal lamina between the epithelial cell layer and the interstitial layer as evidenced by collagen IV staining. Methods of staining collagen IV are disclosed by Sanes J R, Engvall E, Butkowski R, Hunter D D (1990). Molecular heterogeneity of basal laminae: isoforms of laminin and collagen IV at the neuromuscular junction and elsewhere. *J Cell Biol.* 111(4):1685-99.

It manifests a barrier with permeability/absorption characteristics. Permeability/absorption characteristics may be identified by determining a transendothelial electrical resistance (TEER) value or Lucifer permeability. Methods for determining TEER values and Lucifer permeability are disclosed by Akbari P. Braber S, Alizadeh A, Verheijden K A, Schoterman M H, Kraneveld A D, Garssen J, Fink-Gremmels J (2015). Galacto-oligosaccharides Protect the Intestinal Barrier by Maintaining the Tight Junction Network and Modulating the Inflammatory Responses after a Challenge with the Mycotoxin Deoxynivalenol in Human Caco-2 Cell Monolayers and B6C3F1 Mice. *J Nutr.* 145(7): 1604-1613 and Venugopal R, Galam L, Cox R, Fukumoto J, Cho Y, Parthasarathy P T, Lockey R F, Kolliputi N (2015). Inflammasome Inhibition Suppresses Alveolar Cell Permeability Through Retention of Neuregulin-1 (NRG-1). *Cell Physiol Biochem.* 36(5):2012-24.

It manifests active transport via intestinal transporters and metabolic enzymes. Examples of intestinal transporters include HPT1, PEPT1, BCRP, MRP2, MDR1, OATP1A3, OATP2B1, OATP1B1, OATP1B3, SVCT1, GLUT2, GLUT5, and SGLT1. Methods for detecting the activity of intestinal transporters are disclosed by, for example, Hilgendorf C, Ahlin G, Seithel A, Artursson P, Ungell A L, Karlsson J (2007). Expression of thirty-six drug transporter genes in human intestine, liver, kidney, and organotypic cell lines. *Drug Metab Dispos.* 35(8):1333-40.

When it comprises myeloid immune cells, it manifests myeloid activation. In one embodiment, myeloid activation is induced by treatment with LPS and/or interferon-gamma. Methods for inducing myeloid activation is disclosed by Greifenberg V, Ribechini E, Rössner S, Lutz M B (2009). Myeloid-derived suppressor cell activation by combined LPS and IFN-gamma treatment impairs DC development. *Eur J Immunol.* 39(10):2865-76.

It manifests gene expression corresponding to the expressed markers. Examples of such genes include CYP3A4, CK19, CHGA, and MUC2. Methods for detecting such gene expression is disclosed by Taipalensuu J, Törnblom H, Lindberg G. Einarsson C, Sjöqvist F, Melhus H, Garberg P, Sjöström B, Lundgren B, Artursson P (2001). Correlation of gene expression of ten drug efflux proteins of the ATP-binding cassette transporter family in normal human jejunum and in human intestinal epithelial Caco-2 cell monolayers. *J Pharmacol Exp Ther.* 299(1):164-70; Chang S K, Dohrman A F, Basbaum C B, Ho S B, Tsuda T. Toribara N W, Gum J R, Kim Y S (1994). Localization of mucin (MUC2 and MUC3) messenger RNA and peptide expression in human normal intestine and colon cancer. *Gastroenterology.* 107(1):28-36; and Kelly O G, Chan M Y, Martinson L A, Kadoya K, Ostertag T M, Ross K G, Richardson M, Carpenter M K, D'Amour K A, Kroon E. Moorman M, Baetge E E, Bang A G (2011). Cell-surface markers for the isolation of pancreatic cell types derived from human embryonic stem cells. *Nat Biotechnol.* 29(8):750-6.

It manifests enteroendocrine function and production of gut peptides in response to nutrient stimulation. Enteroendocrine function and/or production of gut peptides may be determined by detecting changes in the levels of glucagon-like peptide-1 (GLP-1), PYY and/or cholecystokinin (CCK), somatostatin (SST), peptide YY (PYY), and gastric inhibitory peptide (GIP). Methods for detecting levels of GLP-1, PYY and CCK are disclosed by Egerod K L, Engelstoft M S, Grunddal K V, Nohr M K, Secher A. Sakata I, Pedersen J. Windelov J A, Fachtbauer E M, Olsen J, Sundler F, Christensen J P, Wierup N, Olsen J V, Holst J J, Zigman J M, Poulsen S S. Schwartz T W (2012). A major lineage of enteroendocrine cells coexpress CCK, secretin, GIP, GLP-1, PYY, and neurotensin but not somatostatin. *Endocrinology.* 153(12):5782-95.

It manifests the expression of additional markers associate with additional optional cell types including lymphoid cells (CD4, CD8, CD19 and CD15), enteroendrocrine markers (CHGA, GLP-1, PYY, CCK), goblet cell markers (MUC2), vascular markers (CD31), and stem cell markers (LGR5). Methods for detecting CD4, CD8, CD19, CD15, CHGA, GLP-1, PYY, CCK, MUC2, CD31, and LGR5 are disclosed by Reading C L, Estey E H, Huh Y O, Claxton D F, Sanchez G. Terstappen L W, O'Brien M C, Baron S, Deisseroth A B (1993). Expression of unusual immunophenotype combinations in acute myelogenous leukemia. *Blood.* 81(11):3083-90; Zhao X. Zhao Q. Luo Z, Yu Y. Xiao N, Sun X, Cheng L (2015). Spontaneous immortalization of mouse liver sinusoidal endothelial cells. *Int J Mol Med.* 35(3):617-24; Fan X S, Wu H Y, Yu H P, Zhou Q. Zhang Y F, Huang Q (2010). Expression of Lgr5 in human colorectal carcinogenesis and its potential correlation with beta-catenin. *Int J Colorectal Dis.* 25(5): 583-90; and references cited above.

It manifests mucus secretion/formation of a mucosal barrier. Mucus secretion/formation of a mucosal barrier may be determined by detecting mucin 2 (MUC2). Methods for detecting mucin 2 are disclosed by Chang S K, Dohrman A F, Basbaum C B, Ho S B, Tsuda T, Toribara N W. Gum J R, Kim Y S (1994). Localization of mucin (MUC2 and MUC3) messenger RNA and peptide expression in human normal intestine and colon cancer. *Gastroenterology.* 107(1):28-36.

It exhibits lipid metabolism/transport. Methods for detecting lipid metabolism/transport are disclosed by, for example, Welti R, Wang X (2004). Lipid species profiling: a high-throughput approach to identify lipid compositional changes and determine the function of genes involved in lipid metabolism and signaling. *Curr Opin Plant Biol.* 7(3):337-44 and Pfeffer P E, Douds Jr D D, Becard G, Shachar-Hill Y. Carbon uptake and the metabolism and transport of lipids in an arbuscular mycorrhiza. *Plant Physiol.* 1999 June; 120(2):587-98.

It manifests inflammation and immune responses. Inflammation and immune responses of tissues and methods for detecting are reviewed by, for example, Pantenburg B, Dann S M. Wang H C, Robinson P. Castellanos-Gonzalez A, Lewis D E, White A C Jr (2008). Intestinal immune response to human *Cryptosporidium* sp. infection. *Infect Immun.* 76(1):23-9 and Trine H. Mogensen (2009) Pathogen Recognition and Inflammatory Signaling in Innate Immune Defenses. *Clin Microbiol Rev.*

22(2): 240-273. In this embodiment, the tissue construct can be used to model intestinal injury (acute, subchronic and/or chronic) and recovery. In another embodiment, the tissue construct can be used to model gut diseases such as inflammatory bowel disease, ulcerative colitis and Crohn's disease. In another embodiment, the tissue construct can be used to evaluate the impact of immune modulation on either normal or diseased intestinal tissue.

When damaged, the tissue construct exhibits fibrosis and fibrotic scar formation. Fibrosis is caused by chronic tissue inflammation and characterized by an excessive deposition of extracellular matrix (ECM) components, such as collagens. The mechanisms of intestinal fibrosis are discussed in Silvia Speca. Ilaria Giusti, Florian Rieder, and Giovanni Latella (2012). Cellular and molecular mechanisms of intestinal fibrosis. *World J Gastroenterol.* 18(28): 3635-3661.

When myeloid immune cells are present, it comprises one or more of the myeloid cell markers CD14, CD206 and CD68. Methods for detecting CD14, CD206 and CD68 markers are disclosed by Catherine E. Angel, Chun-Jen J. Chen, Oliver C. Horlacher, Sintia Winkler, Thomas John, Judy Browning, Duncan MacGregor, Jonathan Cebon and P. Rod Dunbar (2009) Distinctive localization of antigen-presenting cells in human lymph nodes. *Blood* 2009(113): 1257-1267. B cells can be detected by cell surface expression of HLA-DR, CD19, and CD20. Activated B cells can be detected by cell surface expression of CD19, CD25, and CD30. Effector B cells can be detected by cell surface expression of CD138. T cells can be detected by cell surface expression of CD2, CD3, CD4, CD8, CD25, CD38, and CD54, etc. Activated T cells can be detected by cell surface expression of CD25, s CD25, CD27, CD30, CD69, CD71, CD154 (CD40L), and CD278 (ICOS). NK cells can be detected by cell surface expression of CD56. In humans, the major dendritic cells (DCs) subsets include conventional DCs (cDCs) and plasmacytoid DCs (pDCs), which differ in their expression of surface markers, Toll-like receptors (TLRs), and in the cytokines produced after activation, cDCs are positive for CD11c and carry either CD1c (BDCA1) or CD141 (BDCA3). CD1c$^+$ cDCs express TLR1 through TLR8 and TLR10 and CD1c$^-$CD141$^+$ cDCs expresses TLR1, 2, 3, 6, 8, and 10. pDCs express TLR1, 6, and 10. Detection can be done by flow cytometry immuno-phenotyping. Immunophenotyping can be done in heterogeneous cell populations or on a cell-by-cell basis (single cell analysis). Antibodies suitable for detections of lymphocyte specific cell surface markers are commercially available, such as from Abcam and R&D Systems, Inc. The lymphocytes cell surface markers and methods for detections are provided in Andrade M C, Ferreira S B, Gonealves L C, De-Paula A M, de Faria E S, Teixeira-Carvalho A, Martins-Filho O A (2013). Cell surface markers for T and B lymphocytes activation and adhesion as putative prognostic biomarkers for head and neck squamous cell carcinoma Hum Immunol. 74(12):1563-74; Kragh M. Larsen J M. Thysen A H, Rasmussen M A, Wolsk H M, Bisgaard H, Brix S (2016). Divergent response profile in activated cord blood T cells from first-born child implies birth-order-associated in utero immune programming. Allergy. 71(3):323-32; Oboshi W, Aki K. Tada T. Watanabe T, Yukimasa N, Ueno I, Saito K. Hosoi E (2016). Flow Cytometric Evaluation of Surface CD56 Expression on Activated Natural Killer Cells as Functional Marker. J Med Invest. 63(3-4):199-203: Meixlsperger S. Leung C S, Rdmer P C. Pack M. Vanoaica L D, Breton G, Pascolo S, Salazar A M, Dzionek A. Schmitz. J. Steinman R M, Manz C (2013). CD141+ dendritic cells produce prominent amounts of IFN-α after dsRNA recognition and can be targeted via DEC-205 in humanized mice. Blood. 121(25):5034-44.

In certain embodiments, at least 50% of intestinal epithelial cells of the intestinal epithelial layer form tight junctions with other intestinal epithelial cells. In certain embodiments, at least 70% of intestinal epithelial cells of the intestinal epithelial layer form tight junctions with other intestinal epithelial cells. In certain embodiments, at least 90% of intestinal epithelial cells of the intestinal epithelial layer form tight junctions with other epithelial cells. In certain embodiments, 50-90% of intestinal epithelial cells of the intestinal epithelial layer form tight junctions with other intestinal epithelial cells.

Architecture of the Epithelial Tissue Layer

Normally an epithelial tissue cell forms tight junctions with neighboring cells. The tight junctions are marked by the transmembrane protein family called the cadherins. One of these, E-cadherin, is especially prominent at tight junctions in intestinal tissue, and marks their formation. In certain embodiments, the epithelial tissue layer contains only (i.e., "consists of") cells that form tight junctions. In certain embodiments, substantially all cells in the epithelial tissue layer form a tight junction with at least one neighboring cell. In certain embodiments, between 99%-100% of cells in the epithelial tissue layer form a tight junction with at least one other cell. In certain embodiments, between 95%-100% of cells in the epithelial tissue layer form a tight junction with at least one other cell. In certain embodiments, between 90%-100% of cells in the epithelial tissue layer form a tight junction with at least one other cell. In certain embodiments, between 80%-100% of cells in the epithelial tissue layer form a tight junction with at least one other cell. In certain embodiments, between 70%-100% of cells in the epithelial tissue layer form a tight junction with at least one other cell. In certain embodiments, between 60%-100% of cells in the epithelial tissue layer form a tight junction with at least one other cell. In certain embodiments, between 50%-100% of cells in the epithelial tissue layer form a tight junction with at least one other cell. In certain embodiments, 50-99% of cells in the epithelial tissue layer form a tight junction with at least one other cell.

In another embodiment, the epithelial tissue layer exhibits a brush border characterized by microvilli as are present on native intestinal tissue. The brush boarder may be detected by apical staining of villin.

Viability and Density of the Cell Layers

An advantage of bioprinting by the methods of this disclosure is that cells can be printed at high density and high viability. In certain embodiments, the density of the epithelial/interstitial cell layer is greater than $1 \times 10^6$ cells per mL. In certain embodiments, the density of the epithelial/interstitial cell layer is at least $5 \times 10^6$ cells per mL. In certain embodiments, the density of the epithelial/interstitial cell layer is at least $10 \times 10^6$ cells per mL. In certain embodiments, the density of the epithelial/interstitial cell layer is at least $20 \times 10^6$ cells per mL. In certain embodiments, the density of the epithelial/interstitial cell layer is at least $50 \times 10^6$ cells per mL. In certain embodiments, the density of the epithelial interstitial cell layer is at least $100 \times 10^6$ cells per mL. In certain embodiments, the density of the epithelial/interstitial cell layer is at least $200 \times 10^6$ cells per mL. In certain embodiments, the density of the epithelial/interstitial cell layer is at least $500 \times 10^6$ cells per mL. In certain embodiments, the density of the epithelial/interstitial cell layer is between about $100 \times 10^6$ cells per mL and about $900 \times 10^6$ cells per mL. In certain embodiments, the density of the epithelial/interstitial cell layer is between about $100 \times 10^6$ cells per mL and about $700 \times 10^6$ cells per mL. In certain embodiments, the density of the epithelial/interstitial cell layer is between about $100 \times 10^6$ cells per mL and about $600 \times 10^6$ cells per mL. In certain embodiments, the density of the epithelial/interstitial cell layer is between about $100 \times 10^6$ cells per mL and about $500 \times 10^6$ cells per mL. In certain embodiments, the density of the epithelial/interstitial cell layer is between about $100 \times 10^6$ cells per mL and about $300 \times 10^6$ cells per mL. In certain embodiments, the density of the epithelial/interstitial cell layer is between about $100 \times 10^6$ cells per mL and about $200 \times 10^6$ cells per mL. In certain embodiments, the layer of epithelial/interstitial tissue or layer of epithelial tissue is between 70%-100% living cells by volume. In certain embodiments, the viability of the epithelial/interstitial tissue layer is greater than 99% living cells by volume. In certain embodiments, the viability of the epithelial/interstitial tissue layer is greater than 95% living cells by volume. In certain embodiments, the viability of the epithelial/interstitial tissue layer is greater than 90% living cells by volume. In certain embodiments, the viability of the epithelial/interstitial tissue layer is greater than 80% living cells by volume. In certain embodiments, the viability of the epithelial/interstitial tissue layer is greater than 70% living cells by volume. In certain embodiments, the viability of the epithelial/interstitial tissue layer is greater than 60% living cells by volume. In certain embodiments, the viability of the epithelial/interstitial tissue layer is greater than 50/living cells by volume. In certain embodiments, the viability of the epithelial/interstitial tissue layer is 50-99% living cells by volume. In certain embodiments, this viability is maintained for at least 8, 12, 24, 48, 72, 96, or more hours post printing. In certain embodiments, this viability is maintained for at least 1, 2, 3, 4, 5, 6, 7, 8, 9, 10, 11, 12, 13, 14, 21, or more days post printing. In certain embodiments, the density of the epithelial cell layer is at least $0.1 \times 10^5$ cells per mL. In certain embodiments, the density of the epithelial cell layer is at least $0.1 \times 10^5$ cells per mL. In certain embodiments, the density of the epithelia cell layer is at least $5 \times 10^5$ cells per mL. In certain embodiments, the density of the epithelial cell layer is at least $1 \times 10^6$ cells per mL. In certain embodiments, the density of the epithelial cell layer is at least $5 \times 10^6$ cells per mL. In certain embodiments, the density of the epithelia cell layer is at least $10 \times 10^6$ cells per mL. In certain embodiments, the density of the epithelial cell layer is at least $20 \times 10^6$ cells per mL. In certain embodiments, the density of the epithelial cell layer is at least $50 \times 10^6$ cells per mL. In certain embodiments, the density of the epithelial cell layer is at least $100 \times 10^6$ cells per mL. In certain embodiments, the density of the epithelial cell layer is at least $200 \times 10^6$ cells per mL In certain embodiments, the density of the epithelial cell layer is at least $500 \times 10^6$ cells per mL. In certain embodiments, the density of the epithelial cell layer is less than $1 \times 10^5$ cells per mL. In certain embodiments, the density of the epithelial cell layer is less than $2 \times 10^5$ cells per mL. In certain embodiments, the density of the epithelial cell layer is less than $5 \times 10^5$ cells per mL. In certain embodiments, the density of the epithelial cell layer is less than $1 \times 10^6 6$ cells per mL. In certain embodiments, the density of the epithelial cell layer is less than $5 \times 10^6$ cells per mL. In certain embodiments, the density of the epithelial cell layer is less than $10 \times 10^6$ cells per mL. In certain embodiments, the density of the epithelial cell layer is $1 \times 10^6$ cells per mL. In certain embodiments, the viability of the epithelial tissue layer is greater than 99% living cells by volume. In certain embodiments, the viability of the epithelial tissue layer is greater than 95% living cells by volume. In certain embodiments, the viability of the epithelial tissue layer is greater than 90% living cells by volume. In certain embodiments, the viability of the epithelial tissue layer is greater than 80% living cells by volume. In certain embodiments, the viability of the epithelial tissue layer is greater than 70% living cells by volume. In certain embodiments, the viability of the epithelial tissue layer is greater than 60% living cells by volume. In certain embodiments, the viability of the epithelial tissue layer is greater than 50% living cells by volume. In certain embodiments, the viability of the epithelial tissue layer is 50-99% living cells by volume. In certain embodiments, this viability is maintained for at least 8, 12, 24, 48, 72, or 96 hours post-printing. In certain embodiments, this viability is maintained for at least 1, 2, 3, 4, 5, 6, 7, 8, 9, 10, 11, 12, 13, or 14 days post-printing.

Non-Cellular Components of Bio-Inks and Cell Layers

Often cells or bio-inks that are bioprinted contain excipients or extrusion compounds that improve their suitability for bioprinting. Examples of extrusion compounds include, but are not limited to gels, hydrogels, peptide hydrogels, amino acid-based gels, surfactant polyols (e.g., Pluronic F-127 or PF-127), thermo-responsive polymers, hyaluronates, alginates, extracellular matrix components (and derivatives thereof), collagens, gelatin, other biocompatible natural or synthetic polymers, nanofibers, and self-assembling nanofibers. In some embodiments, the extrusion compound contains a synthetic polymer. In some embodiments, the extrusion compound contains a non-synthetic polymer that is not normally associated with mammalian tissues. In some embodiments, extrusion compounds are removed after bioprinting by physical, chemical, or enzymatic means. In some embodiments, the bio-inks of the present disclosure contain 1% or more extrusion compound by weight. In some embodiments, the intestinal tissue models of the present disclosure contain more than 1% extrusion compound by weight. In some embodiments, the bio-inks of the present disclosure contain less than 5% extrusion compound by weight. In some embodiments, the bio-inks of the present disclosure contain between 0%-2% extrusion compound by weight. In some embodiments, the bio-inks of the present disclosure contain less than 1% extrusion compound by weight. In some embodiments, the intestinal tissue models of the present disclosure contain between 0%-5% extrusion compound by weight. In some embodiments, the intestinal tissue models of the present disclosure contain less than 2% extrusion compound by weight. In some embodiments, the intestinal tissue models of the present disclosure contain less than 1% extrusion compound by weight. In some embodiments, the epithelial bio-ink is free from hydrogel. In some embodiments, the epithelial bio-ink is free from extrusion compound. In some embodiments, the epithelial bio-ink is free from synthetic polymers that are used as excipient or extrusion compounds. In some embodiments, the intestinal tissue model is free from synthetic polymers that are used as excipient or extrusion compounds. In some embodiments, the epithelial cell layer is free from synthetic polymers that are used as excipient or extrusion compounds. In some embodiments, the interstitial cell layer is free from synthetic polymers that are used as excipient or extrusion compounds.

Print Surfaces

Provided herein are intestinal tissue models that are attached to a biocompatible surface. In certain embodiments, the interstitial tissue layer is printed onto a biocompatible surface. In certain embodiments, the biocompatible surface is a membrane with a pore size of 0.4 µm to 10 µm. In certain embodiments, the biocompatible surface has a pore size of about 1 μm. In one embodiment, the biocompatible surface comprises polytetrafluoroethylene membrane with pores of 3 μm in size.

In certain embodiments, the biocompatible surface is coated with a composition to improve cell adherence or viability. In certain embodiments, the intestinal tissue modules are printed into 6-well, 12-well, 24-well, 48-well, 96-well, 384-well or 1546-well plates. In certain embodiments, the intestinal tissue modules are printed into tissue culture plates with diameters of 60, 100 or 150 mm or more. In such embodiments, the surface area of the intestinal tissue model may be as large as the diameter of the wells of the tissue culture places. In certain embodiments, the intestinal tissue modules are printed into tissue culture flasks or onto microfluidic chips. In certain embodiments, the intestinal tissue models are printed into/onto Transwell inserts.

In certain embodiments, the intestinal tissue model is cultured in culture medium under static conditions, e.g., in the wells of tissue culture places. In another embodiment, the intestinal tissue model is cultured under non-static, e.g., flow conditions.

In certain embodiments, the intestinal tissue model has a planar surface. In other embodiments, the surface of the intestinal tissue model is non-planar. In other embodiments the surface of the intestinal tissue model is a hydrogel or scaffold material. In other embodiments, the surface of the intestinal tissue model comprises bioprinted tissue. In other embodiments, the surface of the intestinal tissue model is a cell monolayer.

Process for Production of Intestinal Tissue Models

This disclosure provides methods and processes for fabricating intestinal tissue models. In certain embodiments, the product of a three-dimensional, engineered, biological intestinal tissue model is produced by the process of bioprinting. In certain embodiments, at least one constituent of the product of a three-dimensional, engineered, biological intestinal tissue model is produced by the process of bioprinting. In certain embodiments, the process of fabricating a three-dimensional, engineered, biological intestinal tissue model, comprises: preparing an intestinal interstitial bio-ink comprising myofibroblasts; preparing an intestinal epithelial bio-ink; depositing the intestinal interstitial myofibroblast bio-ink and the intestinal epithelial bio-ink such that the intestinal epithelial bio-ink forms a layer on at least one surface of the layer of intestinal interstitial myofibroblast bio-ink; and maturing the deposited bio-inks in a cell culture media to allow the cells to cohere to form the three-dimensional, engineered, biological intestinal tissue model. In certain embodiments, the intestinal interstitial myofibroblast tissue bio-ink forms a tissue layer with an apical and basolateral surface. In certain embodiments, the intestinal epithelial bio-ink is deposited in contact with the apical surface of the intestinal interstitial myofibroblast tissue layer. In certain embodiments, the intestinal epithelial bio-ink consists essentially of intestinal epithelial cells.

In one embodiment, continuous deposition is utilized to produce single or multiple layers mimicking the mucosa and/or epithelium. Additional layers can be printed by continuous deposition to model the submucosa, muscularis, and serosa. Methods of bioprinting include ink-jet deposition, extrusion, microsolenoid deposition (MSV), and biodispense approaches can also be used to add layers, cellular and/or matrix, with more refined resolution as thin a one cell layer. A spray approach could also be used in combination with other approaches to embed cellular material into a printing surface, tissue, or matrix material. Bioprinting provides an advantage to current in vitro gut models in that it enables cells to be placed within a precise geometry, and enables the use of multiple bioink formulations including but not limited to Novogel 2.0, 3.0 and collagen. Continuous deposition can incorporate various biomaterials into the Novogel formulation and various printing surfaces to promote matrix production and differentiation. The printing method utilizes various printing surfaces with various pore sizes that can be coated with matrix support material such as collagen. For example, continuous deposition may be used to print a layered tissue onto a collagen-coated printing surface. Hydrogels can also be added to support biomaterials or constitute space-reserving regions in which there are no cells.

In certain embodiments, the intestinal epithelial bio-ink consists essentially of primary intestinal epithelial cells. In certain embodiments, the primary intestinal epithelial cells are isolated from non-diseased tissues. In certain embodiments, the cells used to make the intestinal tissue constructs (e.g., primary intestinal epithelial cells, myofibroblasts, immune cells, endothelial cells, etc.) are isolated from a subject with a disease that affects intestinal function, e.g., celiac disease. Crohn's disease, ulcerative colitis, irritable bowel syndrome, hemorrhoids, diverticulitis, inflammatory bowel disease, microscopic colitis, lymphocytic colitis, collagenous colitis, endocrine disorders, metabolic disorders, obesity, diabetes, dyslipidemia, colorectal cancer, among others. In certain embodiments, the primary intestinal epithelial cells and/or myofibroblasts are isolated from a subject with celiac disease. In certain embodiments, the primary intestinal tissue epithelial cells and/or myofibroblasts are isolated from a subject with Crohn's disease. In certain embodiments, the primary intestinal tissue epithelial cells and/or myofibroblasts are isolated from a subject with ulcerative colitis. In certain embodiments, the primary intestinal tissue epithelial cells and/or myofibroblasts are isolated from a subject with irritable bowel syndrome. In certain embodiments, the primary intestinal tissue epithelial cells and/or myofibroblasts are isolated from a subject with hemorrhoids. In certain embodiments, the primary intestinal tissue epithelial cells and/or myofibroblasts are isolated from a subject with diverticulitis. In certain embodiments, the primary intestinal tissue epithelial cells and/or myofibroblasts are isolated from a subject with inflammatory bowel disease. In certain embodiments, the primary intestinal tissue epithelial cells and/or myofibroblasts are isolated from a subject with microscopic colitis. In certain embodiments, the primary intestinal tissue epithelial cells and/or myofibroblasts are isolated from a subject with lymophocytic colitis. In certain embodiments, the primary intestinal tissue epithelial cells and/or myofibroblasts are isolated from a subject with collagenous colitis. In certain embodiments, the primary intestinal tissue epithelial cells and/or myofibroblasts are isolated from a subject with an endocrine disorder. In certain embodiments, the primary intestinal tissue epithelial cells and/or myofibroblasts are isolated from a subject with a metabolic disorder. In certain embodiments, the primary intestinal tissue epithelial cells and/or myofibroblasts are isolated from a subject with obesity. In certain embodiments, the primary intestinal tissue epithelial cells and/or myofibroblasts are isolated from a subject with diabetes. In certain embodiments, the primary intestinal tissue epithelial cells and/or myofibroblasts are isolated from a subject with dyslipidemia. In certain embodiments, the primary intestinal tissue epithelial cells and/or myofibroblasts are isolated from a subject with colorectal cancer.

In certain embodiments, the intestinal epithelial cell lines are obtained from commercial sources such as ATCC, Creative Bioarray, and Lonza, include Caco-2, HT-29, HT29-18N2, and HuTu80 cell lines, HIEC-6 (normal), FHs 74 Int (normal), Clonetics™ Intestinal Epithelial Cells (Lonza's primary Intestinal Epithelial Cells), and Human Small Intestinal Epithelial Cells (from Creative Bioarray).

In certain embodiments, the intestinal myofibroblast cell lines are obtained from commercial sources such as ATCC, Creative Bioarray and Lonza.

In certain embodiments, the bio-ink further comprises immune cells. In certain embodiments, the bio-ink comprises lymphoid cells, white blood cells, peripheral blood mononuclear cells (PBMC), neutrophils, T-cells, and B-cells. The immune cells may be primary immune cells from a patient biopsies or cell lines. In certain embodiments, immune cell lines are obtained from commercial sources such as Creative Bioarray, PrecisionForMedicine, BioreclamationIVT, and Lonza, etc.

In certain embodiments, the bio-ink further comprises specialized intestinal epithelial cells such as enterocytes, goblet cells, enteroendocrine cells, paneth cells, microfold cells, cup cells and/or tuft cells. In certain embodiments, specialized intestinal epithelial cell lines are obtained according to methods known in the art. In other embodiment, the specialized cells are obtained from companies that isolate such cells on a contract basis.

In certain embodiments, one or more of the bio-inks comprise intestinal carcinoma cells. In certain embodiments, the intestinal epithelial bio-ink comprises intestinal sarcoma cells. In certain embodiments, the intestinal epithelial bio-ink comprises intestinal lymphoma cells. In certain embodiments, the intestinal epithelial bio-ink comprises intestinal adenocarcinoma cells. The cells may be primary cells from patient biopsies or cell lines. In certain embodiments, carcinoma, sarcoma, lymphoma, and adenocarcinoma cells lines are obtained from commercial sources such as ATCC.

In certain embodiments, one or both bio-inks may further comprise specialized cells such as neuronal cells. In certain embodiments, neuronal cell lines are obtained from commercial sources such as Creative Bioarray.

In certain embodiments, one or both bio-inks may further comprise specialized cells such as endothelial cells. In certain embodiments, neuronal cell lines are obtained from commercial sources such as ATCC®.

In certain embodiments, one or both bio-inks may further comprise specialized cells such as smooth muscle cells. In certain embodiments, neuronal cell lines are obtained from commercial sources such as ATCC®.

In certain embodiments, one or both bio-inks may further comprise specialized cells that may be obtained by directed differentiation of stem cell populations. The stem cell populations may be primary isolates or those which are commercially available, e.g., from ATCC. In one embodiment, the stem cells are iPS cells which are available commercially from Lonza, StemGent and iXCells.

In certain embodiments, the epithelial cells are primary cells from diseased donors, e.g., subjects having celiac disease, Crohn's disease, ulcerative colitis, irritable bowel syndrome, hemorrhoids or diverticulitis. Intestinal tissue constructs with cells from diseased donors may be used in models of the respective diseases. These disease models may be used to test candidate therapeutic treatments for efficacy in the treatment of the respective diseases.

In certain embodiments, the intestinal epithelial bio-ink is deposited in a monolayer. In certain embodiments, the interstitial myofibroblast tissue bio-ink is deposited in a monolayer. In certain embodiments, the bio-ink further comprises an extrusion compound. In certain embodiments, the layer of intestinal epithelial tissue is deposited in continuous contact with the layer of intestinal interstitial myofibroblast tissue. In certain embodiments, the intestinal epithelial bio-ink forms a layer that covers between 50%-100% of the apical surface of the layer of intestinal interstitial myofibroblast tissue. In certain embodiments, the intestinal epithelial bio-ink forms a layer that covers between 70%-100% of the apical surface of the layer of intestinal interstitial myofibroblast tissue. In certain embodiments, the epithelial bio-ink forms a layer that covers between 90%-100% of the apical surface of the layer of the intestinal interstitial myofibroblast tissue. In certain embodiments, the intestinal epithelial bio-ink forms a layer that covers 50-90% the apical surface of the layer of intestinal interstitial myofibroblast tissue.

In certain embodiments, the intestinal tissue model is between 50 and 500 µm thick. In certain embodiments, the intestinal tissue model is about 100 µm thick. In certain embodiments, the intestinal epithelial bio-ink further comprises an extrusion compound. In certain embodiments, the myofibroblasts and epithelial cells are present in a bio-ink at a ratio of about 95:5 to about 5:95 myofibroblasts to epithelial cells. In certain embodiments, the myofibroblasts and epithelial cells are present in a bio-ink at a ratio of about 75:25 to about 25:75 myofibroblasts to epithelial cells. In certain embodiments, the myofibroblasts and epithelial cells are present in the bio-ink at a ratio of about 60:40 to about 40:60 myofibroblasts to epithelial cells. In certain embodiments, the myofibroblasts and epithelial cells are present in the bio-ink at a ratio of about 50:50 myofibroblasts to epithelial cells. In certain embodiments, the bio-ink further comprises secretory cells.

In certain embodiments, the model is fabricated substantially free of pre-formed scaffold. In certain embodiments, the myofibroblasts and epithelial cells are mammalian cells. In certain embodiments, either of the myofibroblast bio-ink or epithelial bio-ink forms a planar layer after deposition. In certain embodiments, the intestinal tissue model is of a uniform thickness. In certain embodiments, the myofibroblast bio-ink is deposited onto a biocompatible membrane. In certain embodiments, the myofibroblast bio-ink is deposited onto a biocompatible membrane with a pore size greater than 0.4 µm. In certain embodiments, the myofibroblast bio-ink is deposited onto a biocompatible membrane with a pore size of about 1 um. In certain embodiments, the three-dimensional, engineered, biological intestinal tissue models are deposited to form an array.

In certain embodiments, the myofibroblast bio-ink is between 30%-100% living cells by volume. In certain embodiments, the myofibroblast bio-ink is between 70%-100% living cells by volume. In certain embodiments, the myofibroblast bio-ink is between 90%-100% living cells by volume. In certain embodiments, the myofibroblast bio-ink is deposited by extrusion bioprinting. In certain embodiments, the epithelial bio-ink is deposited by ink-jet bioprinting. In certain embodiments, the myofibroblast bio-ink is not deposited by ink-jet bioprinting. In certain embodiments, any layer of the intestinal tissue model is viable in in vitro culture in culture after 3 days. In certain embodiments, any layer of the intestinal tissue model is viable in in vitro culture after 10 days.

In certain embodiments, the 3D intestinal tissue models disclosed herein are produced by an additive manufacturing process. The additive manufacturing process for 3D intestinal tissue models herein allows customized fabrication of 3D intestinal tissue models for in vitro purposes. This is significant in that the tissues are fabricated due to a user specified design. In certain embodiments, the 3D intestinal tissue models contain only the cells that the user specifies. In certain embodiments, the 3D intestinal tissue models contain only the cell types that the user specifies. In certain embodiments, the 3D intestinal tissue models contain only the number of cells or concentration of cells that the user specifies. In certain embodiments, the 3D intestinal tissue models contain cells that have been treated with a small molecule, therapeutic molecule, or therapeutic substance before or during fabrication. A therapeutic molecule or substance being any molecule intended to treat a disease or elicit a biological response. In certain embodiments, the 3D intestinal tissue models contain biocompatible or tissue culture plastics, biocompatible synthetic polymers, cross linkable gels, reversibly cross-linked gels and other non-cellular constituents.

Maturation of Intestinal Tissue Models

In certain embodiments, the intestinal tissue models of the present disclosure are matured for a certain amount of time after bioprinting. In certain embodiments, the models are matured for 1-24 hours before use, for example, at least 1, 2, 3, 4, 5, 6, 7, 8, 9, 10, 11, 12, 16, 18, 24 hours or more before use. In certain embodiments, the models are matured for 1-30 days before use, for example, at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 days or more before use. In some embodiments, shipment or transfer of the tissues is a use. In certain embodiments, the interstitial myofibroblast layer of the intestinal tissue model of the present disclosure is matured for a certain amount of time after bioprinting before addition of the epithelial layer. In certain embodiments, the interstitial myofibroblast layer is matured for 1-24 hours before use, for example, at least 1, 2, 3, 4, 5, 6, 7, 8, 9, 10, 11, 12, 16, 18, 24 hours or more before use. In certain embodiments, the interstitial myofibroblast layer is matured for 1-30 days before use, for example, at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 days or more before use. In some embodiments, shipment or transfer of the tissues is a use. In some embodiments, the epithelial layer is bioprinted onto the interstitial myofibroblast layer immediately after bioprinting of the interstitial myofibroblast layer or, for example, 1, 2, 3, 4, 5, 6, 7, 8, 9, 10, 11, 12, 16, 18, 24 hours after bioprinting of the interstitial myofibroblast layer. In some embodiments, shipment or transfer of the tissues is a use. In some embodiments, the epithelial layer is bioprinted onto the interstitial myofibroblast layer within 1-30 days after bioprinting of the interstitial myofibroblast layer, for example 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 days after bioprinting of the interstitial myofibroblast layer.

In some embodiments, the intestinal tissue models are matured in cell culture media under static conditions with or without replacement of the cell culture media on a defined schedule. In other embodiments, the intestinal tissue models are matured in cell culture media under non-static conditions. Non-static conditions include flow of cell culture media across the apical and/or basolateral surface of the intestinal tissue model.

Any mammalian tissue culture media may be used to culture the intestinal tissue models. Examples include BGJb, BME, Brinster's BMOC-3, CMRL, CO2-Independent Medium, DMEM Media, DMEM\F-12 Media, F-10 Nutrient Mixture, F-12 Nutrient Mixture, Glasgow (G-MEM), Improved MEM, Iscove's (IMDM), Leibovitz's L-15, McCoy's 5A, MCDB 131, Media 199, Minimum Essential Media (MEM). Modified Eagle Medium (MEM), Opti-MEM® I, Fischer's Medium, MEM Rega-3, NCTC-135 Medium, RPMI Medium 1640, Waymouth's MB 752/1, and Williams' Media E (ThermoFisher Scientific, Grand Island, New York).

Uses of the Tissue Constructs

The intestinal tissue constructs described herein can be utilized for multiple applications. In one embodiment, the tissue barrier can be utilized for toxicology and ADME applications. In one embodiment, functional features of the tissue constructs include establishment of a barrier and demonstrating permeability/absorption (as evidenced by TEER and Lucifer yellow permeability). These features allow for permeability kinetics (Papp) and influx/efflux (ab, ba) studies. In another embodiment, the investigation of active transport and metabolism via key transporters and metabolic enzymes respectively can be performed via well-based assays or through detection of substrates and their metabolites by mass spectrometry. These same techniques can be used to assess the mechanism of active transport and metabolism of various drugs and applied compounds. Transport kinetic, efflux rate and the permeability coefficient of a test substance could therefore be utilized for correlation to FDA-recommended reference drugs. Through barrier function and permeability kinetics, the tissue constructs may be used to predict the absorption of orally delivered compounds or predict whether there is active transport of compounds via intestinal transporters similar to native tissue, predict the ability of compounds to disrupt the intestinal barrier and/or induce intestinal inflammation, and/or predict the efficacy of compounds to modulate inflammation. In another embodiment, mucosal barrier development and effects of applied compounds on barrier function may also be assessed by mucus secretion (by detecting MUC2). In another embodiment, lipid metabolism, absorption, and transport may be modeled by detecting chylomicron secretion (e.g., via apoB-48 ELISA) and triglyceride synthesis ($^{13}C$ oleate, D20) as endpoints. In another embodiment, enteroendocrine function may be evaluated by detection of gut peptides secretion in response to nutrient stimulation (e.g., GLP-1, PYY, CCK, and/or SST). Movement or response to movement such as peristalsis can be modeled with addition of a flow component, flow or cell-based movement, and/or through the addition of other cell types like smooth muscle cells and neurons.

A major application of the tissue constructs disclosed herein comprising immune cells is the modeling of inflammation and inflammatory diseases, as well as the impact of immune modulation on cancer. In one embodiment, the immune cells are myeloid or lymphoid cells. In another embodiment, the disease models are compared side by side to normal tissue models, e.g., intestinal tissue models lacking immune cells, comprising immune cells but not stimulated to activate the immune cells (quiescent), or lacking immune cells and stimulated with cytokines to mimic an immune response. In this embodiment, the tissue constructs are useful for evaluation of inflammation and immune responses to diseases such as inflammatory bowel disease (IBD), ulcerative colitis, and Crohn's disease. Tissue constructs comprising immune cells may also be used to study acute responses, for example enteritis, or chronic responses such as inflammatory bowel disease. Tissue constructs comprising immune cells may also be used to model injury and recovery including acute, subchronic, or chronic dosing of candidate pharmaceutical compounds or therapies. In another embodiment, the tissue constructs comprising immune cells are used to evaluate wound healing and fibrosis. Fibrotic scar formation, for example, is a common complication of IBD, ulcerative colitis and Crohn's disease, but is much more prevalent in Crohn's disease. Furthermore, the tissue constructs comprising immune cells may be used to modeling microbial/microbiome interactions (pathenogenic microbes like *Clostridium Difficile* or commensal bacteria), or intestinal infection (bacterial or viral). The 3D nature of the tissue constructs allow for enhanced observation of pathogen invasiveness and translocation. The tissue constructs comprising immune cells may be stimulated by cytokines (e.g. IL-17), bacterial components or products, chemical disruption to generate a wound (e.g. dextran sodium sulfate induced colitis), physical disruption (e.g. scraping) that models intestinal injury, or chemical disruption (e.g. 2,4,6-Trinitrobenzene sulfonic acid induced IBD). In one embodiment, the tissues are treated subsequently with candidate pharmaceutical agents or treatments to reverse or control the inflammatory effects. In one embodiment, the impact of antagonists, such as anti-TNF alpha, is followed for correction of injured phenotype. Inflammatory signals that may be detected include the release of cytokines (e.g. IL-8, TNF alpha, IL-4, IL-19, IL-13, IL-17, and/or IFN-gamma), antimicrobial peptides (e.g. beta defensin, lysozymes, and/or sIgA), endocrine products such as somatostatin, activation of inflammatory pathways (e.g. JAK/STAT, and/or NFkB), evaluation of a barrier disruption in response to inflammation (histology, TEER, Lucifer yellow, Ussing chamber, and/or other well-based assays), evaluation of mucus secretion or gene regulation or loss of goblet cells, evaluating the impact on homeostatic epithelial regulation, ion, nutrient and water transport, bile reabsorption, measuring proliferation, cytotoxicity, tissue damage, or apoptosis (Caspase 8 or Tunel) or autophagy or re-epithelialization of wounded area, and expression of key markers and receptors upregulated in response to stimulation (TLRs, Myd99, HNF4alpha, MLCK, Muc2, TFF3). For any of the phenotypes described, the 3D intestinal models may be used to demonstrate the kinetics and magnitude of onset as well as recovery from perturbation. For example, one can dose the tissues with a therapeutic agent and measure the kinetics of absorption in parallel with the kinetics of onset of tissue damage, and then remove the test agent and measure the kinetics of clearance of the molecule in the tissue and of recovery from damage. Analysis of these parameters may enable the prediction of appropriate dosing levels and dosing schedule for compounds entering the clinic.

The intestinal tissue models may also be used in a method of assessing the ability of a candidate therapeutic agent to reverse, reduce, induce or prevent an intestinal disorder or injury, the method comprising:
(a) contacting the intestinal tissue model or the non-human animal model with the candidate therapeutic agent, wherein the intestinal tissue model has a phenotype of an intestinal disorder or injury;
(b) determining the viability or functionality of the intestinal tissue cells; and
(c) assessing the ability of the candidate therapeutic agent to reverse, reduce or prevent an intestinal disorder or injury based on the determined viability or functionality of the intestinal tissue cells compared to a control intestinal tissue model that has not been contacted with the candidate therapeutic agent.

In some embodiments, the phenotype of an intestinal disorder or injury is induced by contacting the intestinal tissue model with a treatment, compound, or infectious agent that gives rise to the phenotype. In some embodiments, the phenotype of an intestinal disorder or injury is the presence of tumor(s), tumor fragment(s), tumor cells, or immortalized cells in the intestinal tissue model. In some embodiments, the ability of a candidate therapeutic agent to reverse, reduce, induce or prevent an intestinal disorder or injury is reduced tumor(s), tumor fragment(s), tumor cells, or immortalized cells invasion or metastasis.

The intestinal tissue models may also be used in a method of assessing the ability of a candidate therapeutic agent to reverse, reduce, induce or prevent an intestinal disorder or injury, the method comprising:
(a) contacting the intestinal tissue model or the non-human animal model with the candidate therapeutic agent;
(b) determining the viability or functionality of the intestinal tissue cells; and
(c) assessing the ability of the candidate therapeutic agent to reverse, reduce or prevent an intestinal disorder or injury based on the determined viability or functionality of the intestinal tissue cells compared to a control intestinal tissue model that has not been contacted with the candidate therapeutic agent.

In one embodiment, the phenotype of an intestinal disorder or injury is induced by contacting the intestinal tissue model with a treatment, compound, or infectious agent that gives rise to the phenotype. Examples of such treatments include radiation treatment and physical injury. Examples of compounds include any compounds known to be injurious to intestinal tissue including NSAIDs such as aspirin, ibuprophen, naproxen sodium, celecoxib, diclofenac, diflunisal, etodolac, fenoprofen, flurbiprofen, indomethacin, ketoprofen, ketorolac, mefenamic acid, meloxicam, nabumetone, oxaprozin, piroxicam, sulindac and tolmetin. Examples of infectious agents include *salmonella, Staphylococcus aureus, Bacillus cereus, clostridium, campylobacter, Yersinia, vibrio, Giardia lamblia*, intestinal worms, and *Clostridium difficile*.

In some embodiments, the impact of candidate chemotherapy or immune modulating agents may be investigated. In some embodiments, the intestinal tissue model comprises tumor cells and a candidate therapeutic agent or immune modulator for the treatment of the tumor is contacted with the intestinal tissue model.

In other embodiments, the intestinal tissue model is used in a method to study the microbiome of the intestine by contacting the intestinal tissue model with organisms of the intestinal microbiome and determining the viability or functionality of the intestinal tissue cells compared to a control intestinal tissue model that has not been contacted with the organisms. In one embodiment, the intestinal tissue model comprises diseased intestinal tissue cells. In other embodiments, the intestinal tissue model comprises normal intestinal tissue cells. In further embodiments, the intestinal tissue models are contacted with candidate therapeutic agents or treatments to evaluate the impact of the therapeutic agents or treatments on the intestinal microbiome.

In some embodiments, the intestinal tissue models and arrays disclosed herein are for use in in vitro assays. In some embodiments, an "assay" is a procedure for testing or measuring the presence or activity of a substance (e.g., a chemical, molecule, biochemical, drug, etc.) in an organic or biologic sample (e.g., cell aggregate, tissue, organ, organism, etc.). In further embodiments, assays include qualitative assays and quantitative assays. In still further embodiments, a quantitative assay measures the amount of a substance such as a chemical or biomolecule in a sample.

In various embodiments, the intestinal tissue models and arrays are for use in, by way of non-limiting example, image-based assays, measurement of secreted proteins, expression of markers, and production of proteins or mRNAs. In various further embodiments, the intestinal tissue models and arrays are for use in assays to detect or measure one or more of: molecular binding (including radioligand binding), molecular uptake, activity (e.g., enzymatic activity and receptor activity, metabolite production etc.), gene expression, protein expression, protein modifications (non-limiting examples include: phosphorylation, ubiquitination, acetylation, glycosylation, lipidation, etc.), receptor agonism, receptor antagonism, cell signaling, apoptosis, chemosensitivity, transfection, cell migration, chemotaxis, cell viability, cell proliferation, safety, efficacy, metabolism, toxicity, infectivity, immune activation, immune modulation, and abuse liability. In various embodiments, the intestinal tissue models are for toxicology, pharmaceutical or toxicity testing.

In some embodiments, the intestinal tissue models and arrays are for use in immunoassays. Immunoassays include, for example, flow cytometry, high throughput or low throughput image analysis, immunoprecipitation, radio-immunoassay (RIA), enzyme-linked immunosorbent assays (ELISA), western blot, homogenous assays, such as AlphaLISA™ and related technologies that rely on time resolved fluorescence or fluorescence resonance energy transfer (FRET). In further embodiments, immunoassays are competitive immunoassays or noncompetitive immunoassays. In a competitive immunoassay, for example, the antigen in a sample competes with labeled antigen to bind with antibodies and the amount of labeled antigen bound to the antibody site is then measured. In a noncompetitive immunoassay (also referred to as a "sandwich assay"), for example, antigen in a sample is bound to an antibody site; subsequently, labeled antibody is bound to the antigen and the amount of labeled antibody on the site is then measured.

In some embodiments, the intestinal tissue models and arrays are for use in ELISA. In further embodiments, an ELISA is a biochemical technique used to detect the presence of an antibody or an antigen in a sample. In ELISA, for example, at least one antibody with specificity for a particular antigen is utilized. By way of further example, a sample with an unknown amount of antigen is immobilized on a solid support (e.g., a polystyrene microtiter plate) either non-specifically (via adsorption to the surface) or specifically (via capture by another antibody specific to the same antigen, in a "sandwich" ELISA). By way of still further example, after the antigen is immobilized, the detection antibody is added, forming a complex with the antigen. The detection antibody is, for example, covalently linked to an enzyme, or is itself detected by a secondary antibody that is linked to an enzyme through bioconjugation.

In other embodiments, the intestinal tissue models are subject to mass spectrometry analysis to determine the components of the intestinal tissue models. Such components include metabolites of candidate therapeutic treatments, proteins, cytokines, RNA, DNA, and the like.

For example, in some embodiments, an array, microarray, or chip of cells, multicellular aggregates, or tissues is used for drug screening or drug discovery. In further embodiments, an array, microarray, or chip of tissues is used as part of a kit for drug screening or drug discovery. In some embodiments, each intestinal tissue model exists within a well of a biocompatible multi-well container, wherein the container is compatible with one or more automated drug screening procedures and/or devices. In further embodiments, automated drug screening procedures and/or devices include any suitable procedure or device that is computer or robot-assisted.

In further embodiments, arrays for drug screening assays or drug discovery assays are used to research or develop drugs potentially useful in any therapeutic area. In still further embodiments, suitable therapeutic areas include, by way of non-limiting examples, infectious disease, hematology, oncology, pediatrics, gastroenterology, pain control, vaccines, wound healing, physiology, pharmacology, gene therapy, toxicology, toxicity, and immunology.

In some embodiments, the intestinal tissue models and arrays are for use in cell-based screening. In further embodiments, the cell-based screening is for one or more infectious diseases such as viral, fungal, bacterial or parasitic infection. In further embodiments, the cell-based screening is for colon cancer.

In some embodiments, the constructs or arrays thereof are for use in assessing the performance of biologics, including antibodies, mammalian cells, bacteria, biologically-active proteins, hormones, peptides, small molecules etc. In other embodiments, the intestinal tissue models or arrays thereof are useful in the study of cell-cell and cell-tissue interactions between the mammalian intestinal tissue models comprising the construct and one or more additional cell types, including but not limited to pathogen-bearing cells, living pathogenic cells, cancer cells, immune cells, blood cells, stem/progenitor cells, or genetically-manipulated cells.

In some embodiments, the array comprises intestinal tissue models and additional tissue constructs. In further embodiments, the intestinal tissue construct is in direct contact with an additional tissue construct on one or more surfaces. In still further embodiments, the intestinal tissue model is connected to one or more additional tissues constructs or cells via a fluid path or common fluid reservoir. In still further embodiments, the liquid media that contacts the engineered intestinal tissue construct contains living mammalian cells such as immune cells, blood-derived cells, or tumor-derived cells. In other embodiments, the liquid media that contacts the intestinal tissue contains an infectious agent such as bacteria, fungi, viruses, parasites, or other pathogens.

In certain embodiments, the three-dimensional, engineered, bioprinted, biological intestinal tissue model comprises a layer of intestinal interstitial myofibroblasts and a layer of intestinal epithelial tissue. In other embodiments, at least one of the layer of intestinal interstitial myofibroblasts and layer of intestinal epithelial tissue comprises additional cell types such as myeloid cells, lymphoid cells/white blood cells, enteroendocrine cells, goblet cells, Paneth cells, M cells, neuronal cells, smooth muscle cells, endothelial cells specialized cells derived from directed differentiation of iPS cells and/or primary cells or iPS cells from diseased donors (e.g., from subjects having IBD, colitis or Crohn's disease).

In one embodiment, the intestinal tissue construct may be used to test candidate drugs for treating intestinal fibrosis and fibrotic scar formation. Methods for detecting intestinal fibrosis and scar formation are reviewed by, for example, Florian Rieder, Sean Kessler, Miquel Sans, and Claudio Fiocchicorresponding (2012). Animal models of intestinal fibrosis, new tools for the understanding of pathogenesis and therapy of human disease. *Am J Physiol Gastrointest Liver Physiol.* 303(7): G786-G801.

The intestinal tissue construct may also be used in a method of testing candidate therapeutic agents for intestinal wound healing. In this embodiment, the intestinal tissue construct is damaged (e.g., cut, bisected, punched, punctured, abraded, scraped, exposed to a chemical that causes damage, etc.), the damaged tissue construct is treated with the candidate therapeutic agent, and evidence of healing is detected compared to that of a control construct that has not been contacted with the candidate therapeutic agent. In another embodiment, the damaging agent itself is simply removed, and the kinetics and degree of healing is compared to that of a control construct that has not been previously damaged.

The intestinal tissue construct may also be used to model microbial/microbiome interactions (pathogenic or commensal bacteria), and intestinal infection (bacterial or viral).

The intestinal tissue construct may also be used to model peristalsis with the addition of a flow component and/or the inclusion of smooth muscle cells and neurons. In this embodiment, the intestinal tissue construct is subject to flow of media in a bioreactor.

In some embodiments, the intestinal tissue model is at least 2 cell layers thick. In some embodiments, the intestinal tissue model is 2 or more cell layers thick. In some embodiments, where the intestinal epithelial cells do not completely cover the intestinal interstitial tissue, the uncovered interstitial tissue may be as little as one cell layer thick in the uncovered area. Likewise, where the interstitial tissue layer does not completely cover the print surface, the covering intestinal epithelial cell layer may be as little as one cell layer thick on the print surface without the intestinal interstitial tissue.

In some embodiments, the mean thickness of the intestinal tissue model is at least 20 µm. In some embodiments, the mean thickness of the intestinal tissue model is at least 100 µm. In some embodiments, the mean thickness of the intestinal tissue model is at least 200 µm. In some embodiments, the mean thickness of the intestinal tissue model is at least 300 µm. In some embodiments, the mean thickness of the intestinal tissue model is at least 400 µm. In some embodiments, the mean thickness of the intestinal tissue model is at least 500 µm. In some embodiments, the mean thickness of the intestinal tissue model is at least 600 µm. In some embodiments, the mean thickness of the intestinal tissue model is at least 700 µm. In some embodiments, the mean thickness of the intestinal tissue model is at least 800 µm. In some embodiments, the mean thickness of the intestinal tissue model is at least 900 µm. In some embodiments, the mean thickness of the intestinal tissue model is at least 1000 µm. In some embodiments, the mean thickness of the intestinal tissue model is between 50 µm and 3000 µm. In some embodiments, the mean thickness of the intestinal tissue model is between 75 µm and 1000 µm. In some embodiments, the mean thickness of the intestinal tissue model is between 100 µm and 1000 µm. In some embodiments, the mean thickness of the intestinal tissue model is between 200 µm and 1000 µm. In some embodiments, the mean thickness of the intestinal tissue model is between 500 µm and 1000 µm. In some embodiments, the mean thickness of the intestinal tissue model is between 50 µm and 500 µm. In some embodiments, the mean thickness of the intestinal tissue model is between 50 µm and 300 µm. In some embodiments, the mean thickness of the intestinal tissue model is between 50 µm and 200 µm. In some embodiments, the mean thickness of the intestinal tissue model is between 50 µm and 150 µm. In some embodiments, the mean thickness of the intestinal tissue model is between 50 µm and 125 µm. In some embodiments, the mean thickness of the intestinal tissue model is between 75 µm and 100 µm.

In some embodiments, the print surface area is between 0.01 cm$^2$ and 100 cm$^2$. The print surface may be the wells of a microtiter plate which may range from 6 to 384 wells or more. In some embodiments, the print surface area is 2 cm$^2$ for a 24 well plate.

The potential toxic agent is anything that may have an effect on the structure or function of intestinal tissue. In some embodiments, the potential toxic agent is a toxin, a therapeutic agent, an antimicrobial agent, a metal, a microorganism (e.g., bacteria, virus, parasite, fungus), or an environmental agent. In other embodiments, the potential toxic agent is an antiviral, an analgesic agent, an antidepressant agent, a diuretic agent, or a proton pump inhibitor.

In other embodiments, the potential toxic agent is a cytokine, a chemokine, a small molecule drug, a large molecule drug, a protein or a peptide.

In other embodiments, the potential toxic agent is a chemotherapeutic agent which is an aromatase inhibitor; an anti-estrogen; an anti-androgen; a gonadorelin agonist: a topoisomerase I inhibitor: a topoisomerase II inhibitor: a microtubule active agent; an alkylating agent; a retinoid, a carontenoid, or a tocopherol; a cyclooxygenase inhibitor: an MMP inhibitor; an mTOR inhibitor; a receptor tyrosine kinase (RTK) inhibitor, a serine/threonine kinase inhibitor, an antimetabolite: a platin compound; a methionine aminopeptidase inhibitor; a bisphosphonate: an antiproliferative antibody: a heparanase inhibitor: an inhibitor of Ras oncogenic isoforms; a telomerase inhibitor: a proteasome inhibitor; a compound used in the treatment of hematologic malignancies; a Flt-3 inhibitor; an Hsp90 inhibitor; a kinesin spindle protein inhibitor; a MEK inhibitor; an antitumor antibiotic; a nitrosourea; a compound targeting/decreasing protein or lipid kinase activity, a compound targeting/decreasing protein or lipid phosphatase activity, or an anti-angiogenic compound. In other embodiments, the potential toxic agent is a chemotherapeutic agent which is daunorubicin, adriamycin, Ara-C, VP-16, teniposide, mitoxantrone, idarubicin, cisplatin, carboplatinum, PKC412, 6-mercaptopurine (6-MP), fludarabine phosphate, octreotide, SOM230, FTY720, 6-thioguanine, cladribine, 6-mercaptopurine, pentostatin, hydroxyurea, 2-hydroxy-1H-isoindole-1,3-dione derivatives, 1-(4-chloroanilino)-4-(4-pyridylmethyl)phthalazine, 1-(4-chloroanilino)-4-(4-pyridylmethyl)phthalazine succinate, angiostatin, endostatin, anthranilic acid amides, ZD4190, ZD6474, SU5416, SU6668, bevacizumab, rhuMAb, rhuFab, macugon, FLT-4 inhibitors, FLT-3 inhibitors, VEGFR-2 IgGI antibody, RPI 4610, bevacizumab, porfimer sodium, anecortave, triamcinolone, hydrocortisone, 11-α-epihydrocotisone, cortex olone, 17a-hydroxyprogesterone, corticosterone, desoxycorticosterone, testosterone, estrone, dexamethasone, fluocinolone, a plant alkaloid, a hormonal compound and/or antagonist, a biological response modifier, such as a lymphokine or interferon, an antisense oligonucleotide or oligonucleotide derivative, shRNA, siRNA, or a pharmaceutically acceptable salt thereof.

In other embodiments, the potential toxic agent is ibuprofen, acetaminophen, lithium, acyclovir, amphotericin B, and aminoglycoside, a beta lactams, foscavir, ganciclovir, pentamidine, a quinolone, a sulfonamide, vancomycin, rifampin, adefovir, indinavir, didofovir, tenofovir, methotrexate, lansoprazole, omeprazole, pantopraxole, allopurinol, phenytoin, ifosfamide, gentamycin, or zoledronate.

In some embodiments, the potential toxic agent is radiation. In some embodiments, radiation may include X-rays, gamma rays, UV, and others. In some embodiments, radiation is used alone or in combination with another toxic agent or agents. In some embodiments, the radiation may include photon radiotherapy, particle beam radiation therapy, other types of radiotherapies, and combinations thereof.

In some embodiments, the toxic agent is dissolved in a biocompatible solvent. When the potential toxic agent is water insoluble, the potential toxic agent may be dissolved with a polar, aprotic organic solvent such as dimethyl sulfoxide (DMSO) or dimethyl formamide (DMF) and then diluted with a aqueous solution such as 9 g/L sodium chloride (saline), in distilled water, aqueous Tween, culture media, or another biocompatible solvent.

In some embodiments, the toxic agent is a modulator of the immune system. In some embodiments, immune modulators may include toll-like receptor (TLR) agonists like LPS or imiquimod, TLR antagonists, steroids, or checkpoint inhibitors like anti-PD1, anti-PDL1, or anti-CTLA4.

In some embodiments, the viability or functionality of the intestinal epithelial cells is determined by measuring an indicator of metabolic activity. In some embodiments, metabolic activity may be measured by alamarBlue™ Assay (Thermo Fisher, Carlsbad, CA), lactate dehydrogenase (LDH) activity assay, or another assay. In some embodiments, the indicator of metabolic activity is resazurin reduction or tetrazolium salt reduction in the intestinal tissue model compared to a control. In some embodiments, resazurin reduction is measured using the alamar blue assay (Rampersad, S. N., (2012), Multiple applications of alamar blue as an indicator of metabolic function and cellular health in cell viability bioassays. *Sensors* 12(9): 12347-12360). In some embodiments, the tetrazolium salts include 3-(4,5-dimethyethiazol-2-yl)-2, 5-diphenyltetrazolium bromide (MTT); sodium 3'-[1-phenylamino)-carbonyl]-3,4-tetrazolium]-bis (4-methoxy-6-nitrobenzene) sulfonic acid hydrate (XTT); 4-[3-(4-iodophenyl)-2-(4-nitrophenyl)-2H-5-tetrazolio]-1,3-benzene disulfonate, water-soluble tetrazolium salt (WST-1); and others (Rampersad, 2012).

In some embodiments, the viability or functionality of the intestinal epithelial cells is determined by measuring lactate dehydrogenase (LDH) activity, gamma glutamyl-transferase (GGT) activity, protease activity, ATP utilization, ATP level and changes thereto, glucose uptake activity, sodium-glucose co-transporter-1 (SGLT1) activity, secretion of any intestinal specific proteins or peptides, or RNA expression compared to a control. In some embodiment, the viability or functionality of the intestinal epithelial cells is determined by measuring alkaline phosphatase activity or caspase activity. In some embodiments, protease activity is measured by measuring caspase activity using synthetic peptide substrates (Kumar (2004) *Chapter 2: Measurement of caspase activity in cells undergoing apoptosis*. Methods in Molecular Biology, vol. 228. Totowa, NJ: Humana Press Inc). In some embodiments, intracellular ATP is measured using an ATP assay kit (Weng. Z., Patel, A. B., Panagiotidou, S., and Theoharides, T. C. (2015). The novel flavone tetramethoxyluteolin is a potent inhibitor of human mast cells. J Allergy Clin Immunol 135(4), 1044-1052). One commercially available kit for measuring ATP levels is CellTiter-Glo® available from Promega Corporation.

In other embodiments, the viability or functionality of the intestinal epithelial cells is determined by measuring a transport molecule activity in the model compared to a control. In other embodiments, the transport molecule activity is excretion and/or uptake of at least one macromolecule. In other embodiments, the macromolecule is collagen.

In other embodiments, the viability or functionality of the epithelial cells is determined by identifying regeneration of the epithelial cells compared to a control. In one embodiment, regeneration is identified by visually inspecting the epithelial cells and identifying an increase in the number of viable cells.

In other embodiments, the viability or functionality of the epithelial cells is determined by measuring the trans-epithelial electrical resistance (TEER) or the passive permeability of the intestinal tissue model compared to a control.

In other embodiments, the viability or functionality of the intestinal epithelial cells is determined by measuring alterations to ion exchange, alterations to pH, alterations to acid/base balance, alterations to barrier function, or alterations in physiology, alterations in pathology, alterations to transport of molecules, alterations to sodium-glucose cotransporter-1 (SGLT1) activity, amounts of interstitial fibrotic tissue, or regeneration of the intestinal tissue model compared to a control.

In other embodiments, the viability or functionality of the intestinal epithelial cells is determined by measuring amounts of intestinal fibrotic tissue compared to a control. In some embodiments, intestinal fibrotic tissue is measured using Trichrome or Alician blue/PAS fibrosis measurement, collagen III immunohistochemistry, Sirius Red staining, or another type of assay (Farris A. B., Adams C. D., Brousaides N., Della Pelle P. A., Collins A. B., Moradi E., Smith R. N., Grimm P. C., and Colvin R. B. (2011). Morphometric and visual evaluation of fibrosis in renal biopsies. *J Am Soc Nephrol* 22(1), 176-86). In some embodiments, the viability or functionality of the intestinal epithelial cells is measured over time.

In some embodiments, the intestinal tissue model is contacted first with the potential toxic agent and then with the candidate therapeutic agent. In other embodiments, the intestinal tissue model is contacted first with the candidate therapeutic agent and then with the potential toxic agent. In some embodiments, the intestinal tissue model has been cultured in a cell culture medium prior to being contacted with the candidate therapeutic agent and the potential toxic agent. In some embodiments, the intestinal tissue model has been cultured for at least 3 days in the cell culture medium.

Also provided are methods of assessing the effect of an agent on intestinal function, the method comprising contacting the agent with a three-dimensional, engineered, bioprinted, biological intestinal tissue model and measuring the effect of the agent on intestinal function the viability or functionality of the intestinal epithelial cells. In some embodiments, the three-dimensional, engineered, bioprinted, biological intestinal tissue model comprises a layer of myofibroblast tissue; and a layer of epithelial tissue, the epithelial tissue comprising intestinal epithelial cells; provided that the myofibroblast tissue comprises an bio-ink, the epithelial tissue comprises an epithelial bio-ink, and form a three-dimensional, engineered, biological intestinal tissue model.

Also provided is a method of assessing the effect of a potential toxic agent on intestinal function, the method comprising:
(a) contacting the agent with the three-dimensional, engineered, bioprinted, biological intestinal tissue model: and
(b) measuring the effect of the agent on the viability or functionality of the intestinal tissue model cells.

In some embodiments, provided is a method to reverse or reduce injury by a toxic agent, and the intestinal tissue model is contacted first with the toxic agent and then the potential toxic agent is removed.

Also provided is a method of assessing the kinetics of intestinal absorption of an agent, the method comprising:
(a) contacting the agent with the three-dimensional, engineered, bioprinted, biological intestinal tissue model; and
(b) measuring the kinetics of absorption by the intestinal tissue model.

Also provided is method of predicting the effective dosing concentration and dosing schedule of a candidate therapeutic agent, the method comprising:
(a) contacting varying concentrations or amounts of the agent with the three-dimensional, engineered, bioprinted, biological intestinal tissue model; and
(b) measuring the effect of the agent on the viability or functionality of the intestinal tissue model cells over time: and
(c) measuring the recovery of the intestinal tissue model cells over time to determine the minimum timing between doses that provide efficacy.

In some embodiments, the method further comprises:
(d) removing the agent; and
(e) assessing whether the absence of the agent results in improved viability or functionality of the intestinal tissue model.

The disclosure herein includes business methods. In some embodiments, the speed and scalability of the techniques and methods disclosed herein are utilized to design, build, and operate industrial and/or commercial facilities for production of intestinal tissue models for use in cell-based tools for research and development, such as in vitro assays. In further embodiments, the intestinal tissue models and arrays thereof are produced, stored, distributed, marketed, advertised, and sold as, for example, cellular arrays (e.g., microarrays or chips), tissue arrays (e.g., microarrays or chips), and kits for biological assays and high-throughput drug screening. In other embodiments, the engineered intestinal tissue models and arrays thereof are produced and utilized to conduct biological assays and/or drug screening as a service.

Validation

The ideal engineered intestinal tissue models are fully human and multicellular, comprising intestinal epithelial cells and intestinal myofibroblasts, and optionally additional cells such as myeloid cells. Moreover, engineered intestinal tissues manifest one or more of the following characteristics:

Correct tissue structure as evidenced by H&E staining showing bi-layered structure.
Immunohistochemistry for epithelial cell markers (CK19), myofibroblast markers (vimentin), and myeloid cell markers (CD14, CD68 and CD206) as well as markers of any other specialized cell type incorporated into the tissue such as lymphoid immune cells (CD4, CD8, CD19, etc.), endothelial cells (CD31) or neurons.
Barrier function as evidenced by well-based TEER studies and/or permeability/adsorption by Lucifer yellow.
Cytokine production (e.g. IL-1, IL-6 and TNFα measured, e.g., by ELISA).
Epithelial tight junction formation (e.g. E-Cadherin, ZO-1), brush border formation (villin), key transporter expression (e.g. P-gp/MDR1, BCRP), and basement membrane formation (e.g. collagen IV).
Transporter/metabolic enzyme activity (e.g.: P-gp and CYP3A4).
Inducible cytokine production following stimulation (e.g., with LPS).
Sustainability in culture and viability (e.g. histology, MTT or Alamar Blue).
Mucus production (e.g. MUC2, e.g. by ELISA), presence of goblet cells.
Endocrine peptide secretion (e.g. GLP-1, PYY, CCK), presence of enteroendocrine cells.
Lipid absorption/transport (e.g. chylomicron secretion, apoB-48, e.g., by ELISA), triglyceride synthesis (e.g. $^{13}C$ oleate, $D_2O$).
Fibrotic scar formation by bisecting/cutting/punching/treating with a chemical damage agent identified by immunohistochemistry (IHC) staining in addition to differentiation and migration (e.g. CK19, vimentin).
Inducible collagen or other fibrotic ECM production in response to pro-fibrotic stimulants such as TGF-beta or other fibrogenic compounds (e.g. histology and gene expression).
Induction of inflammation, either acute (e.g., enteritis) or chronic (e.g., IBD). Inflammatory stimulation may include cytokines (e.g., IL-17), bacterial components or products, chemical disruption to generate a wound (e.g., dextran sodium sulfate), physical disruption (e.g., cutting, bisecting, abrading, scraping, puncturing), TLR agonists (e.g. LPS, RNA, imiquimod) or chemical (e.g., use of 2,4,6-trinitrobenzenesulfonic acid to induce a model of IBD).
Release of cytokines (e.g., IL-8, TNF-alpha, IL-4, IL-19, IL-13, IL-17, IFN-gamma), antimicrobial peptides (e.g., beta definsin, lysozymes, sigA), and endocrine products (e.g., somatostatin).
Activation of inflammatory pathways (e.g., JAK/STAT, NFkB).
Barrier disruption in response to inflammation (e.g., by histology, TEER, Lucifer yellow)
Changes in mucus secretion/gene regulation/loss of goblet cells in response to inflammatory stimuli.
Proliferation/apoptosis (e.g, by detecting Caspase 8 or by terminal deoxynucleotidyl transferase dUTP nick end labeling (Tunel) that detects DNA fragmentation).
Upregulation of markers and receptors in response to stimulation (TLRs, Myd99, HNF4alpha, MLCK, Muc2 or TFF3).

In some embodiments, the intestinal models of the present disclosure display increased specific functions compared to 2D co-culture or tissue explants that have been maintained in culture longer than 1, 2, 3, 4, 5, 6, 7, 8, 9, or 10 days or 1, 2, 3, or 4 weeks. In some embodiments, the intestinal tissue models of the present disclosure display 2-fold increased specific functions compared to 2D co-culture or tissue explants that have been maintained in culture longer than 1, 2, 3, 4, 5, 6, 7, 8, 9, or 10 days or 1, 2, 3, or 4 weeks. In some embodiments, the intestinal tissue models of the present disclosure display 5-fold or more increased specific functions compared to 2D co-culture or tissue explants that have been maintained in culture longer than 1, 2, 3, 4, 5, 6, 7, 8, 9, or 10 days or 1, 2, 3, or 4 weeks. In some embodiments, the intestinal tissue models of the present disclosure display 2-fold or more increased specific functions compared to 2D co-culture or tissue explants that have been maintained in culture longer than 14 or more days. In some embodiments, the intestinal tissue models of the present disclosure display 5-fold or more increased specific functions compared to 2D co-culture or tissue explants that have been maintained in culture longer than >14 days. In some embodiments, the intestinal tissue models of the present disclosure display 2-fold or more increased specific functions compared to 2D co-culture or tissue explants that have been maintained in culture longer than 14 or more days. In some embodiments, the intestinal tissue models of the present disclosure display 5-fold or more increased specific functions compared to 2D co-culture or tissue explants that have been maintained in culture longer than 14 or more days.

EXAMPLES

The following illustrative examples are representative of embodiments, of the software applications, systems, and methods described herein and are not meant to be limiting in any way.

Example 1

A Manually Created Three-Dimensional Intestinal Tissue Model

Human intestinal tissue was fabricated with human primary intestinal cells and intestinal cell lines by continuous deposition using interstitial bio-ink containing gelatin and manual deposition of an epithelial suspension.

Bio-ink was generated by a cellular mixture of 100% primary adult human intestinal myofibroblasts (IMF) in 8% gelatin in a concentration of 20 million cells per milliliter. Three-dimensional bioink constructs were printed by continuous deposition using the Novogen MMX Bioprinter®. One tissue was printed per transwell in a 24 well plate. The transwell printing surface contained a polytetrafluoroethylene (PTFE) membrane coated with equimolar mixture of types I and III collagen (bovine) with pores 3 µm in size. Following printing, tissues were allowed to mature for 4 days in a humidified incubator in growth media. Tissues were cultured in 100% IMF media and media was changed daily. After incubation, interstitial tissue constructs were removed from the incubator and placed in a BSC hood. Media was aspirated immediately before application of epithelial cells. Epithelial cells were added as a cell suspension mixture of 75% Caco-2 cells and 25% STC-1 cells. Caco-2 cells are a human colorectal adenocarcinoma epithelial cell line. STC-1 cells are a mouse enteroendocrine intestinal cell line. In some wells no epithelial cells were added to the printed IMF layer and these wells were used as a control for comparison studies. In some wells, epithelial cells were added to an empty transwell with no IMF layer as an additional 2D control. After deposition, media was added to the outer area of the transwell basket. Media was changed daily for up to 18 days. The full culture period was 4 days of IMF interstitial tissue incubation plus 4, 7, or 14 days post addition of epithelial cells. Thus, experiments are labeled as day 4, 7, and 14, which corresponds to a full culture time of 8, 11, and 18 days, respectively.

Experiment time course studies were run 4, 7, and 14 days post addition of epithelial cells. Tissues were measured for GLP-1 secretion into supernatant. Tissues were also measured for barrier function at multiple time points by TEER or Lucifer yellow (non-lytic assays). After incubation, the tissues were fixed in paraformaldehyde (PFA) for histology or lysed for RNA extraction.

Results

Figure 1B:
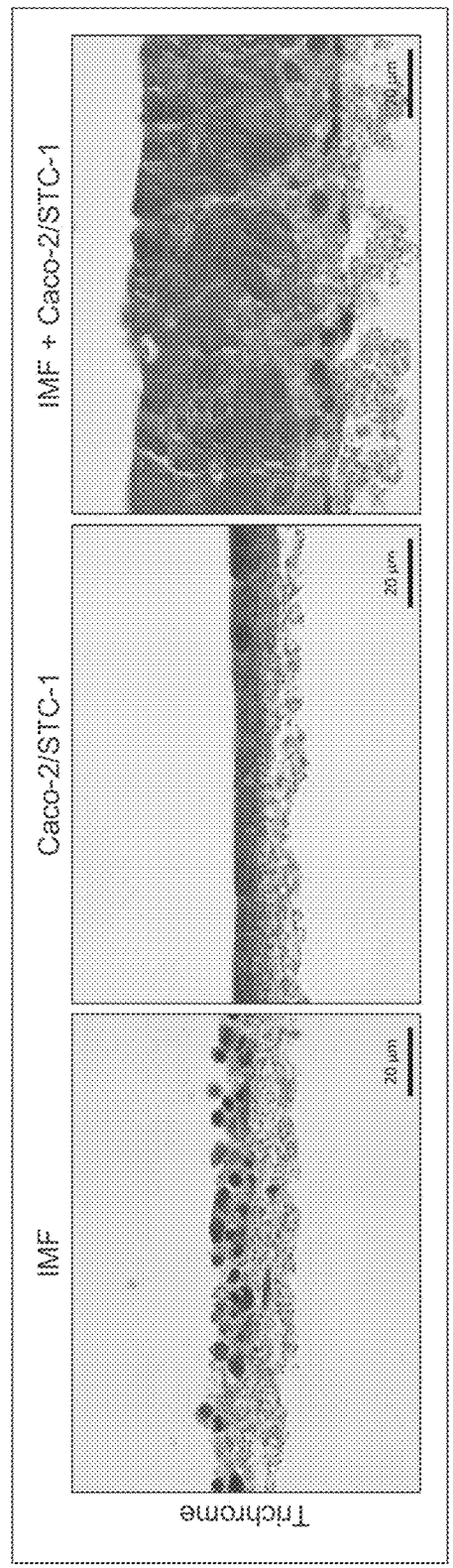

Bioprinted intestinal tissue constructs maintained a cohesive structure after incubation in static media conditions and achieved a bi-layered architecture. Tissues were cross sectioned perpendicular to the plane of the transwell to show the interstitial and epithelial layers. An unexpected finding was that the Caco-2 epithelial layer increased in thickness over time in culture in 3D tissues and this was not observed in 2D monolayer cultures of Caco-2 epithelial cells within the time period studied. The data suggested cross talk between the printed interstitial myofibroblast layer and the epithelial layer that directs differentiation and secondary structure formation of the tissue epithelium. This data suggests a printed interstitial layer is required for tissue thickening and secondary structure formation. In addition, the data suggests that neither flow conditions nor mechanical stimulation are required for appropriate secondary structure formation (FIGS. 1A-1B)

Figure 3A:
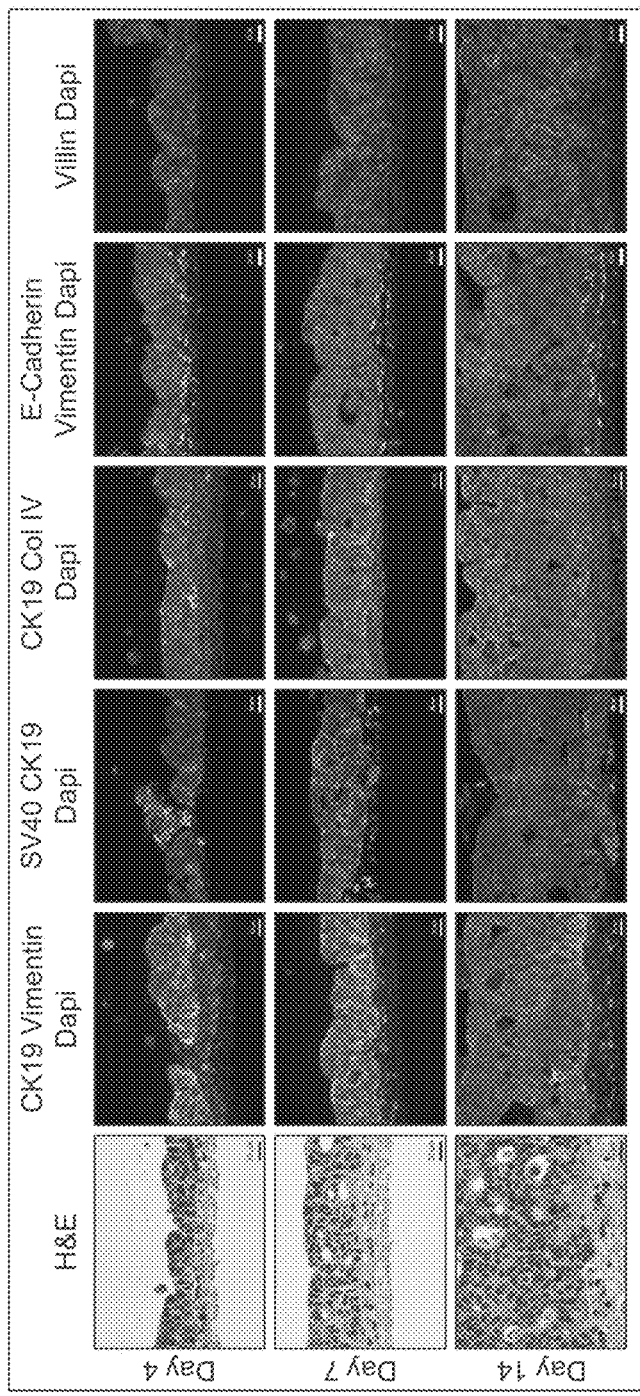
FIGS. 3A-3C are graphs showing bioprinted 3D Caco-2 tissues thicken over time in culture and maintain key architectural features.
Figure 3C:
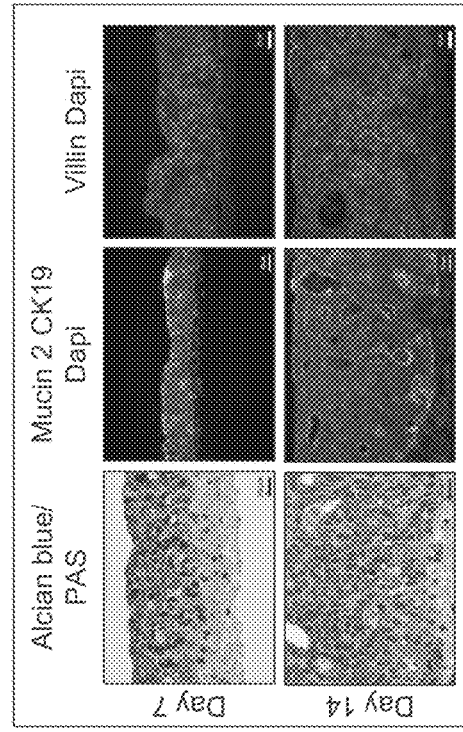
Figure 3B:
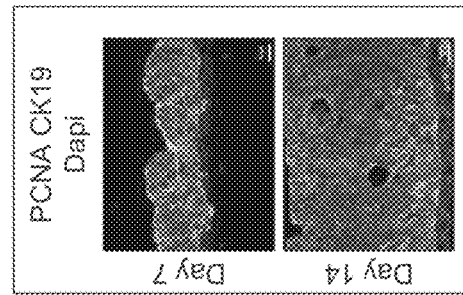
Figure 4:
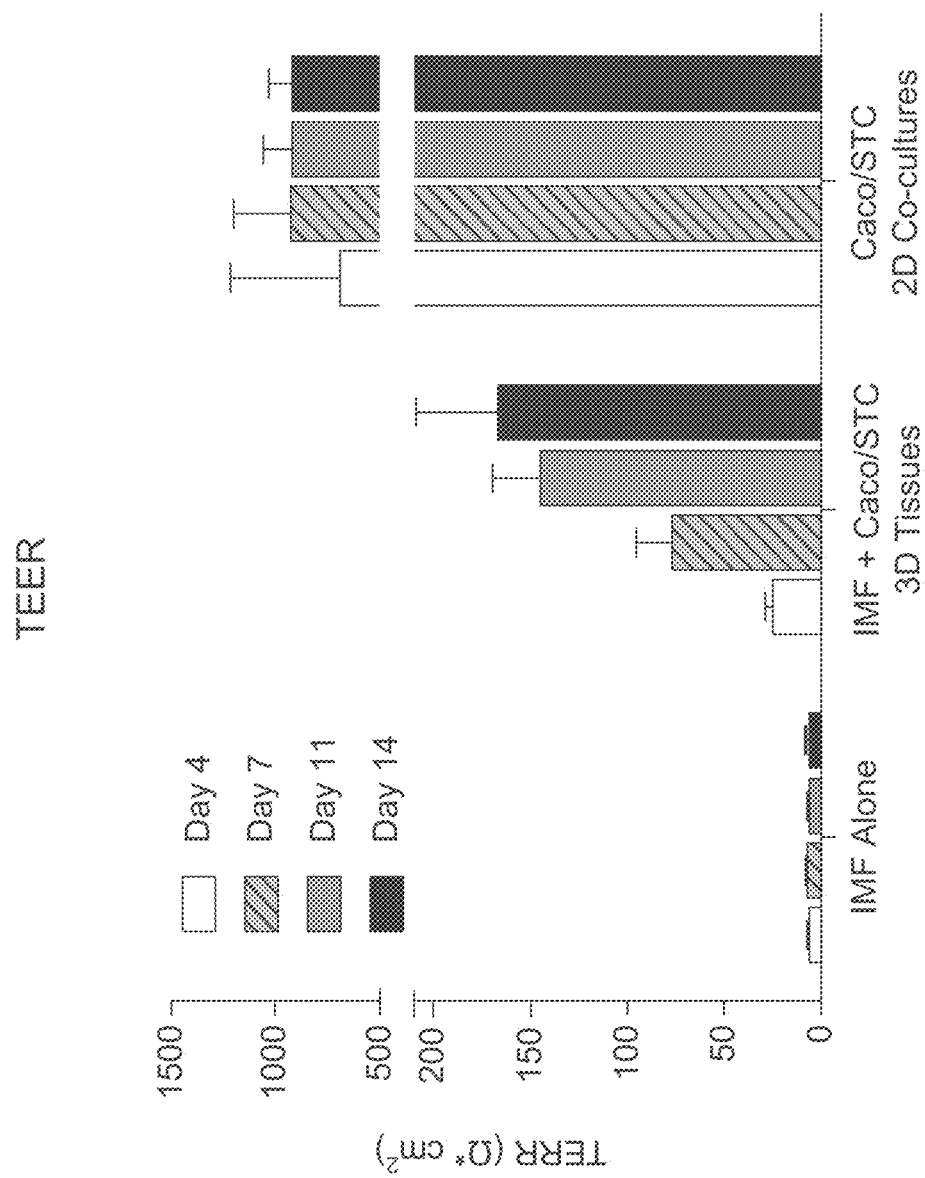
FIG. 4 is a bar graph showing barrier function comparison of 2D monolayers and 3D bioprinted Caco-2 tissues measured by transendothelial electrical resistance (TEER). TEER was used to evaluate the quality of an intestinal epithelial barrier in 2D co-cultures and 3D tissues containing Caco-2/STC-1. Barrier function was followed as a time course over 14-day culture period. The data demonstrates that barrier function increases over time in 3D tissues. The values for barrier function in 3D tissues fall within the physiological range while the values for 2D monolayers may be artificially high. The normal small intestine TEER values are 50-100 $\Omega \cdot cm^2$ (Srinivasan B., Kolli A. R., Esch M. B., Abaci H. E., Shuler M. L., Hickman J. J. (2015)). TEER measurement techniques for in vitro barrier model systems. J Lab Autom 20(2), 107-126).
Figure 5:
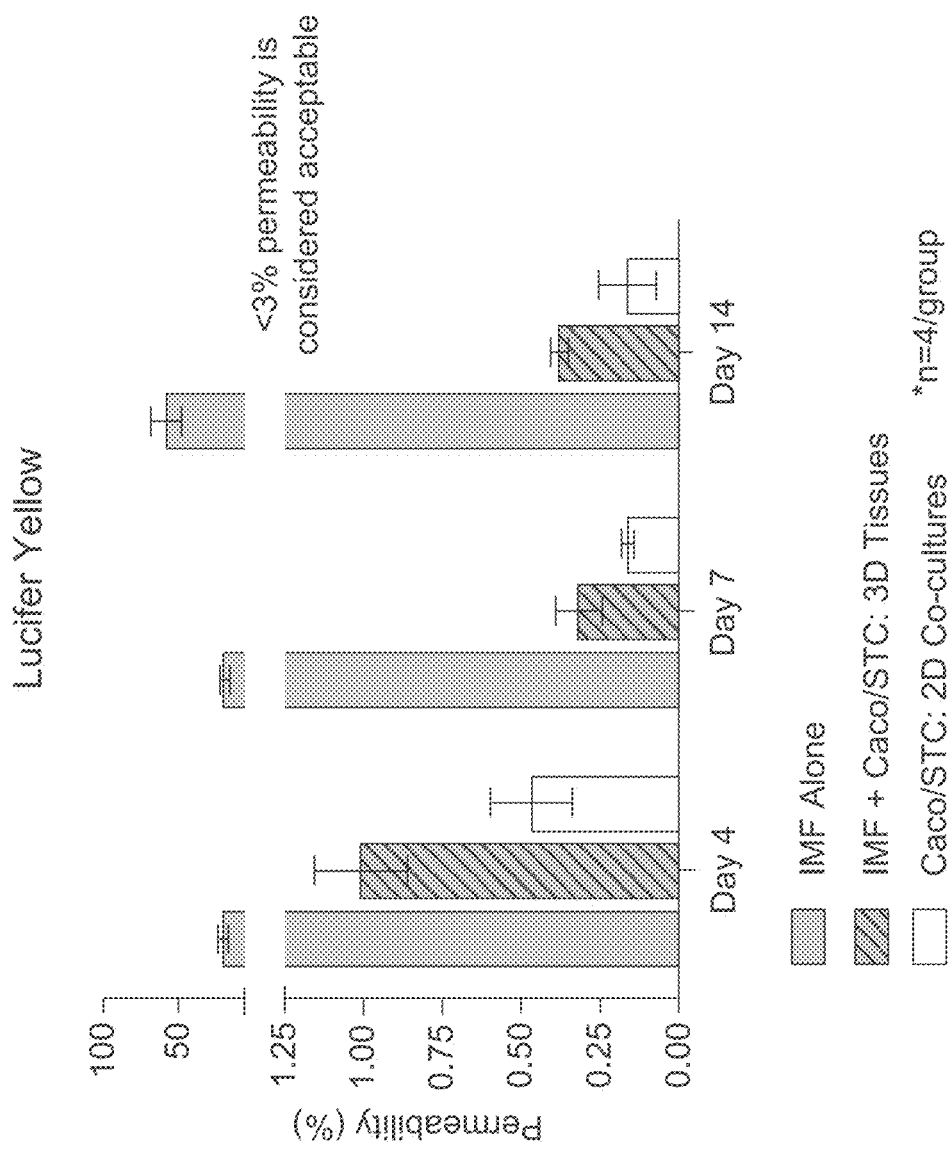
FIG. 5 is a bar graph showing permeability comparison of 2D monolayers and 3D bioprinted Caco-2 tissues measured by Lucifer Yellow. Lucifer Yellow was used to demonstrate barrier integrity over multiple time points in culture. Permeability was measured on 3D printed tissues and compared to 2D epithelial monolayers of Caco-2/STC-1 cells and interstitium alone. Both bioprinted 3D constructs and 2D monolayers exhibit low permeability within an acceptable range (<3% as later stages of culture). The data suggests that 3D tissues have low enough passive permeability for transport assays.
Figure 6B:
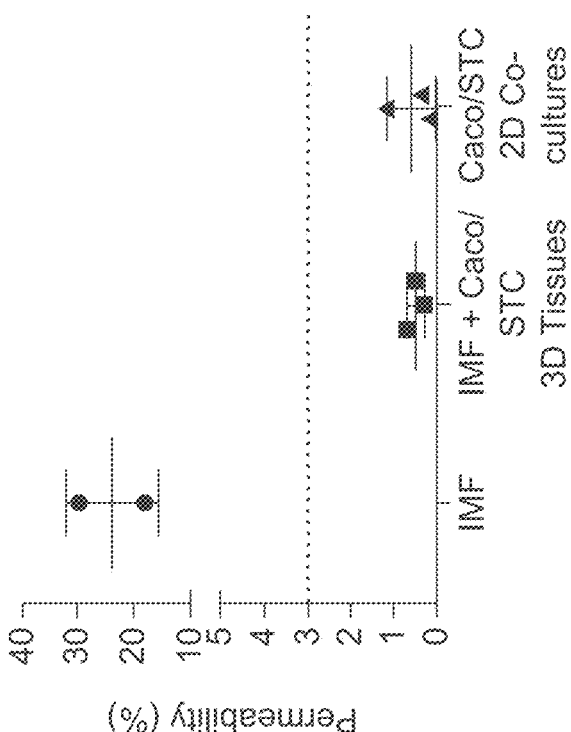
FIGS. 6A-6B are graphs showing TEER (FIG. 6A) and permeability (FIG. 6B) data averaged over multiple experiments.
Figure 6A:
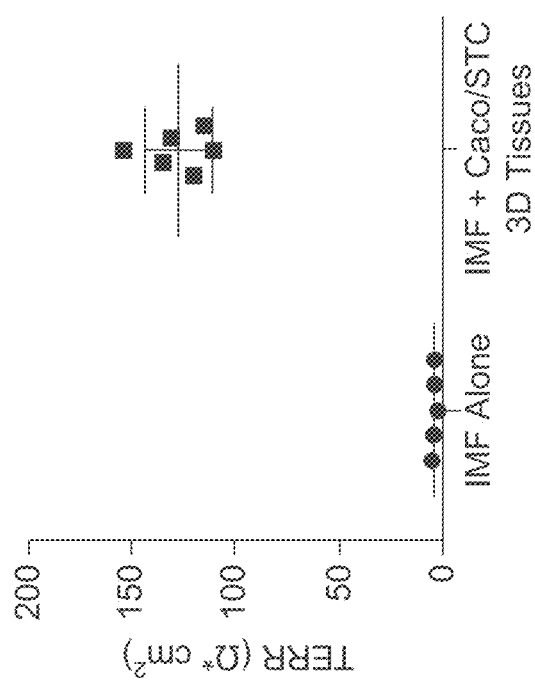

The tissues expressed markers of normal native intestinal tissue. H&E showed thickening of the epithelial layer over time while the bi-layered structure of vimentin+ myofibroblasts and CK19+ epithelial cells was maintained (FIG. 2A). Each layer expressed the correct markers, with basal lamina stained by collagen IV in the IMF layer and E-Cadherin in the epithelial layer, indicating the presence of tight junctions. The presence of tight junctions is a key finding that indicates a barrier is forming within the epithelium. Correct polarization of the epithelial cells, shown by apical staining of villin, was seen early in culture with some disorganization as tissues thickened over time. A polarized epithelium is also a key finding that signifies cells are spatially organizing as the tissues mature (FIGS. 2B-2F). The PCNA staining demonstrates that the tissues are highly viable and proliferating in culture. These tissues were stained for MUC2 and Alcian blue/PAS that indicates they do not express mucins, which is expected as it is known that Caco-2 cells do not produce mucus (FIGS. 3A-3C).

SV40 T-antigen was used to identify the STC-1 cells and showed aggregation and segregation from Caco-2 cells at early time points, followed by invasion into the interstitium at later time points. The 3D system allows for visualization of STC-1 cell behavior, which was not possible in 2D co-cultures and suggested that the STC-1 cells take on a phenotype similar to the tumor tissue they were originally isolated from. This suggests that the model system could be used to study the interaction of tumor cells with a healthy tissue microenvironment, including assessing effects on tumor growth and invasion/metastasis. While both cell lines may have an artificially high growth rate compared to native tissue or primary epithelial cells, Caco-2 cells were observed to dominate the epithelial layer over time in culture (FIG. 3A-3C).

Bioprinted tissues developed a barrier as measured by TEER and Lucifer yellow. Barrier formation was artificially high in Caco-2/STC-1 2D monolayer cultures as expected from historic literature on Caco-2 cells. A key finding was that barrier function was within a physiological range in 3D tissues, suggesting the 3D environment is more physiologically relevant than 2D monolayers and may produce more native-like tissues. Also note that TEER and permeability data is reproducible across multiple experiments highlighting the reproducibility of the bioprinted approach (FIGS. 4, 5, and 6A-6B).

Figure 7:
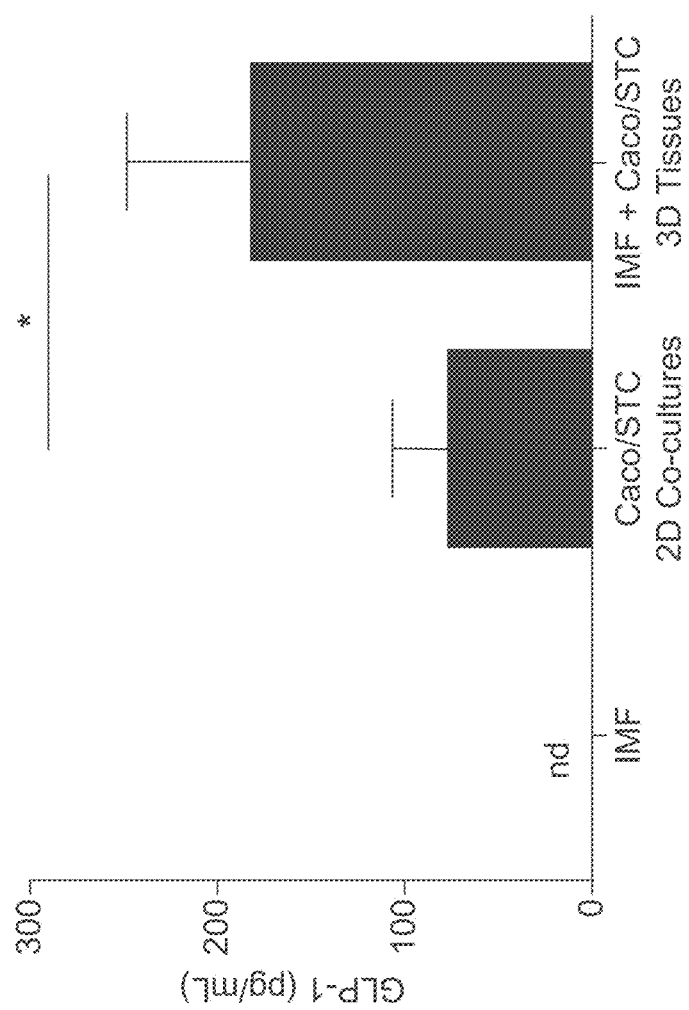
FIG. 7 is a bar graph showing functional assay validation of enteroendocrine cell GLP-1 secretion from bioprinted Caco-2 tissues.

Bioprinted tissues produce GLP-1 7 days post addition of the epithelial layer. This indicated that the STC-1 cells are present in the tissue and functional as it is known that Caco-2 cells alone cannot produce GLP-1. 3D tissues produce more GLP-1 then 2D monolayers at the same time point. This finding was unexpected and may again support the beneficial effect of a 3D environment on cell behavior. It may also reflect the increased thickness of 3D tissue and potentially increased number of cells present in 3D epithelium as it matures in culture. (FIG. 7)

Figure 8:
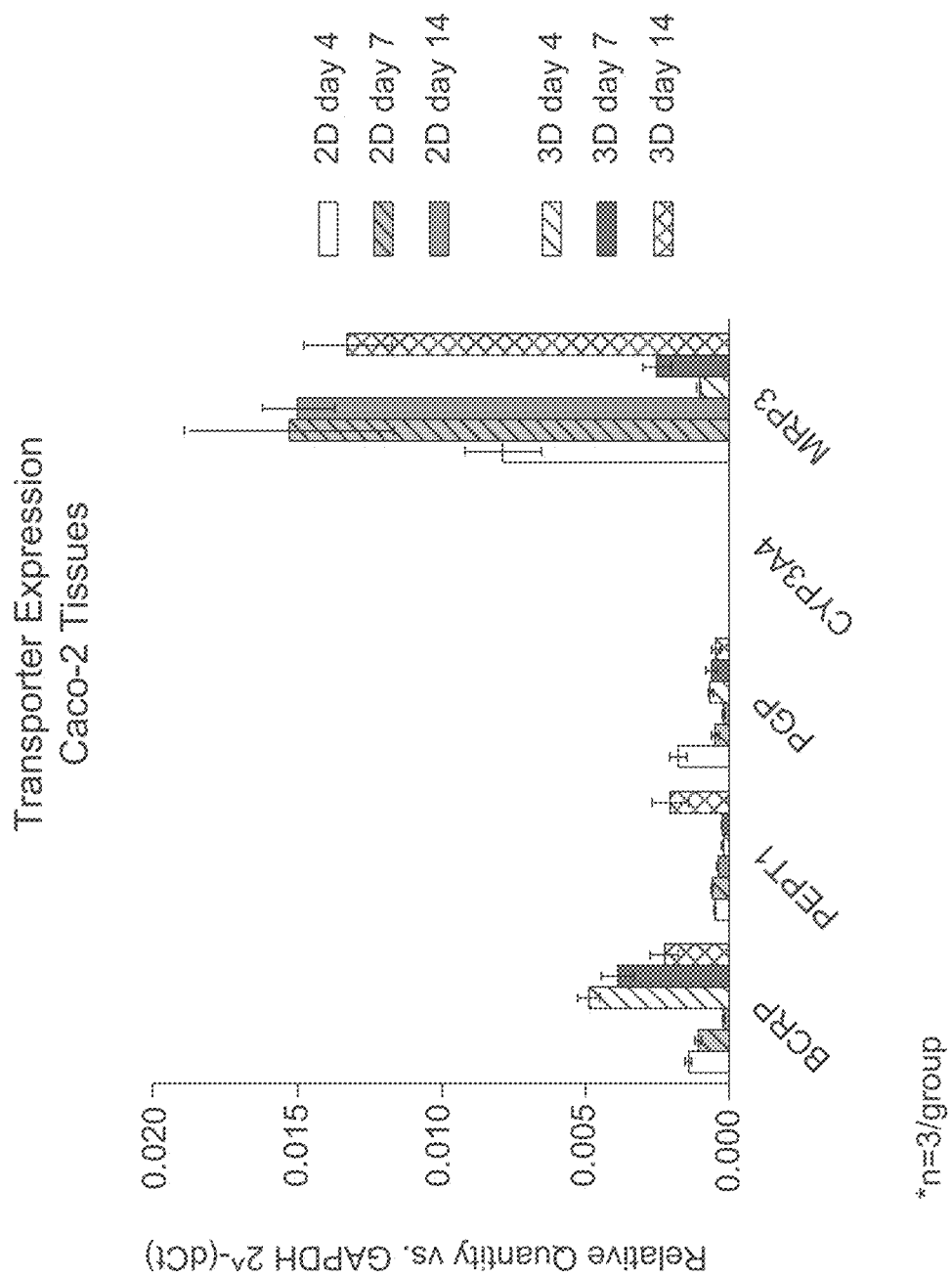
FIG. 8 is a bar graph showing time course of gene expression comparison of 2D monolayers and 3D bioprinted Caco-2 tissues. Sustained gene expression is observed for panel of transporters/enzymes in 3D tissues vs. 2D cultures. CYP3A4 expression is low compared to transporters. Trace amount (0.000004) is detected at day 14 in 3D tissues.
Figure 9A:
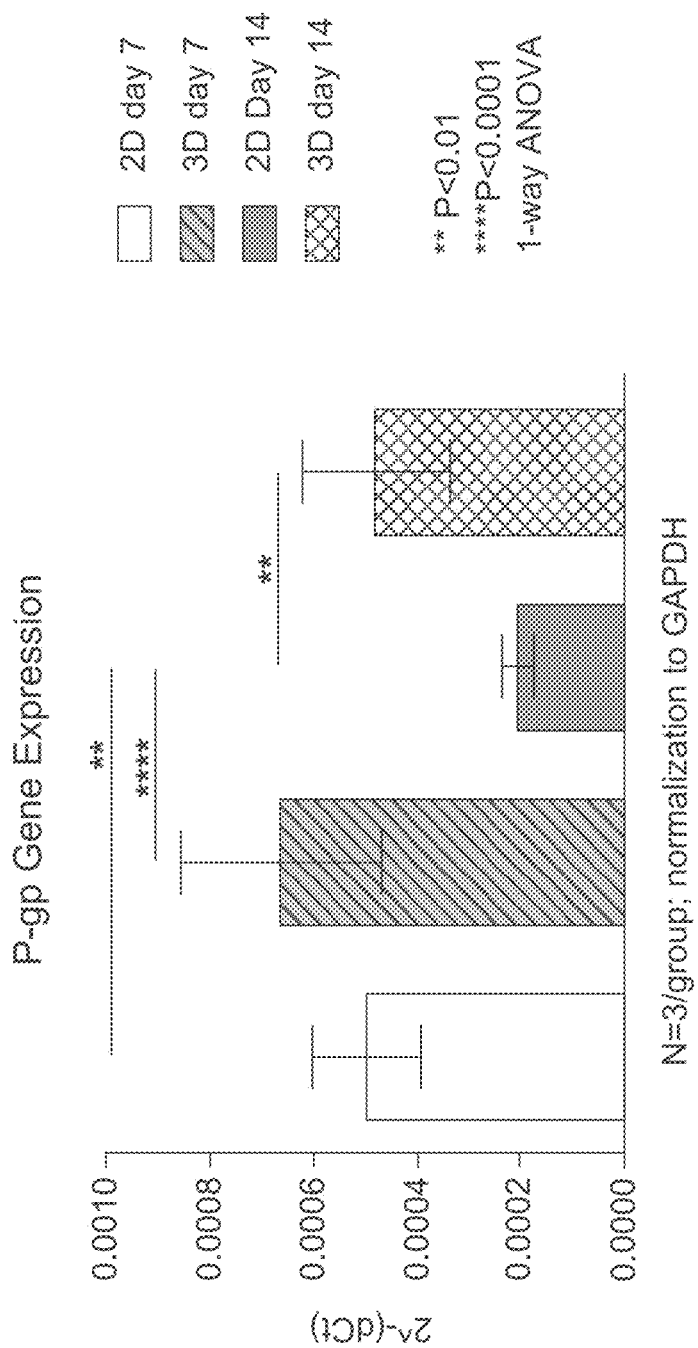
FIGS. 9A-9B are a bar graph and micrographs showing P-gp expression comparison of 2D monolayers and 3D bioprinted Caco-2 tissues. P-glycoprotein (P-gp) is an efflux transporter on the apical surface of the intestinal epithelium. Although P-gp gene expression is similar in 2D monolayers and 3D bioprinted Caco-2 tissues at Day 7 (FIG. 9A), improved P-gp protein expression is observed by immunohistochemistry staining in 3D bioprinted Caco-2 tissues, with enhanced expression in late stages of culture (FIG. 9B).
Figure 9B:
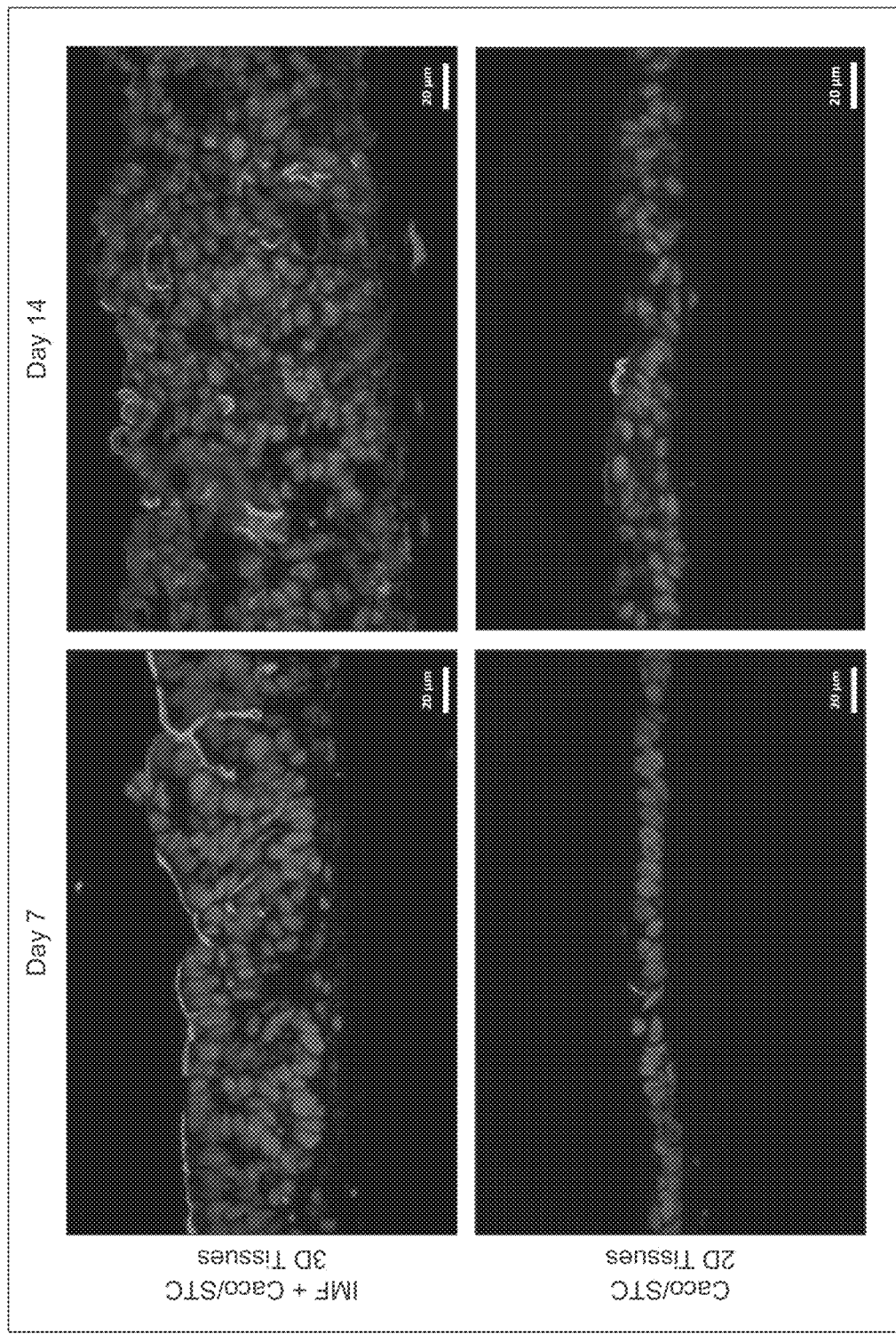

3D Caco-2 tissues express key transporters in a similar pattern to 2D monolayers by qPCR. Patterns may be different at different time points studied, but collectively data shows that both 2D and 3D tissues express the same markers within a similar range. Histology indicated that P-gp may be more upregulated in 3D tissues, which is an unexpected finding. Also the P-gp staining was on the apical side of the epithelium, again supporting proper polarization of epithelial cells and proper location of an apical efflux transporter similar to native tissue. (FIGS. 8 and 9A-9B)

Example 2

A Bioprinted Three-Dimensional Intestinal Tissue Model

A human intestinal tissue construct was fabricated by bioprinting with 100% human adult primary intestinal cells by continuous deposition using interstitial bio-ink containing collagen followed by deposition of epithelial suspension.

Bio-ink was generated by a cellular mixture of 100% primary adult human intestinal myofibroblasts (IMF) in 100% bovine type I collagen at a concentration of 20 million cells per milliliter. Three-dimensional bio-ink constructs were printed by continuous deposition using the Novogen MMX Bioprinter® in a base layer to create an interstitial structure. One tissue was printed per transwell in a 24 well plate. The transwell printing surface contained a polytetrafluoroethylene (PTFE) membrane coated with equimolar mixture of types I and III collagen (bovine) with pores 3 um in size. Following printing, tissues were allowed to mature for 4 days in a humidified 37° C. incubator in 100% IMF media and media was changed daily. After incubation, interstitial tissue constructs were removed from the incubator and placed in a BSC hood. Media was aspirated immediately before application of epithelial cells. Epithelial cells were dispensed as a cell suspension of 100% primary adult human intestinal epithelial cells onto the printed interstitial layer. Media used contained 100% primary intestinal epithelial cell growth media. In some wells no epithelial cells were added to the printed IMF layer and these wells were used as a control for comparison studies. After deposition, media was added to the outer area of the transwell basket. Media was changed every 24-28 hours for up to 21 days. Full culture period is 4 days of IMF interstitial tissue incubation plus 9, 10, or 17 days post addition of epithelial cells. Thus, experiments are labeled as day 9, 10, and 17, which corresponds to a full culture time of 13, 14 and 21 days, respectively.

Experiment time course studies were run 0, 9, 10, and 17 days post addition of epithelial cells. Tissues were measured for GLP-1 secretion into supernatant at day 10 and 17. Tissues were also measured for barrier function at multiple time points by TEER or Lucifer yellow (non-lytic assays). After incubation, the tissues were fixed in paraformaldehyde (PFA) for histology or lysed for RNA extraction.

Results

Figure 10:
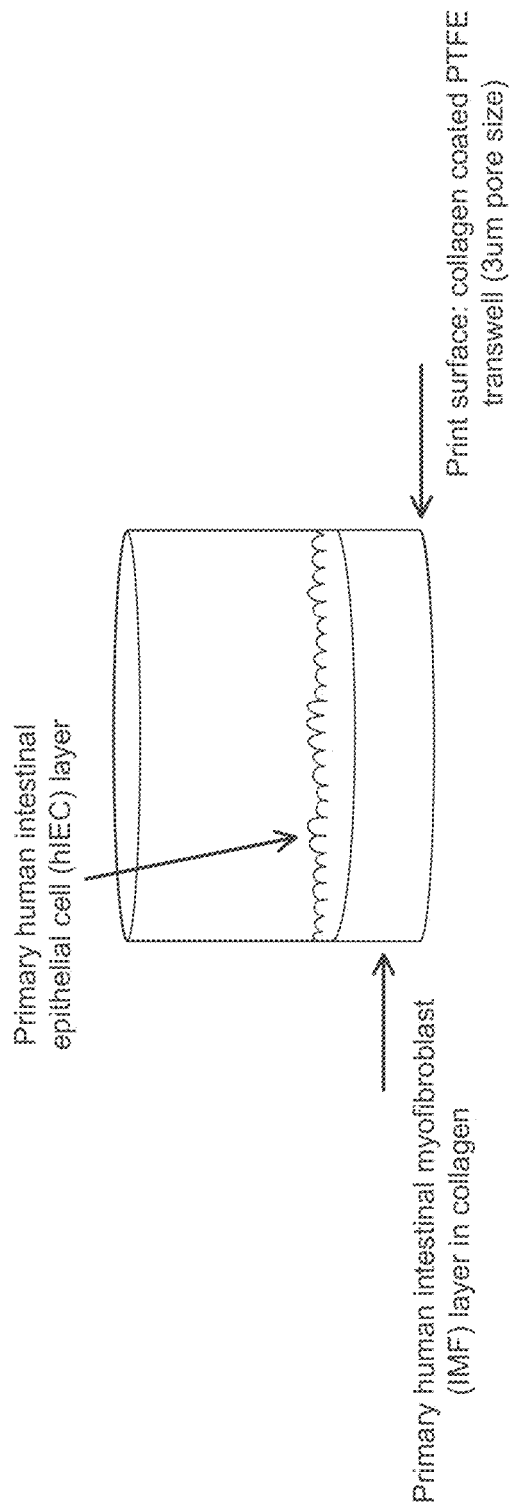
FIG. 10 is a schematic showing the print surface, a layer of primary intestinal myofibroblasts in collagen, and a top layer of primary human intestinal epithelial cells.

Bioprinted intestinal tissues maintained a cohesive structure after incubation in media and achieved a bi-layered architecture. Tissues were cross sectioned perpendicular to the plane of the transwell to show the interstitial and epithelial layers (FIG. 10). A key finding is that tissues printed exclusively with primary intestinal cells in both the interstitium and epithelium exhibit the correct architecture and expression patterning similar to native tissue. Tight junctions indicate the epithelial cells formed a barrier. Epithelial cell layer is organized and polarized, with clear apical staining of villin suggesting a brush border was formed. A key finding is that 3D tissues are viable (PCNA staining) throughout 17 day culture period. Tissues also express P-gp and BCRP, efflux transporters in the correct apical expression pattern. It is also important to point out that this laminar architecture is in contrast to alternative non-bioprinted methods of culturing primary intestinal epithelial cells in vitro, which produces round aggregates with epithelial cells directed inwardly toward the center (intestinal organoids). In a rounded conformation, the apical surface is not exposed and cannot be utilized for direct stimulation of compounds, nor does it allow for the collection of sample from both apical and basolateral sides of the intestinal wall that are required for absorption/permeability assessment. (FIGS. 11A-11D)

Figure 11A:
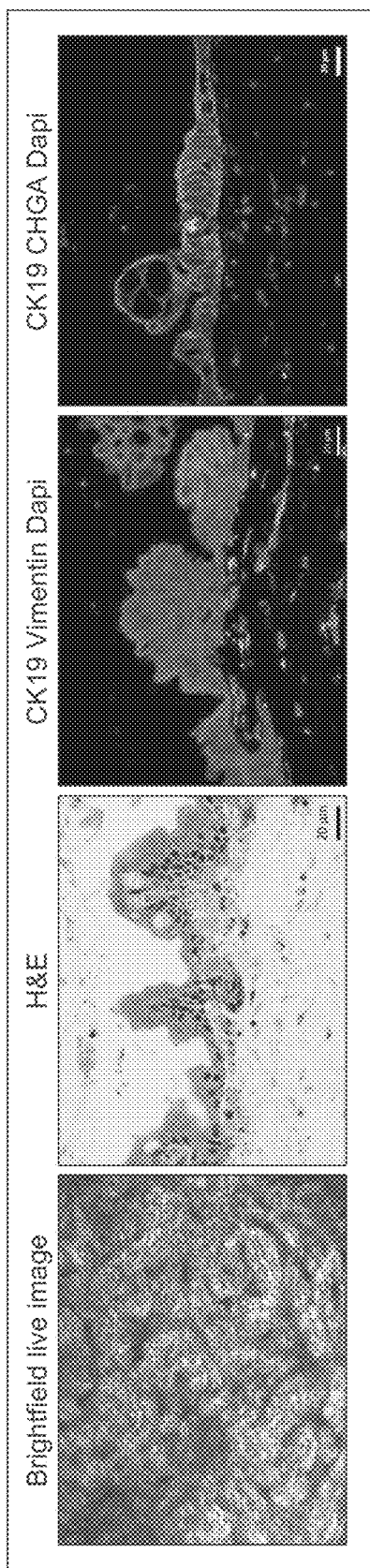
FIGS. 11A-11D are histological graphs showing that bioprinted 3D primary intestinal epithelial cell (IEC) tissues express key features of native tissue. Histology panel at Day 9, 10, and 17 shows 3D primary human intestinal epithelial cells (hIEC) tissues express key features of native tissue. Tissue exhibits correct architecture, epithelial cells form tight junctions and polarize with expression patterning similar to native tissue.
Figure 11B:
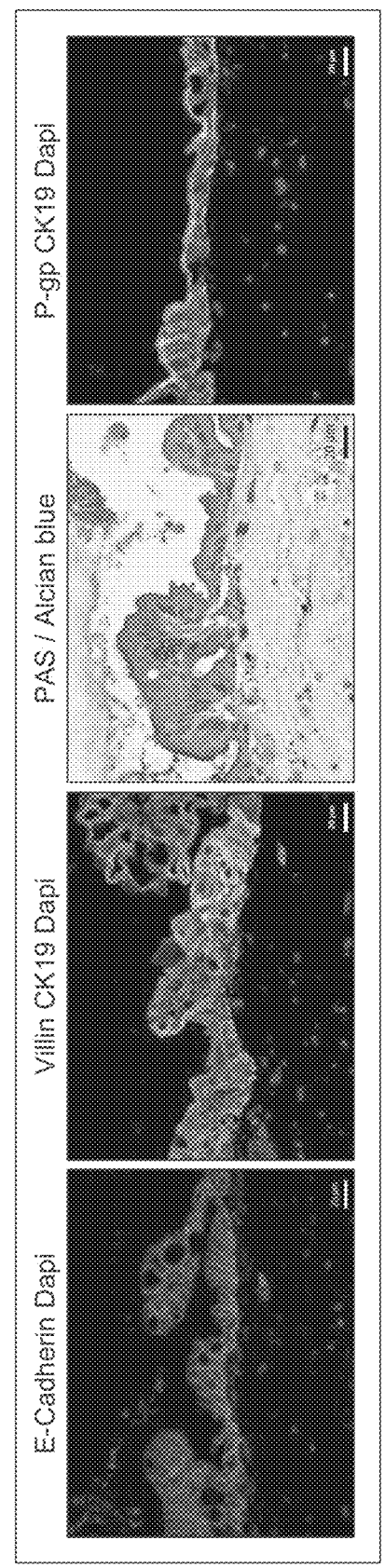
Figure 11C:
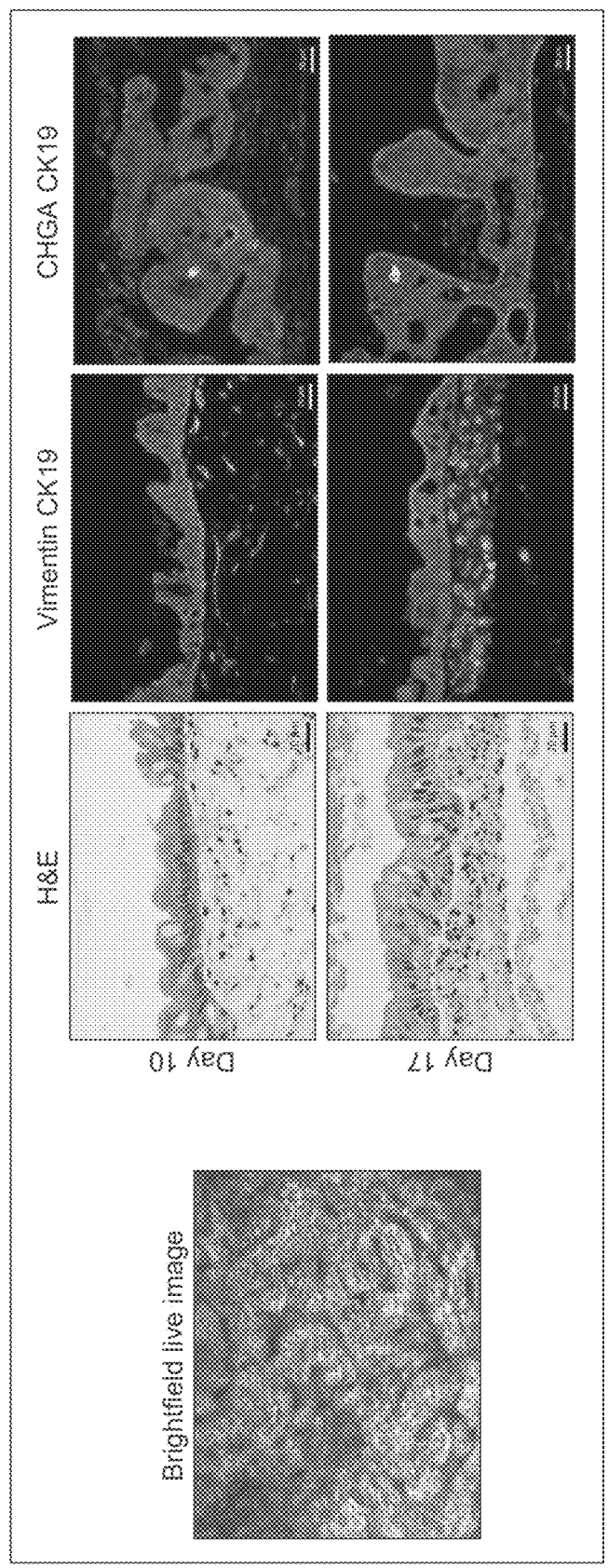
Figure 11D:
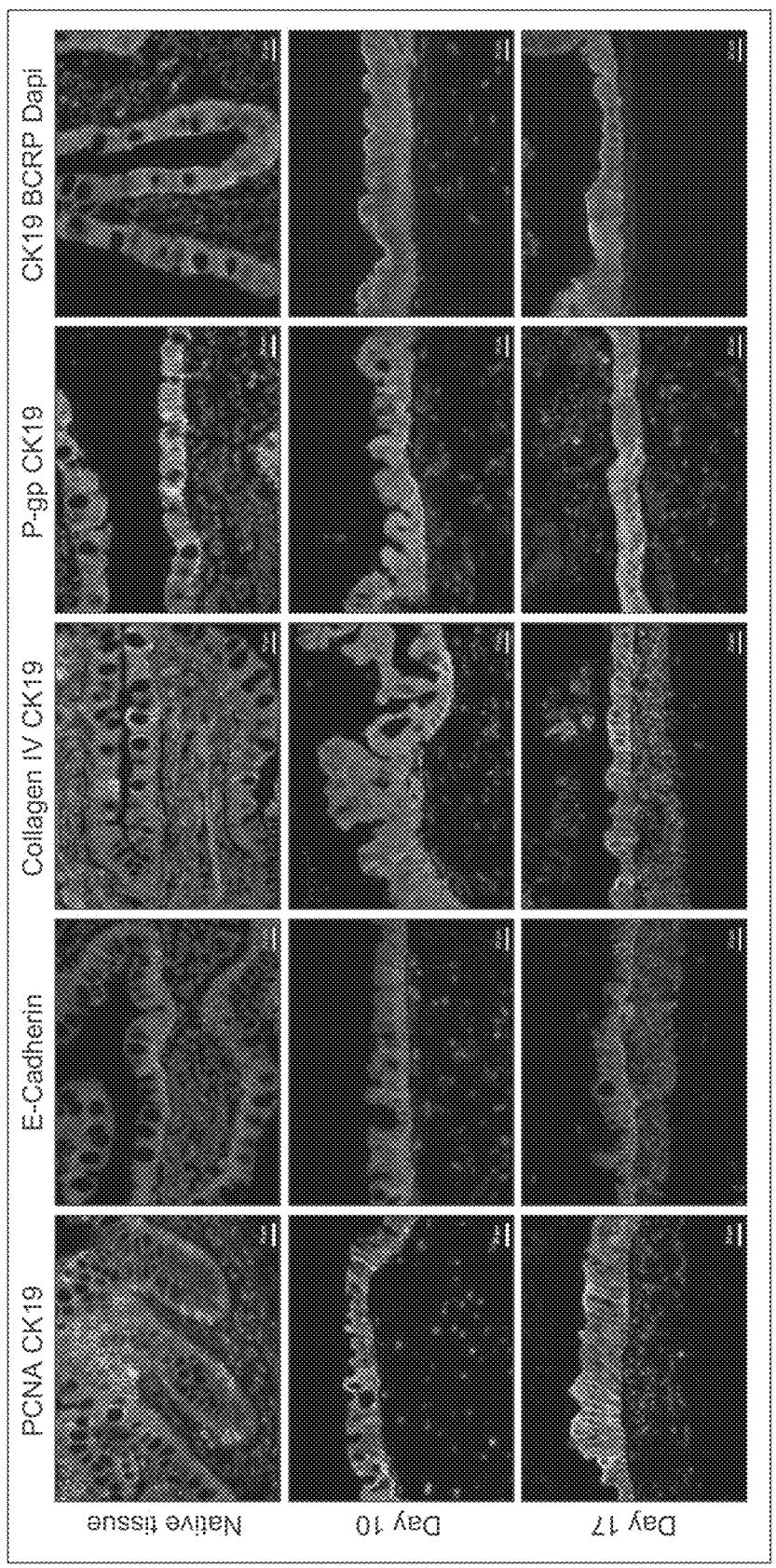

Brightfield imaging of the tissue shows formation of secondary villi-like structures on the epithelial surface. This is important because it supports that the gross morphology of the bioprinted tissue resembles native tissue. This was also seen at day 9 of culture, indicating that the 3D environment provided by bioprinting may enhance tissue differentiation. (FIGS. 11A and 11C)

Tissues show presence of chromogranin A (CHGA) positive cells, a marker for enteroendocrine cells. This finding is important because it demonstrates the presence of specialized epithelial cell types normally found within native tissue can also be found in bioprinted tissue with primary intestinal epithelial cells. It is a key finding because it suggests that a stem cell population may be present within the primary epithelial cells and that this population is capable of differentiating within the 3D tissue environment. It is also a key finding because Caco-2 cells alone do not have endocrine function or CHGA positive cells. (FIGS. 11A and 11C)

Figure 12:
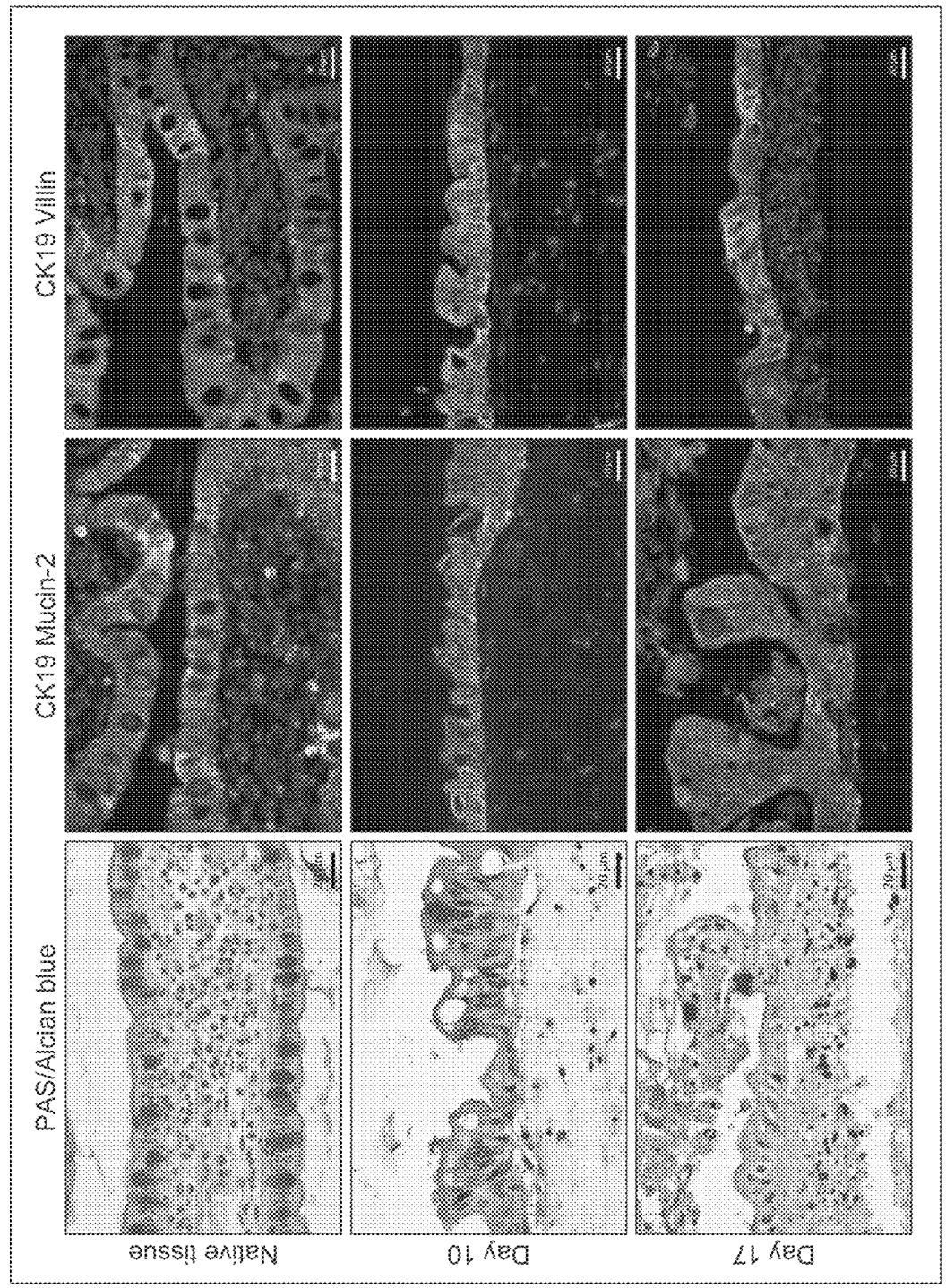
FIG. 12 is a panel of histological graphs showing that bioprinted 3D primary IEC tissues produce mucus. Mucin-2 staining can be seen in tissues with primary intestinal epithelial cells but not in 3D Caco-2 tissues. Staining demonstrates polarized epithelium with apical brush border formation, goblet cells, and mucus production. Caco-2 tissues do not contain goblet cells or produce mucus.

3D tissues fabricated with primary intestinal epithelial cells produce mucus and apical brush border. This finding highlights the fact that bioprinted gut tissues organize and function in a manner similar to native tissue. This is a key finding because gold standard Caco-2 tissues do not produce mucus and therefore cannot be used as a model for a mucosal barrier. Goblet cells are present. This is key because Caco-2 cells do not have goblet, or goblet-like cells. It again suggests that a stem cell population may be present within the primary epithelial cells and that this population is capable of differentiating. Furthermore, it may be possible to direct this differentiation by modifications to the printing approach and culture conditions. (FIG. 12)

Figure 13A:
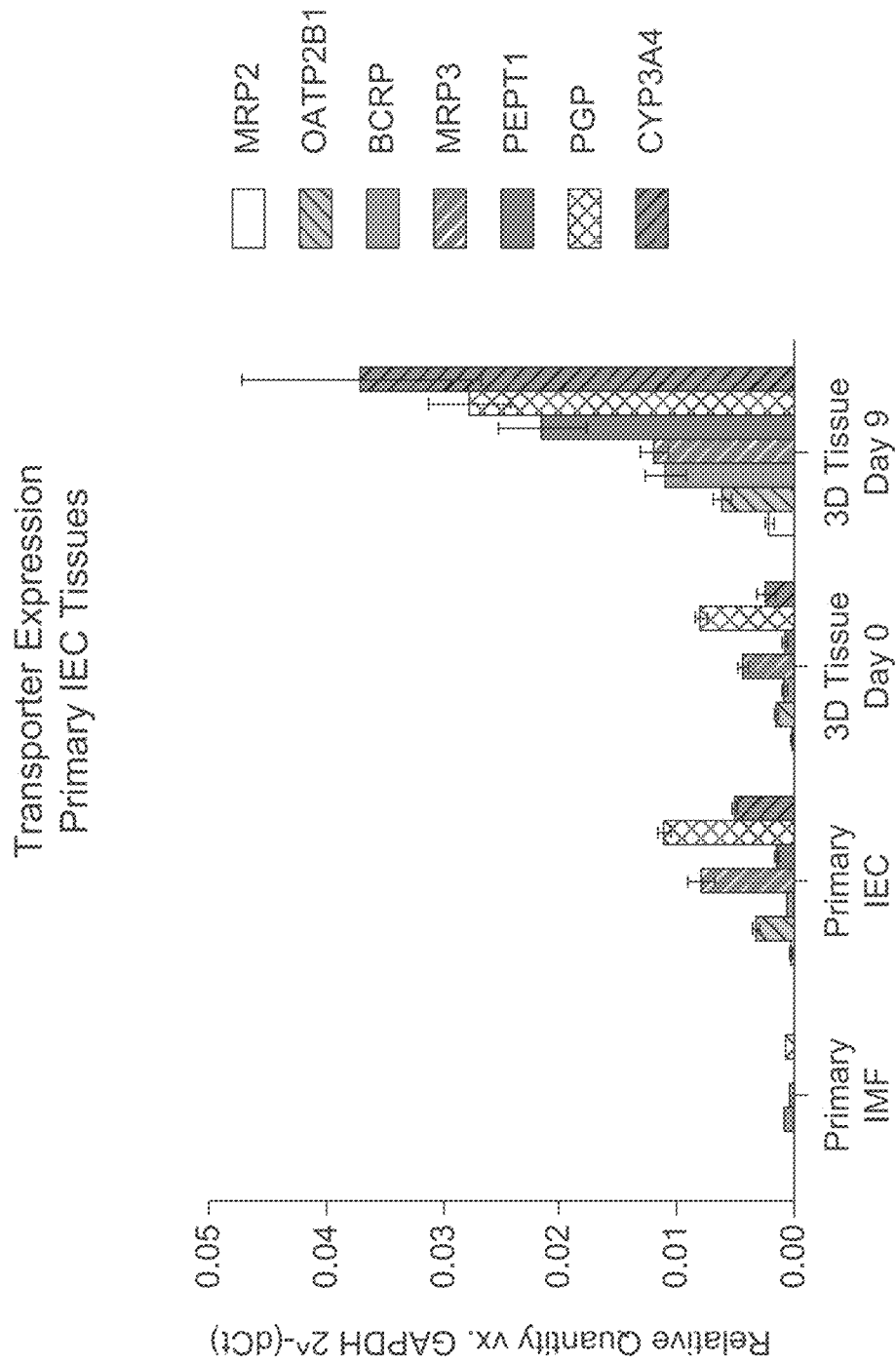
FIGS. 13A-13B are bar graphs showing that bioprinted 3D primary IEC tissues express key transporters and enzymes. Expression values of all genes analyzed in this panel are induced as tissues mature.
Figure 13B:
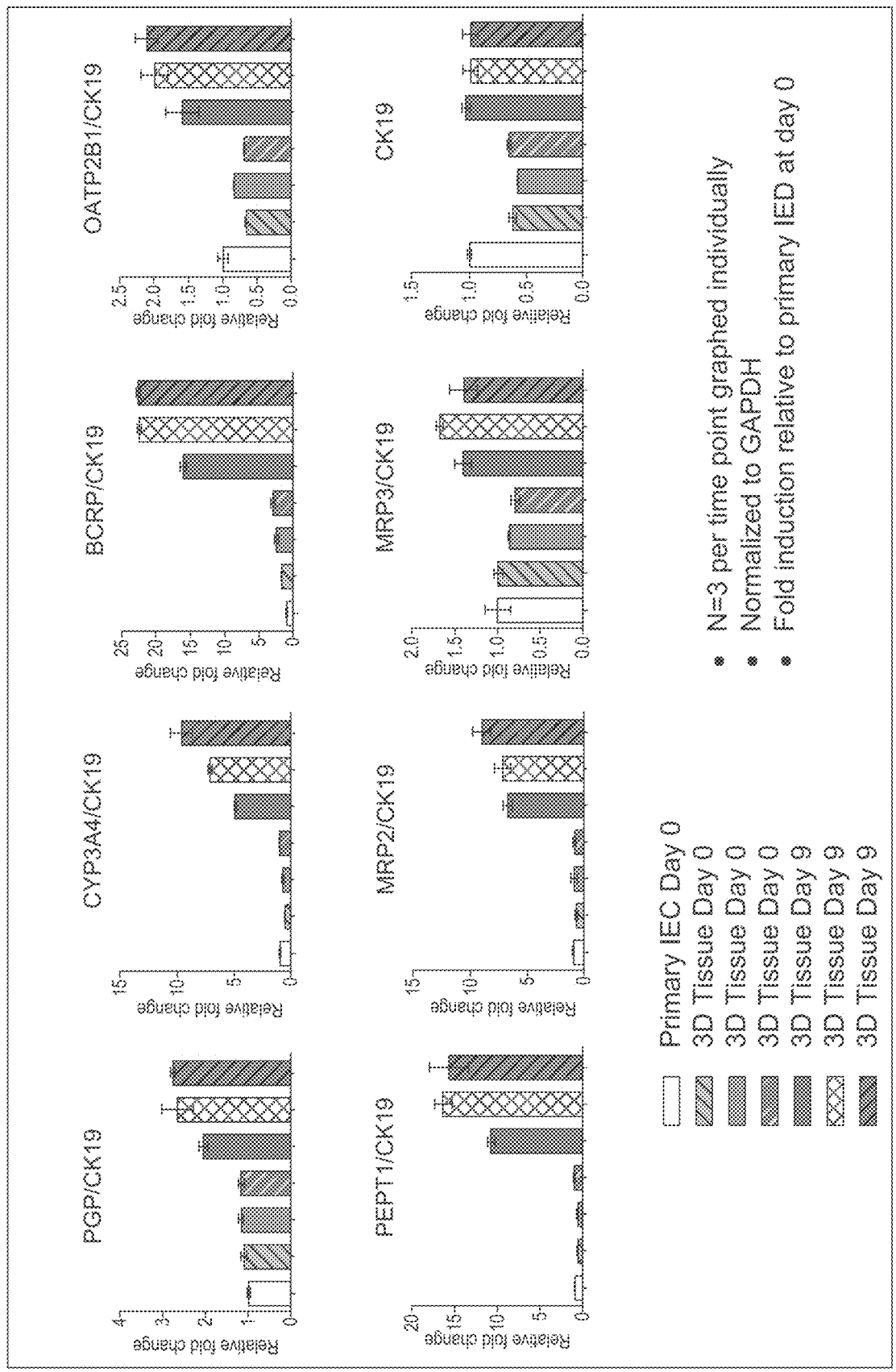

Bioprinted tissues express key transporters and metabolic enzyme CYP3A4. Gene expression analysis shows all markers tested were upregulated as tissues mature in 9 day culture period, again supporting that tissues are viable in culture. Normalization of expression values to epithelial-specific marker CK19 showed that upregulation of expression is specific to epithelial cells, similar to native tissue. Separation of biological replicates (n=3) also highlights the reproducibility between bioprinted tissues. (FIGS. 13A-13B)

Figure 14:
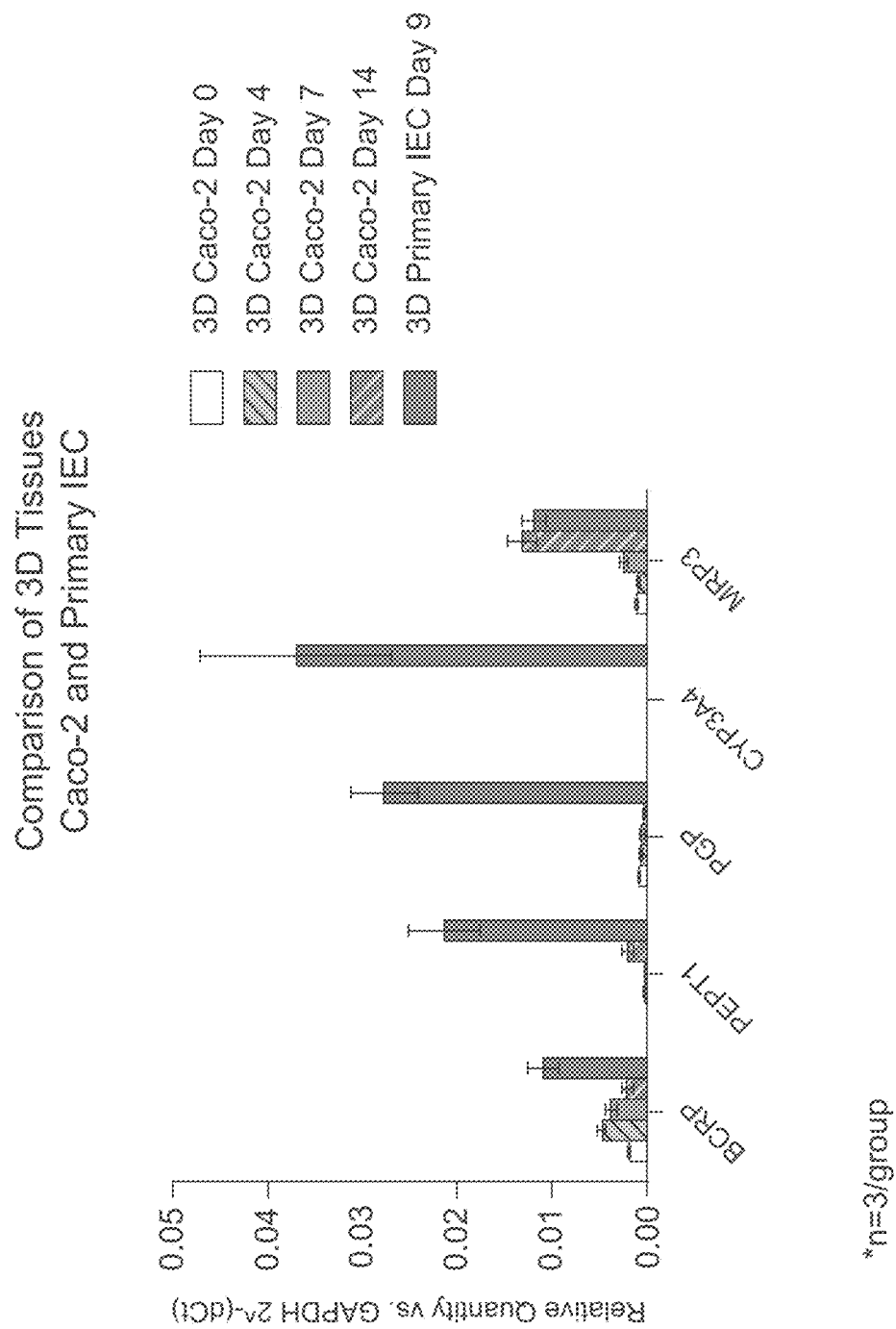
FIG. 14 is a bar graph showing that transporter and metabolic gene expression in 3D tissues with primary IEC is higher compared to 3D Caco-2 tissues. Gene expression of 3D Caco-2 tissues is compared at multiple time points to primary tissue at Day 9. Overall transporter gene expression in primary IEC tissue is much higher than 3D Caco-2 tissues with the exception of MRP3. Expression of metabolic enzyme CYP3A4 is very high in primary tissue and absent in 3D Caco-2 tissues.

Transporter and metabolic enzyme expression in primary intestinal epithelial cells was much higher than and therefore superior to 3D Caco-2 tissues. A very important differentiator of tissues fabricated with primary intestinal epithelial cells was that key P450 metabolic enzyme CYP3A4 expression was very high in primary IEC and completely lacking in Caco-2 tissues. CYP3A4 activity is a key metabolic enzyme used to study drug metabolism. It is widely known that Caco-2 cells cannot be used as an in vitro model to study CYP3A4 activity due their lack of CYP3A4 expression. This data highlights a key advantage of the bioprinted intestinal tissue constructs over conventional in vitro models. (FIG. 14)

Figure 15:
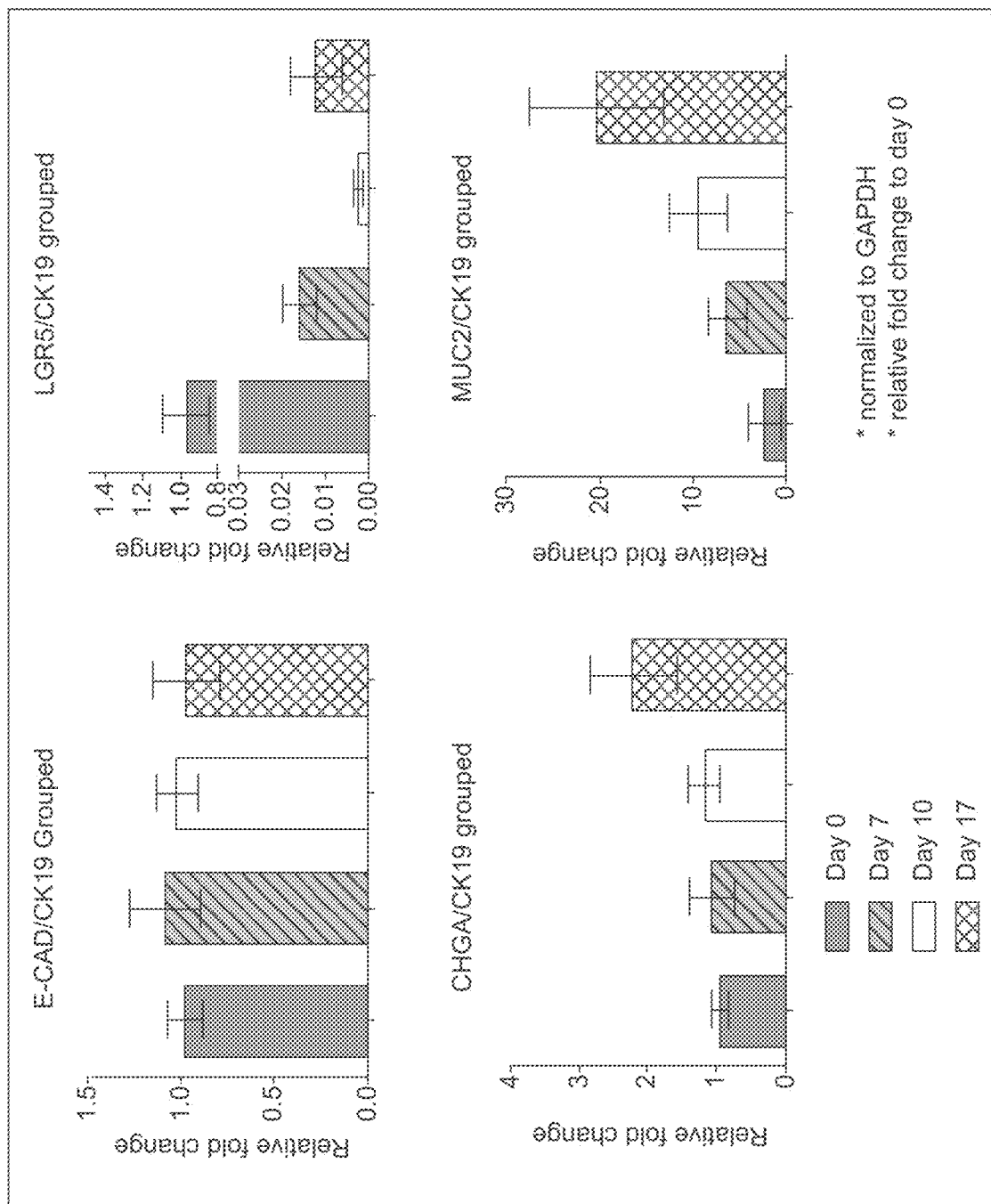
FIG. 15 is a panel of bar graphs showing that gut epithelium differentiates over time. Tissues fabricated with primary intestinal epithelial cells express key specialized cell types found in native intestine. Enteroendocrine cell marker is CHGA, goblet cell marker is MUC2. An increase in CHGA and MUC2 and a decrease in LGR5 are observed, suggesting that epithelial cells are differentiating. Values are represented as a ratio to CK19 to visualize changes specific to the epithelial cell population in tissues.

Intestinal stem cell marker LGR5 was expressed at Day 0 (when the epithelial cells are added), suggesting that the primary intestinal epithelial cell population contains a subpopulation of stem cells. Expression of stem cell marker LGR5 decreases over time in culture while markers for specialized epithelial cells including enteroendocrine cells (CHGA) and goblet cells (MUC2) increases. This suggests that stem cells were present and differentiating normally within the epithelium while the tissues mature in culture to produce specialized cell types. Primary enteroendocrine cells and primary goblet cells are not commercially available. That makes this finding important because it tells us that we can produce a 3D tissue that contains native cell types and can also potentially drive the differentiation of the tissue toward specific cell types to achieve a specific phenotype. Again, the data highlights a key advantage of bioprinted gut tissues over conventional in vitro models. (FIG. 15)

Example 3

A Bioprinted Three-Dimensional Intestinal Tissue Model Comprising Enteroendocrine Cells A human intestinal tissue construct was fabricated with human adult primary intestinal cells and mouse enteroendocrine cell line STC-1 by continuous deposition using an interstitial bio-ink containing collagen and manual deposition of an epithelial suspension.

The interstitial layer was generated in an identical manner to Example 2. Bio-ink was generated by a cellular mixture of 100% primary adult human intestinal myofibroblasts (IMF) in bovine type I collagen at a concentration of 20 million cells per milliliter. Three-dimensional bioink constructs were printed by continuous deposition using the Novogen MMX Bioprinter® in a base layer with to create an interstitial structure. One tissue was printed per transwell in a 24 well plate. The transwell printing surface contained a polytetrafluoroethylene (PTFE) membrane coated with equimolar mixture of types 1 and III collagen (bovine) with pores 3 um in size. Following printing, tissues were allowed to mature for 4 days in a humidified 37° C. incubator. Tissues were cultured in 100% IMF media and media was changed daily. After incubation, interstitial tissue constructs were removed from the incubator and placed in a BSC hood. Media was aspirated immediately before application of epithelial cells. Epithelial cells were dispensed manually onto the printed interstitial layer as a cell suspension mixture of 99% primary adult human intestinal epithelial cells and 1% mouse STC-1 cells. In some wells no epithelial cells were added to the printed IMF layer and these wells were used as a control for comparison studies. In other control wells, 100% STC-1 cells were added in the epithelium with no primary intestinal epithelial cells. After deposition, media was added to the outer area of the transwell basket. Media was changed every 24-48 hours or up to 21 days. Full culture period is 4 days of IMF interstitial tissue incubation plus 9, 10, or 17 days post addition of epithelial cells. Thus, experiments are labeled as day 9, 10, and 17, which corresponds to a full culture time of 13, 14 and 21 days, respectively.

Experiment time course studies were run 0, 9, 10, and 17 days post addition of epithelial cells. Tissues were measured for GLP-1 secretion into supernatant at day 10 and 17. Tissues were also measured for barrier function at multiple time points by TEER or Lucifer yellow (non-lytic assays). After incubation, the tissues were fixed in paraformaldehyde (PFA) for histology or lysed for RNA extraction.

Results

Figure 16A:
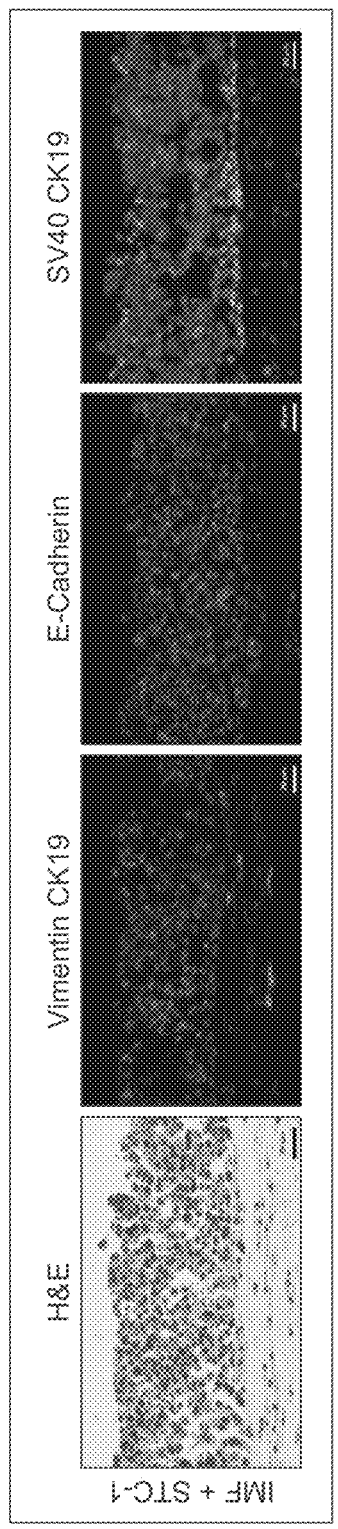
Figure 16B:
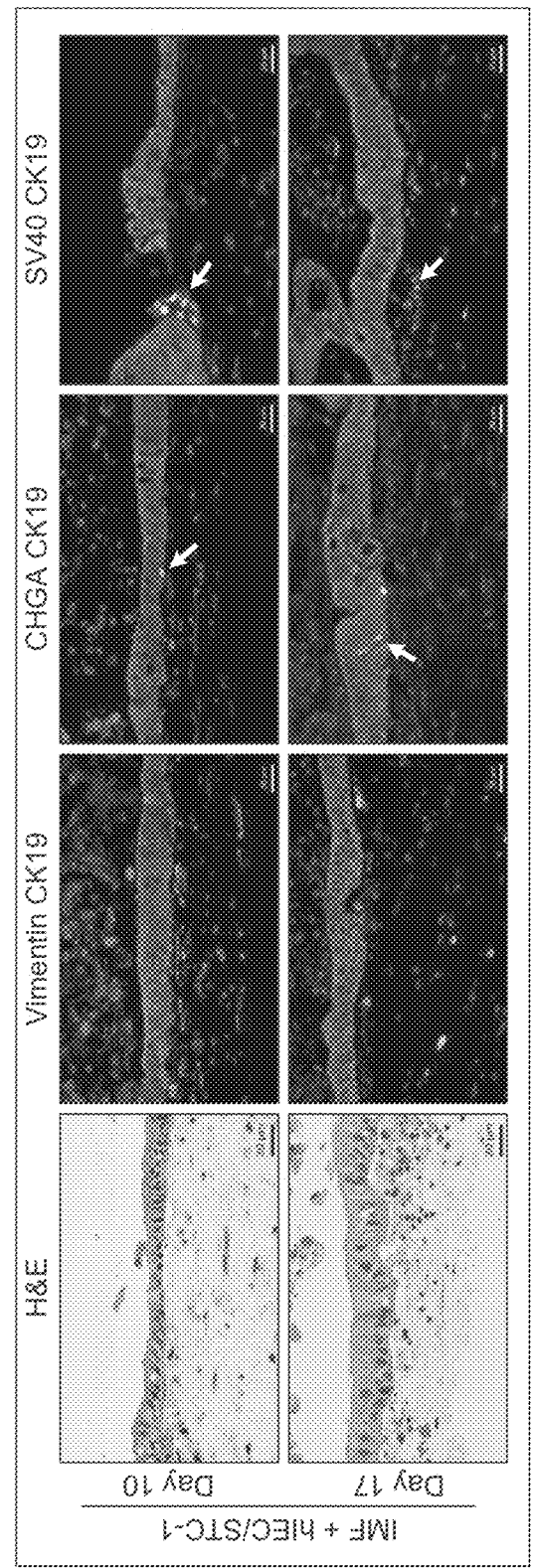
Figure 17A:
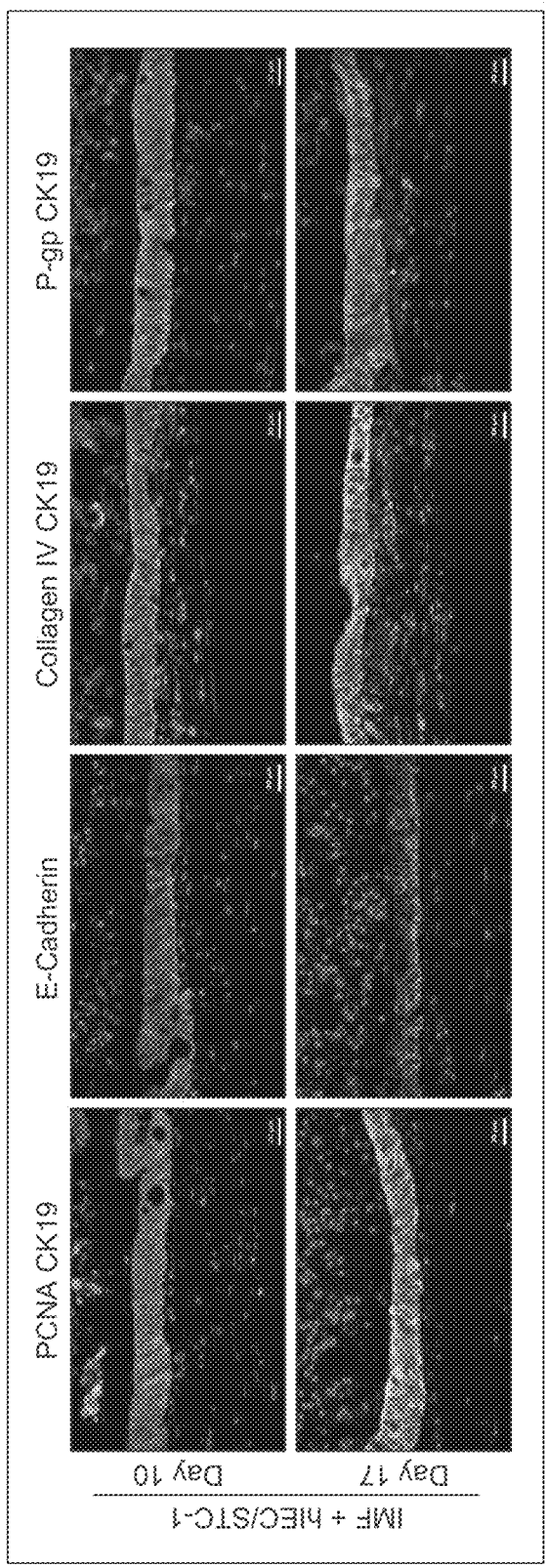
FIGS. 17A-17B are histological micrographs showing tissues incorporating STC-1 cells with primary intestinal epithelial cells into the tissue epithelium. Tissues form correct bi-layered architecture, appear similar to native tissue, and produce mucus.
Figure 17B:
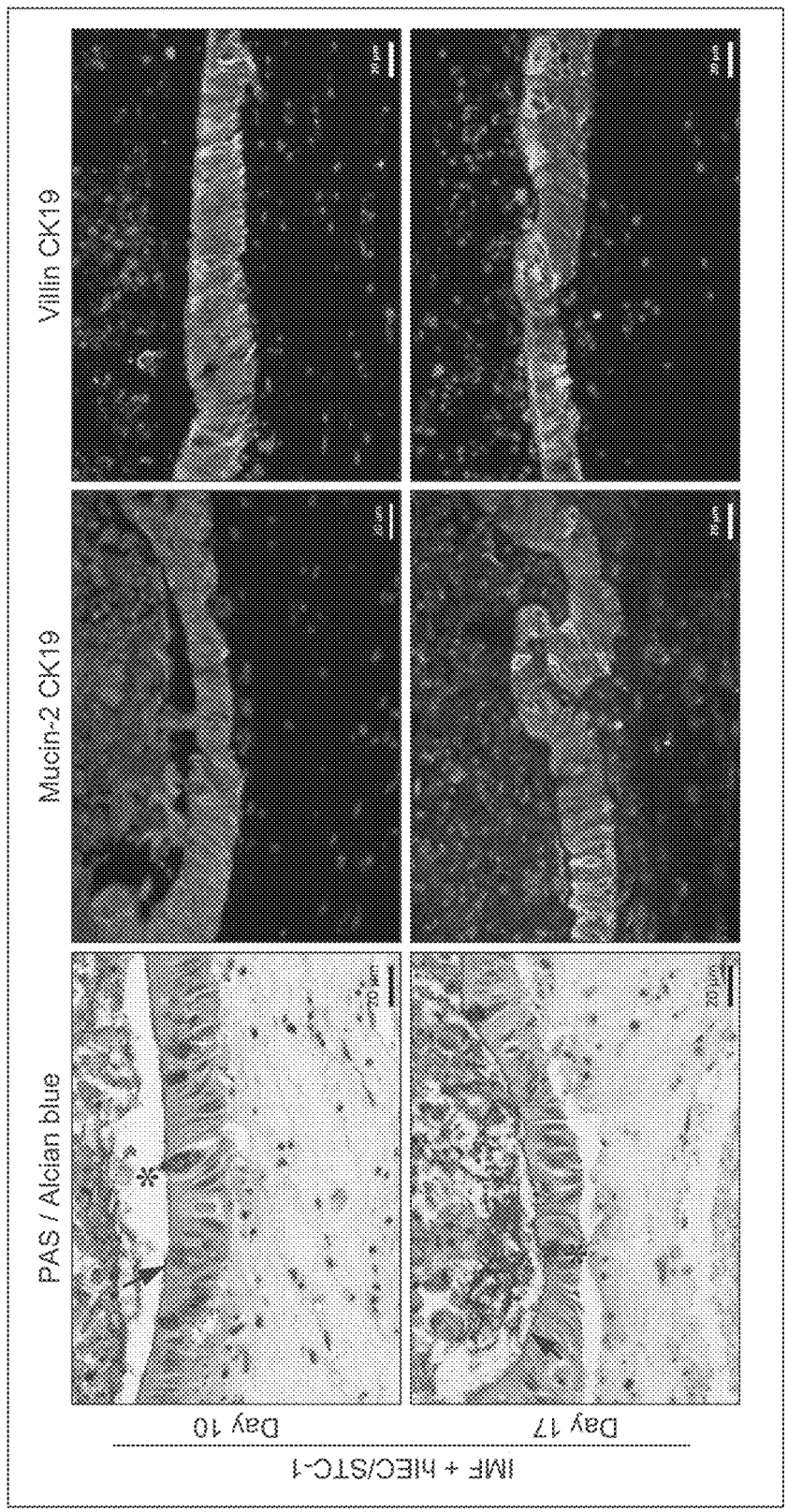

STC-1 cells alone form a thick layer when added op top of a bioprinted myofibroblast interstitial layer in the absence of primary epithelial cells, suggesting that the 3D environment may be giving them cues to aggregate. STC-1 cells do not have an epithelial phenotype as they do not express epithelial marker CK19 and they do not form tight junctions. When combined with primary intestinal epithelial cells, they do not evenly incorporate into the epithelium and instead form aggregates that invade the interstitial layer. The benefit of a 3D system is that it allows us to observe this STC-1 cell function. In addition, this suggests that the model system could be used to study the interaction of tumor cells with a healthy tissue microenvironment, including assessing effects on tumor growth and invasion/metastasis. Aggregate formation and invasion cannot be visualized in 2D monolayer co-cultures. (FIGS. 16A-16B)

Bioprinted intestinal tissues fabricated with 1% STC-1 and 99% primary intestinal epithelial cells in the epithelium appear similar in histological panel to tissues printed 100% primary intestinal epithelial cells. Similar bi-layered architecture, expression patterning, viability, and mucosal barrier staining can be seen despite the unusual behavior of STC-1 cells. The similarity in data in Example 3 compared to Example 2 highlights the reproducibility of the 3D bioprinted intestinal tissue construct phenotype and the robustness of the model. (FIGS. 16A-16B and 17A-17B)

Figures 18A, 18B:
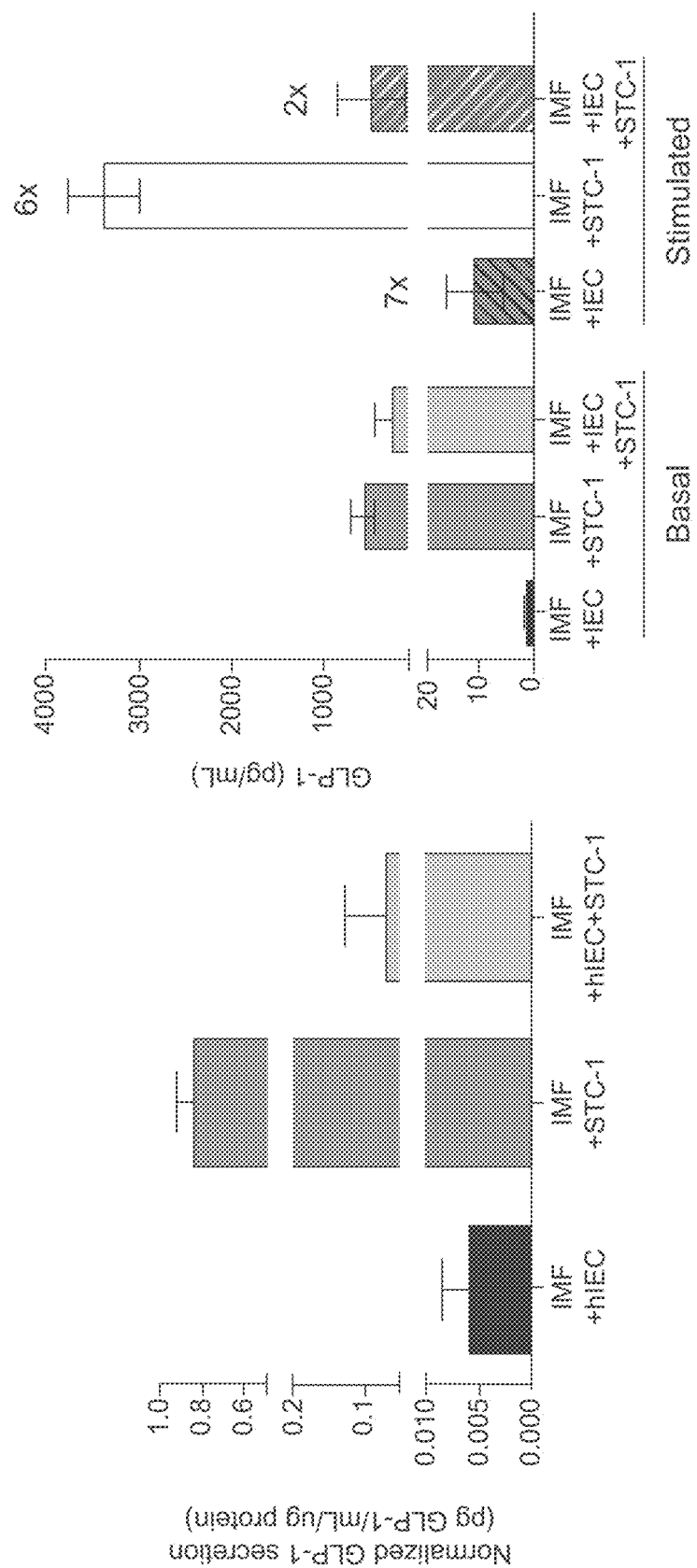
FIGS. 18A-18B are bar graphs showing GLP-1 secretion in 3D bioprinted tissues fabricated with primary intestinal epithelial cells. Tissues are measured for basal GLP-1 secretion after 2 hour starvation. Protein content is measured to normalize GLP-1 levels (FIG. 18A). Baseline GLP-1 secretion is enhanced by incorporation of mouse enteroendocrine cell line STC-1 and further enhanced by stimulation by a mixture of 50 mM Forskolin+10 uM IBMX+10 mM glucose post starvation (FIG. 18B). GLP-1 can be detected and induced in tissues without STC-1 cells suggesting enteroendocrine cells are present and functional in hIEC isolates.
Figure 20A:
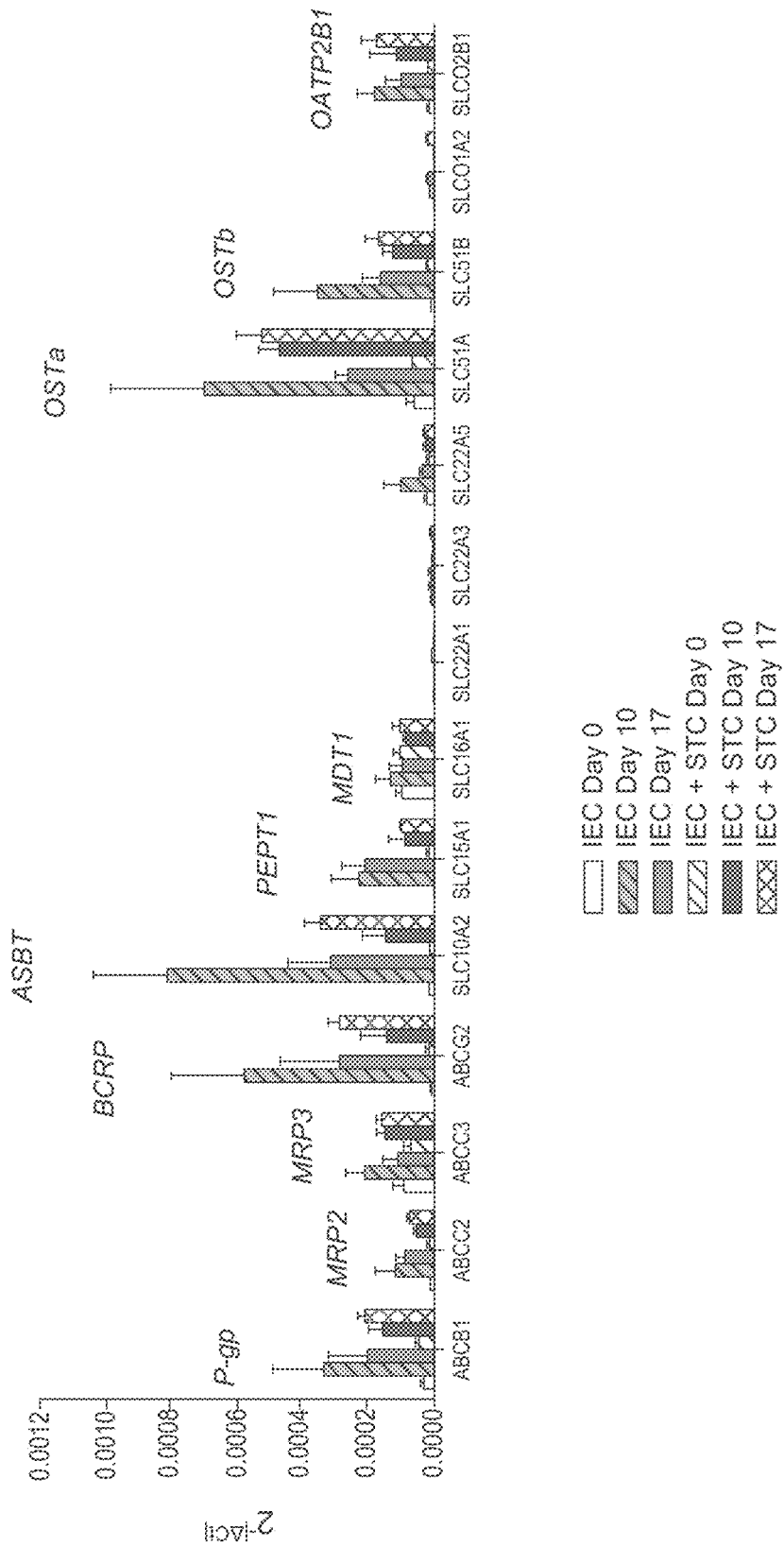
FIGS. 20A-20E are graphs showing Taqman array card analysis.
Figure 20B:
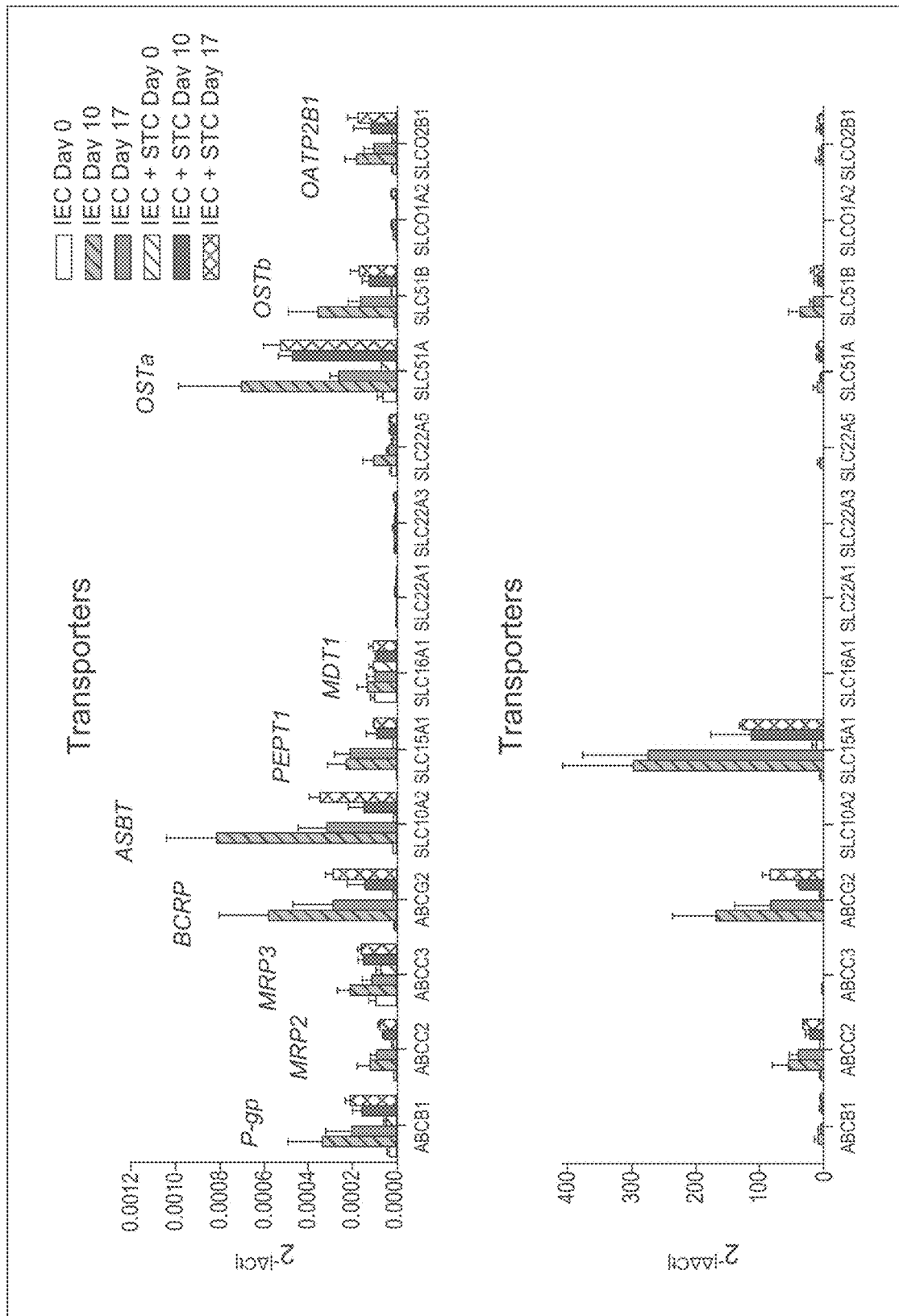
Figure 20C:
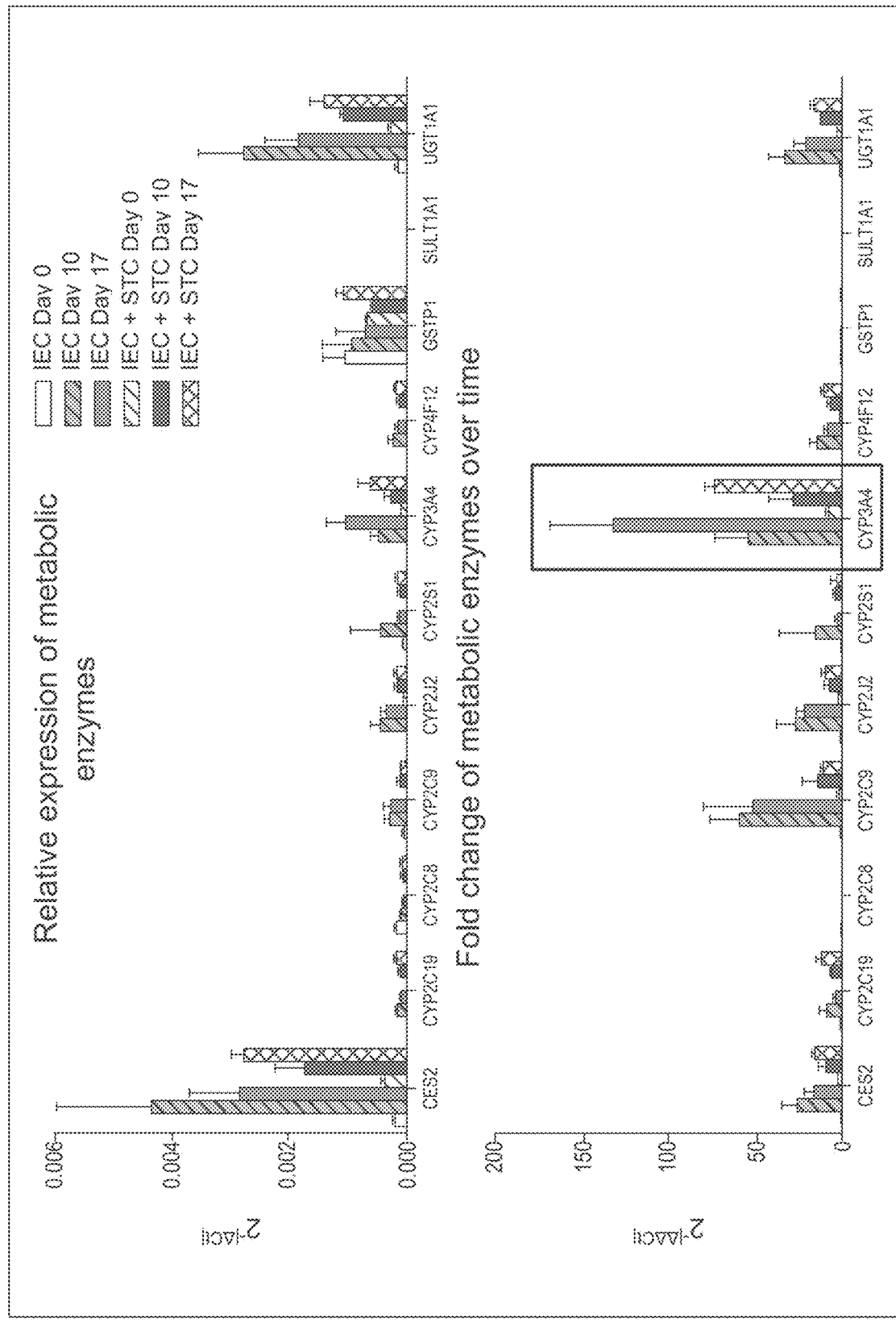
Figure 20D:
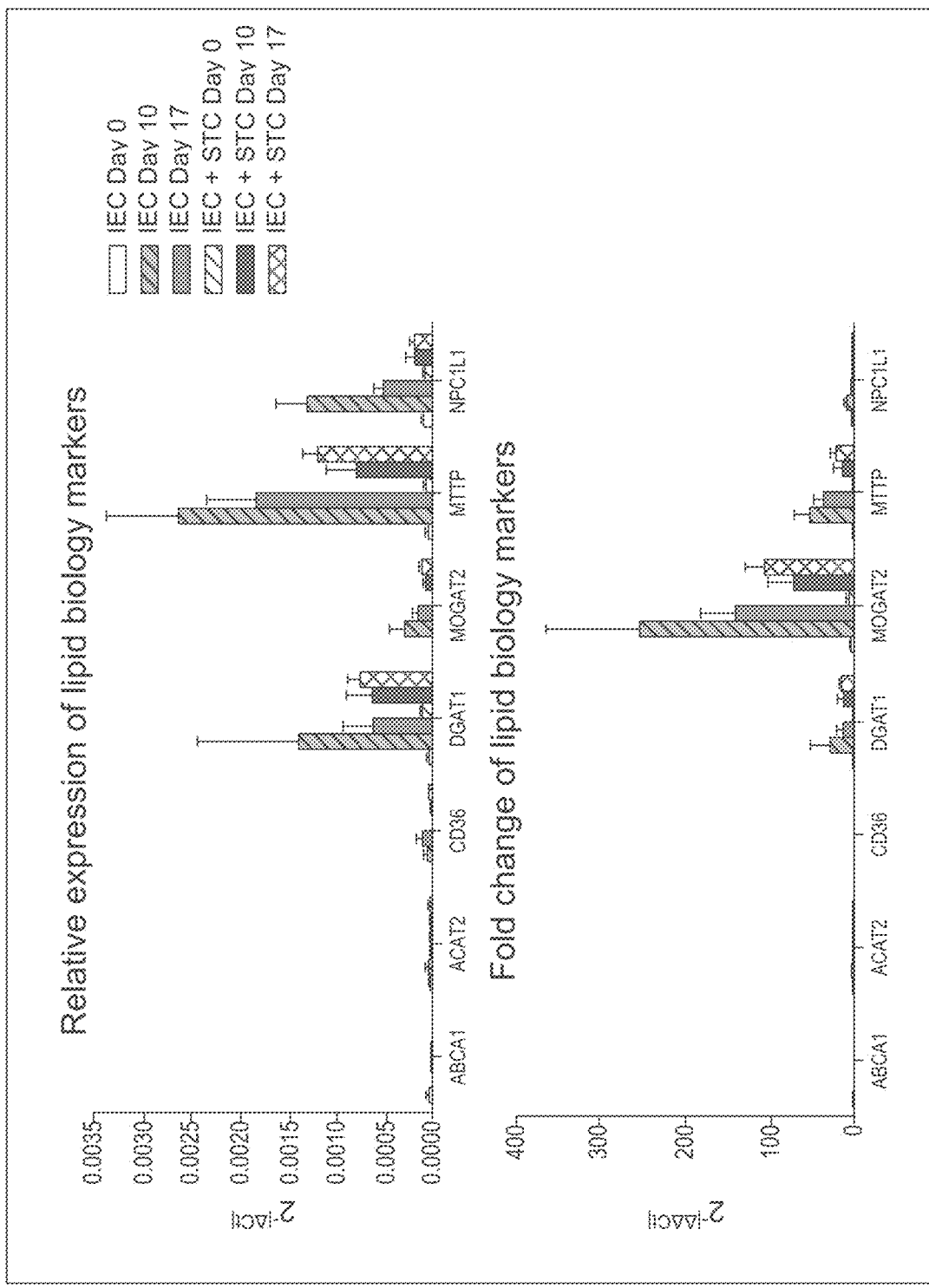
Figure 20E:
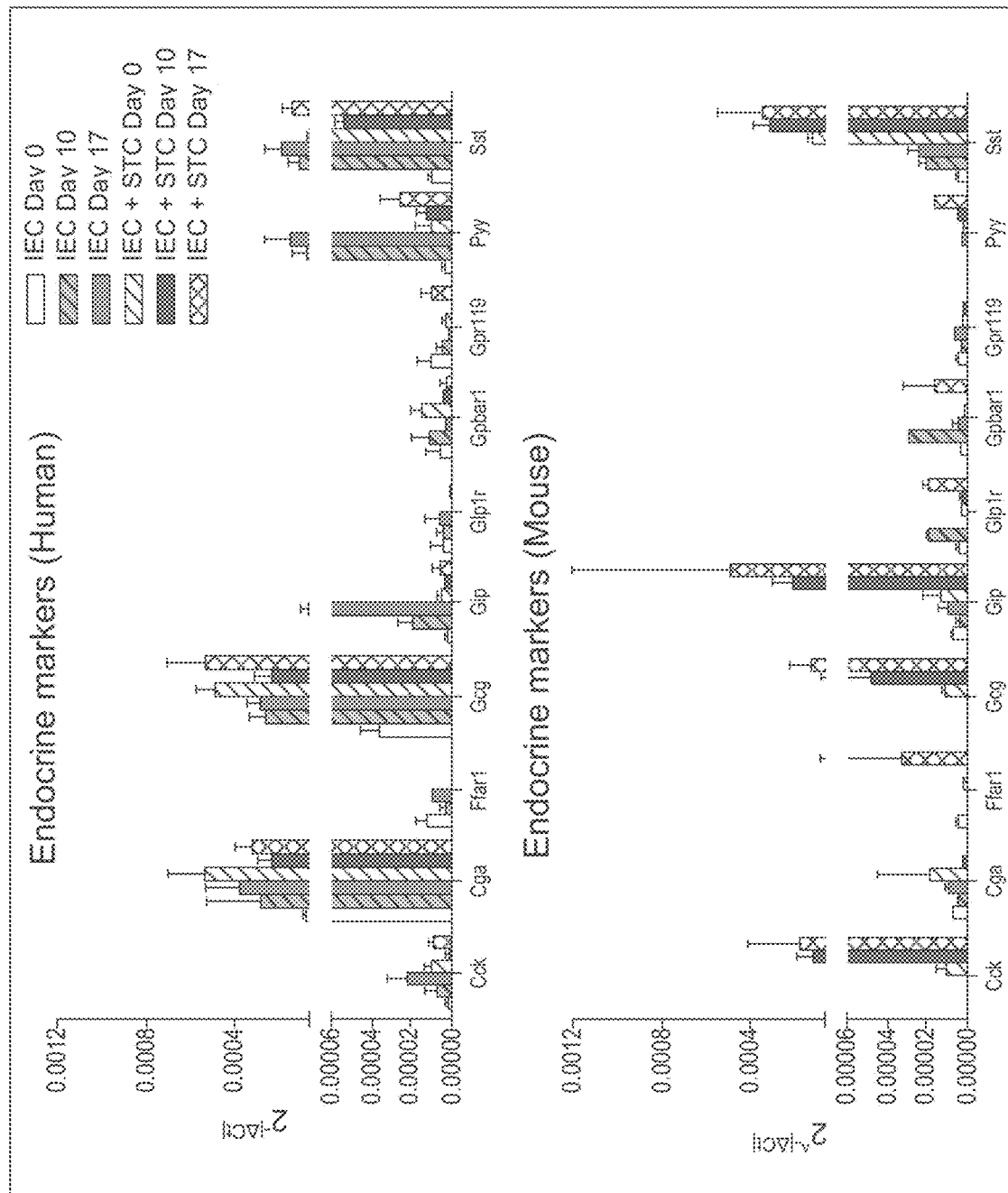

GLP-1 secretion was detected at basal levels in 3D printed tissues. GLP-1 secretion was augmented by the presence of STC-1 cells as expected. Secretion was further augmented by stimulation with a cocktail of known GLP-1 stimulants including glucose, forskolin, and IBMX, as expected. What was unexpected was that the primary intestinal epithelial cells alone can produce GLP-1. This indicates that enteroendocrine cells are not only present but functional, and supports histological staining that shows CHGA positive cells in tissue epithelium. What was also unexpected was that the GLP-1 secretion from primary cells can also be stimulated in the absence of STC-1 cells. This indicates that enteroendocrine cells are present in tissues with primary intestinal epithelial cells, that they are functional, and that function is inducible. (FIGS. 18A-18B)

Barrier function was also demonstrated in tissues fabricated with primary intestinal epithelial cells. Barrier function was measured by both TEER and Lucifer yellow permeability. It is important to note that barrier formation in this model requires the presence of primary intestinal epithelial cells which would stain positive for cytokeratin 18. The data shows that the interstitial layer (IMF) alone does not form a barrier, and that STC-1 cells do not form a barrier. Incorporation of 1% STC-1 cells into the primary cell epithelium does not disrupt the barrier but may increase tissue variability. This data was consistent with the E-cadherin staining shown histologically. E-cadherin is a tight junction marker and is required for barrier formation, and was only present in tissues with primary intestinal epithelial cells. (FIGS. 19A-19C)

Gene expression panel in Taqman array card shows that key genes were present and induced over 17 day time course as tissues mature and differentiate in culture. Gene expression patterns are clustered in heat map by biological replicate indicating that tissues are highly reproducible (n=3 biological replicates per group). 2 separate experiments are compared; one with only primary intestinal epithelial cells, one with both primary intestinal epithelial cells and 1% STC-1 cells and showed similar trends. This indicated that experimental results are reproducible between experiments, again supporting the reproducibility of bioprinted gut tissues.

Taqman array showed that key transporters, Phase I and Phase 2 metabolic enzymes, lipid biology markers, and enteroendocrine markers were present and upregulated. Again, it is important to note that expression of key transporters and metabolic enzyme CYP3A4 is superior in tissues fabricated with primary cells to those fabricated with Caco-2 cells. They are highly expressed and increase as tissues mature in culture. It is also important to note that key endocrine genes are present in tissues that lack STC-1 cells and increase with time in culture. The endocrine genes again support the presence of enteroendocrine cells in the primary intestinal epithelial cells and that these cells may be capable of multiple functions including CCK, PYY, and SST secretion in addition to GLP-1 secretion demonstrated previously. (FIGS. 20A-20E)

Figures 21A, 21B:
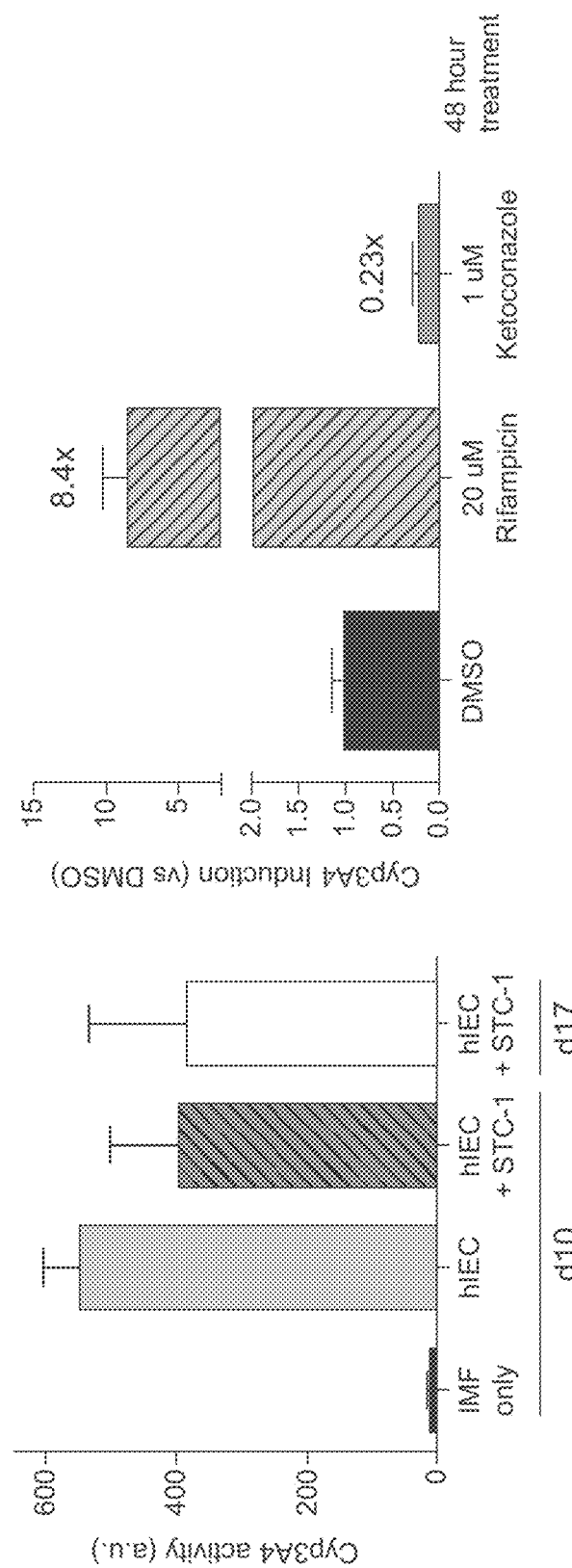
FIGS. 21A-21B show that 3D gut tissues have sustained CYP3A4 function that can be modulated by drugs. CYP3A4 activity is specific to primary intestinal epithelial cells. Constructs maintain functional CYP3A4 activity for >2 weeks in culture (FIG. 21A). Significant CYP3A4 activity can be induced with Rifampicin and inhibited with Ketoconazole as predicted (FIG. 21B).

Metabolic enzyme CYP3A4 was not only expressed, but enzymatically functional for a period of at least 17 days. This functional activity was a key and unexpected finding because it not only shows that the tissues were metabolically competent for greater than 2 weeks, but highlights an endpoint that cannot be achieved with the current gold standard Caco-2 model (Caco-2 tissues lack CYP3A4 expression). Furthermore, well established drugs that are known to stimulate (Rifampicin) and inhibit (Ketoconazole) CYP3A4 activity in native intestine also functioned in a similar manner in the 3D bioprinted intestinal tissue model. Caco-2 cells cannot demonstrate drug-induced CYP3A4 activity. In addition, this CYP3A4 function was unexpectedly seen for greater than 14 days without the presence of fluid flow or mechanical stimulation, suggesting that neither is a requirement for recapitulation of physiologic function in the intestinal tissues. The MDCK cell line is often used as a surrogate in vitro for drug metabolism studies but these are canine and kidney cells, and therefore a completely different system. (FIGS. 21A-21B)

Example 4

A Bioprinted Three-Dimensional Intestinal Tissue Model

A human intestinal tissue construct was fabricated by bioprinting with 100% human adult primary intestinal cells by continuous deposition using interstitial bio-ink containing collagen followed by deposition of epithelial suspension.

Bio-ink was generated by a cellular mixture of 100% primary adult human intestinal myofibroblasts (IMF) in 100% bovine type I collagen at a concentration of 20 million cells per milliliter (20M/mL). Three-dimensional bio-ink constructs were printed by continuous deposition using the Novogen MMX Bioprinter® in a base layer to create an interstitial structure. One tissue was printed per transwell in a 24 well plate. The transwell printing surface contained a polytetrafluoroethylene (PTFE) membrane coated with equimolar mixture of types I and III collagen (bovine) with pores 3 um in size. Following printing, tissues were allowed to mature for 4 days in a humidified 37° C. incubator in 100% IMF media and media was changed daily. After incubation, interstitial tissue constructs were removed from the incubator and placed in a BSC hood. Media was aspirated immediately before application of epithelial cells. Epithelial cells were dispensed as a cell suspension of 100% primary adult human intestinal epithelial cells onto the printed interstitial layer. Media used contained 100% primary intestinal epithelial cell growth media. In some wells no epithelial cells were added to the printed IMF layer and these wells were used as a control for comparison studies. After deposition, tissues were then cultured in 3D intestinal media comprising of Advanced DMEM/F12 (Thermo Fisher Scientific, Waltham, MA) with supplements. Media was changed everyday for up to 21 days.

To show the technical advancements of the bioprinted three-dimensional intestinal tissue model over Caco-2 monolayers. Caco-2 monolayer studies were also conducted. Briefly, cells were seeded at 30,000 cells/cm2 per well onto standard 24-well Transwell) permeable supports and cultured at air-liquid interface in DMEM with L-glutamine (Gibco, Thermo Fisher Scientific, Waltham, MA)+10% FBS (VWR, Radnor, PA) with media changes every 48 hours. Monolayers were grown for 21 days then qualified for used by TEER (785±56 Ω*cm2).

Histological Characterization of the 3D Bioprinted Human Intestinal Tissue of Example 4.

Figures 22G, 22H, 22I:
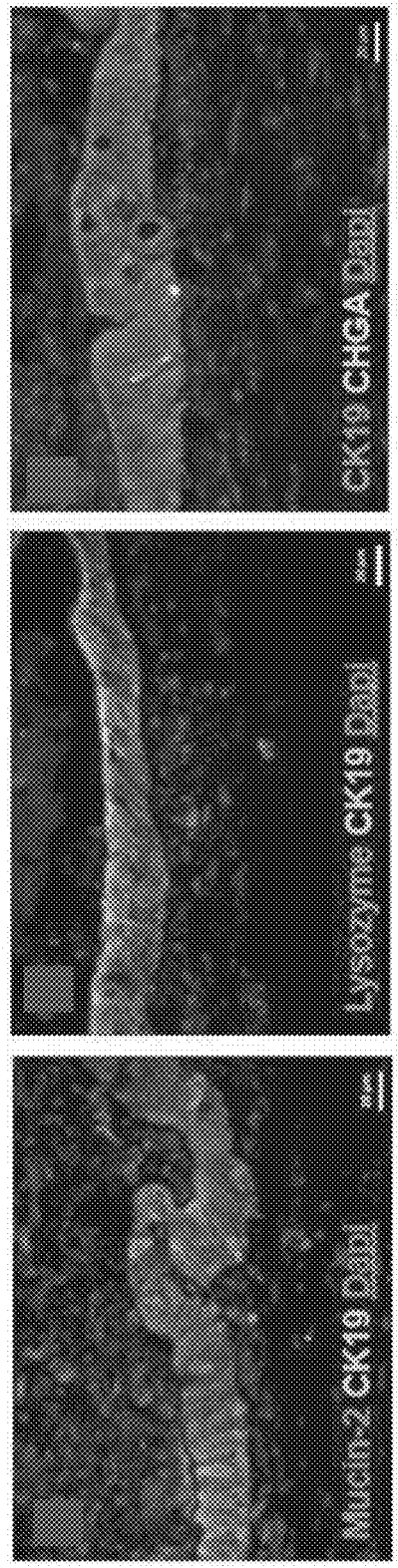

Histological characterization demonstrated a polarized epithelium with apical expression of villin, tight junction formation, and the presence of specialized epithelial cell types including goblet cells, Paneth cells, and enteroendocrine cells. The 3D bioprinted intestinal tissue of Example 4 was designed with bi-layered architecture, consisting of human intestinal myofibroblasts (IMF) supporting an epithelial layer containing human intestinal epithelial cells (hIEC). The 3D bioprinted intestinal tissue was fabricated with laminar architecture on transwell inserts (FIG. 22A) to enable access to both apical and basolateral surfaces for direct compound testing and analyzed histologically over a 17 day culture period. At day 17, tissues exhibited polarized columnar epithelial morphology and secondary structure formation (FIG. 22B). The epithelial and interstitial tissue compartments remained distinct, with correct expression of epithelial cell-specific marker CK19 confined to the epithelial layer and myofibroblast marker vimentin confined to the interstitium (FIG. 22C). Tight junction marker E-Cadherin, a key protein involved in barrier function, was uniformly expressed between epithelial cells of the hIEC layer (FIG. 22D). Correct polarization of the hIEC and brush border formation was seen by positive staining for brush border protein villin at the apical surface (FIG. 22E). Periodic acid-Schiff (PAS)/Alcian blue staining confirmed an apical brush border and suggested the presence of a subpopulation of goblet cells as well as the excretion of mucus (FIG. 22F). Immunohistochemistry for Mucin-2 confirmed the presence of goblet cells and mucus secretion, a feature indicative of normal intestinal function. The mucus entrapped cells sloughed off from the epithelium during normal cell-turnover over time in culture, resulting in cellular debris observed histologically (FIG. 22G). In addition to goblet cells, other specialized cell types of the intestinal epithelium critical for many responses to various biological stimuli were present within the epithelial layer of the 3D bioprinted intestinal tissue model, including lysozyme positive Paneth cells, and chromogranin expressing enteroendocrine cells (FIG. 22H-22I). Tissue architecture and expression of key cell markers was maintained for greater than two weeks in culture, with consistent expression patterning on the day 10 and day 17 time points analyzed, suggesting the model may be suitable for extended compound studies.

Figure 29:
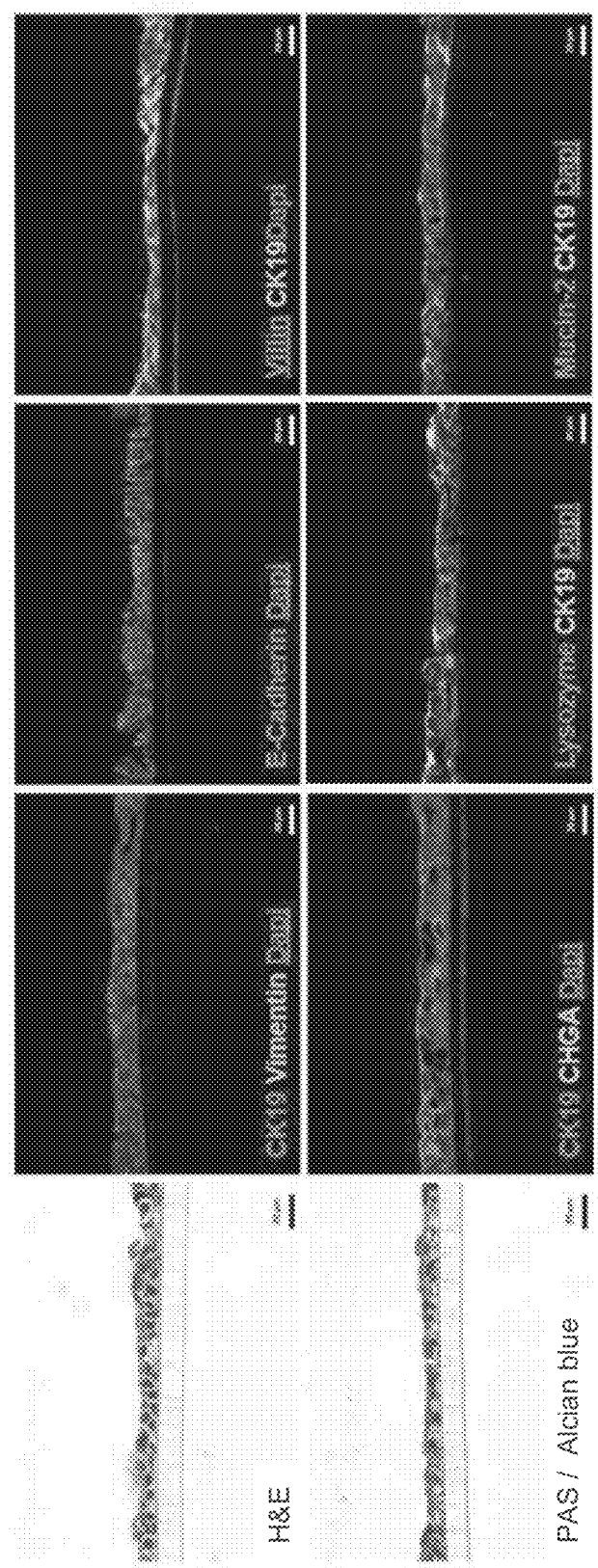
FIG. 29 shows Caco-2 histology. Day 21 monolayers of Caco-2 cells were stained for general and specialized cell subtype epithelial markers. Caco-2 express CK19, E-Cadherin, and villin across the monolayer. No staining was observed for chromogranin, lysozyme, or mucin-2.

The 3D bioprinted intestinal tissues were thicker in comparison to Caco-2 monolayer cultures and contained secondary structure formation in the epithelium absent in the monolayers. Although the Caco-2 cells appeared less columnar than the epithelium of the 3D bioprinted intestinal tissues, they expressed E-Cadherin and villin, confirming tight junction formation and the polarized epithelial phenotype. In contrast to 3D bioprinted intestinal tissues, however, subpopulations of specialized cells and evidence of mucus production were absent in the Caco-2 monolayers (FIG. 29). Characterization of Gene Expression of the 3D Bioprinted Human Intestinal Tissue of Example 4.

Figure 23A:
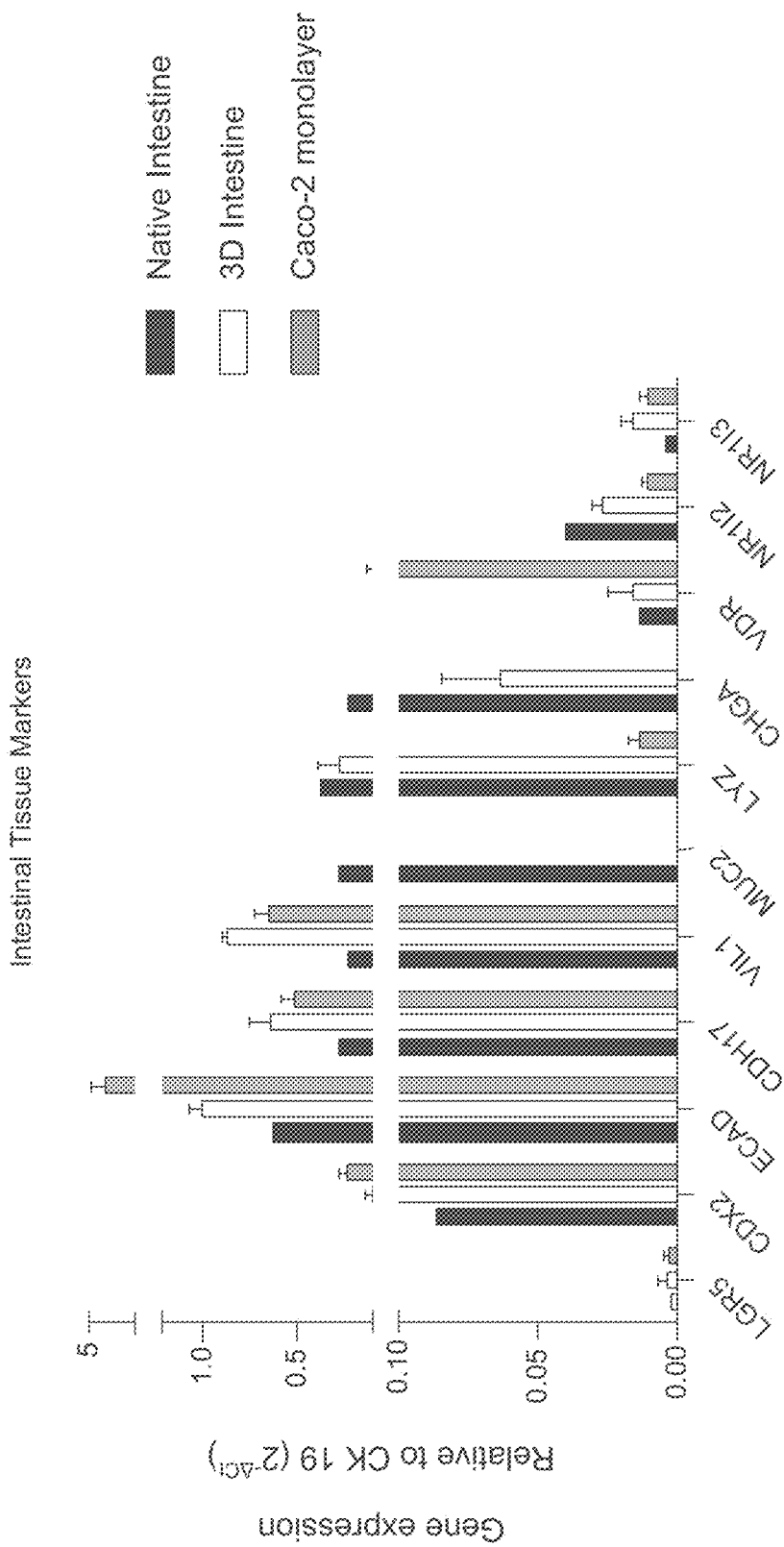
FIGS. 23A-23C show gene expression comparisons of native intestine, 3D bioprinted intestinal tissue, and Caco-2 monolayers.

Gene expression analysis was utilized to further evaluate expression of key intestinal epithelial tissue markers, metabolic enzymes, and transporters in the 3D bioprinted intestinal tissue over a 17 day culture period and compared to both native donor intestinal tissue and to standard Caco-2 monolayers (FIG. 23). To specifically study differential expression in the epithelium and to remove any variance in total cell number, genes were analyzed relative to expression of epithelial-specific marker CK19. Tight junction marker E-Cadherin (CDH1) was highly expressed in all samples. Although levels were comparable in 3D intestinal tissues and native tissue, E-Cadherin expression in Caco-2 monolayers was artificially high. In support of histological findings, markers for specialized cell subpopulations including Paneth cells (LYZ) and enteroendocrine cells (CHGA) were present in 3D bioprinted intestinal tissue and comparable to native donor tissue while Caco-2 monolayers lacked their expression. Although Mucin-2 cells were identified by immunohistochemical approaches (FIG. 22G) in the 3D bioprinted intestinal tissues, gene expression was decreased compared to native intestine. The majority of gene expression values in bioprinted tissues were within 2-fold of the donor intestinal tissue. Key xenobiotic-activated nuclear receptors involved in drug metabolism and disposition including VDR, PXR (NR1I2), and CXR (NR1I3) were also expressed in 3D bioprinted intestinal tissue and at comparable levels to native intestine. In contrast, Caco-2 exhibited abnormally high expression of VDR and low expression of NR1I2 (FIG. 23A).

Figure 23B:
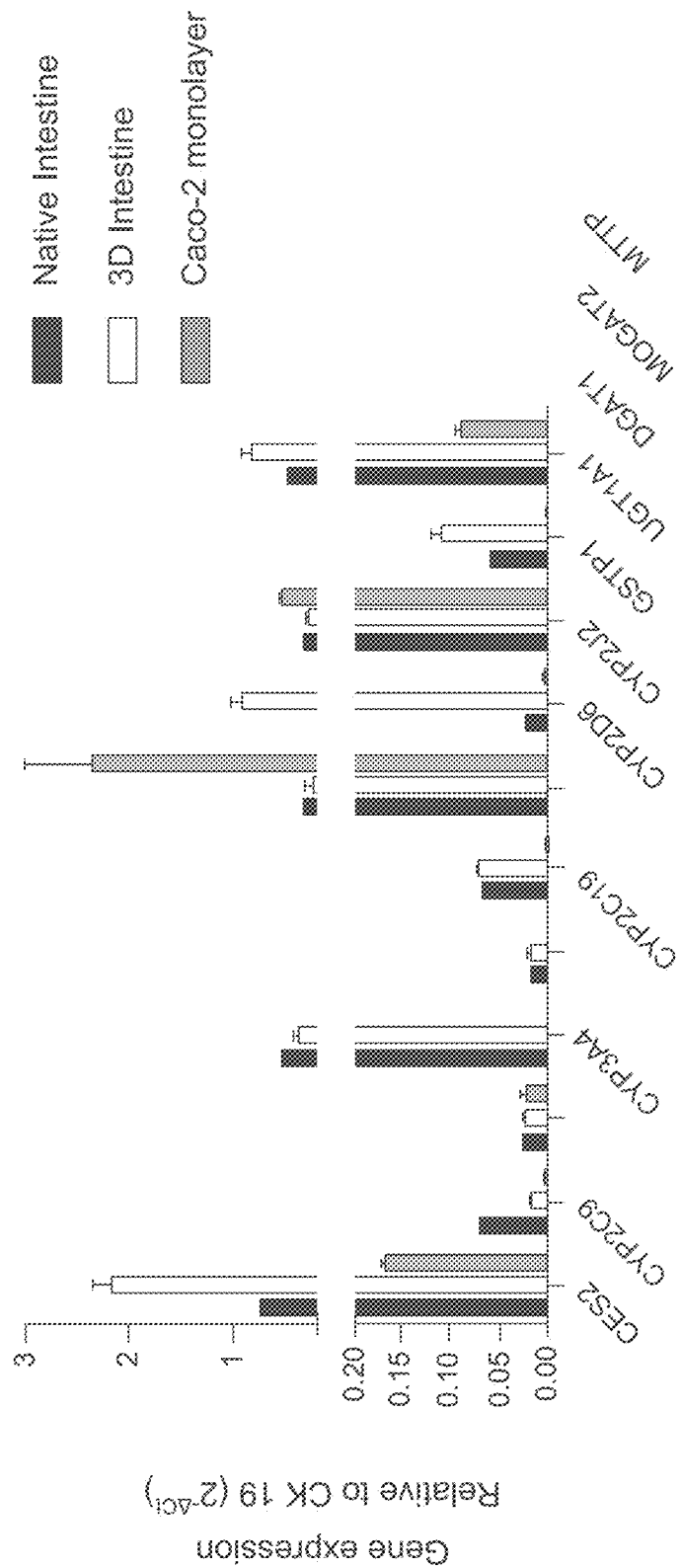
Figure 23C:
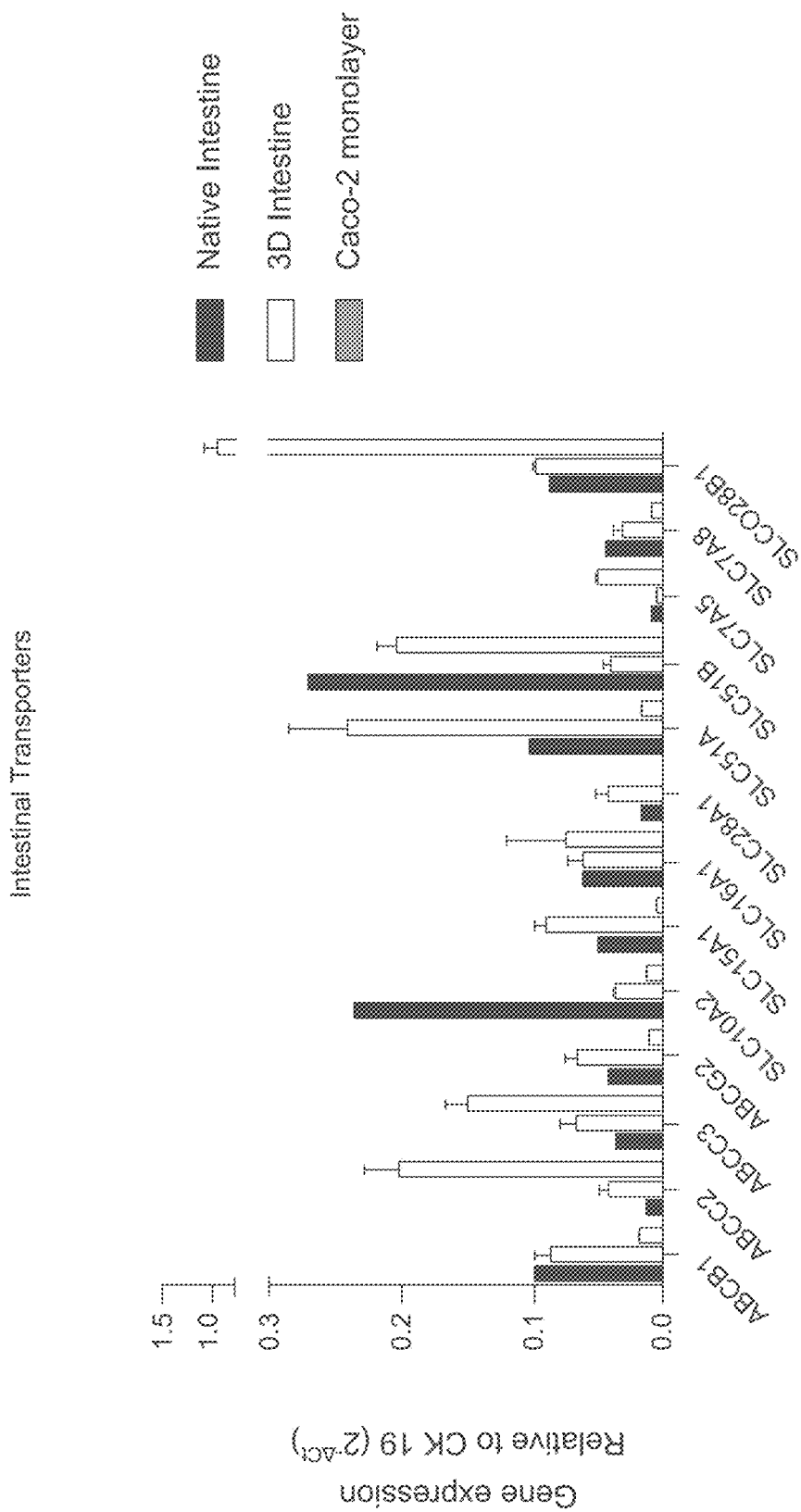

Major intestinal Phase I P450 metabolic enzymes including CYP3A4, CYP2C9, CYP2C19, CYP2D6, and CYP2J2 were detected in the 3D bioprinted intestinal tissue. Clinically important CYP3A4 was highly expressed in the 3D bioprinted intestinal model at levels similar to native tissue, while expression was absent in Caco-2 monolayers. CES2, a major biotransformation enzyme involved in hydrolysis, was also highly expressed in both native intestine and 3D intestinal tissue but at a much lower level in Caco-2 monolayers. Key intestinal Phase II metabolic enzymes GSTP1 and UGT1A1 were expressed by 3D bioprinted intestinal tissues as well as transcripts for fatty acid metabolism, including DGAT1, MOGAT2, and MTTP (FIG. 23B). Intestinal efflux and uptake transporters can be both sites of drug-drug interaction and limiting factors for drug absorption. Major efflux transporters P-gp (ABCB1, MDR1) and BCRP (ABCG2) and key uptake transporters PEPT1 (SLC15A1) and OATP2B1 (SLCO2B1) are expressed in 3D bioprinted intestinal tissues with levels comparable to native intestine (FIG. 23C). Intestinal bile acid related transporters ASBT (SLC10A2), OSTa (SLC51A), and OSTb (SLC51B) were also detected. Interestingly in Caco-2 monolayers, many important metabolic enzymes and transporters analyzed were reduced, overexpressed or absent, suggesting that the bioprinted model more closely resembles normal tissue function than the Caco-2 monolayer.

Characterization of Barrier Function of the 3D Bioprinted Human Intestinal Tissue of Example 4.

The 3D bioprinted intestinal tissue of Example 4 developed physiological barrier function and correctly distinguished between high and low permeability compounds. The intestine is a selectively permeable barrier, regulating absorption of both nutrients and xenobiotics. Transepithelial electrical resistance (TEER) was utilized to measure barrier function in 3D bioprinted intestinal tissues over a 21 day culture period. Measurements demonstrated that the tissues developed and maintained barrier function between days 10 and 21 of culture, exhibiting values within a physiological range (50-100 $\Omega*cm2$) comparable to normal human intestine function [20] (FIG. 24|A). In contrast, Caco-2 monolayers demonstrated much greater TEER measurements (785±56 $\Omega*cm2$), values significantly higher than normal human tissue function.

Figure 24B:
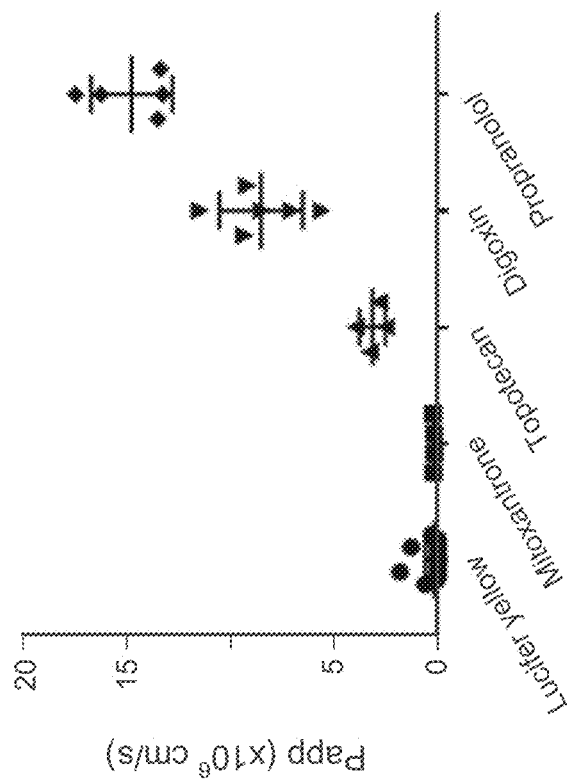
FIGS. 24A-24B show barrier function of 3D bioprinted intestinal tissue.
Figure 24A:
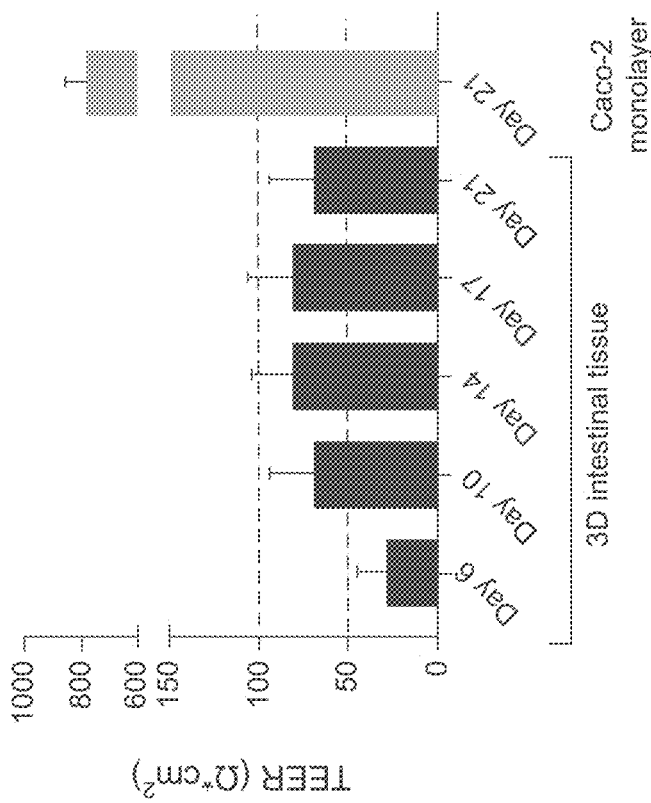

Representative compounds with high and low permeability were used to further validate 3D bioprinted intestinal tissue barrier function (FIG. 24B). Paracellular transport marker Lucifer yellow correctly demonstrated low permeability, suggesting the presence of an intact physical barrier for drug transport. The 3D bioprinted intestinal tissues correctly distinguished between low permeability mitoxantrone, a prototypical substrate for the ABCG2 (BCRP) efflux transporter and higher permeability propranolol, a passive transcellular transport reference compound.

Transporter Localization and Function in the 3D Bioprinted Intestinal Tissue Model of Example 4.

Figure 31:
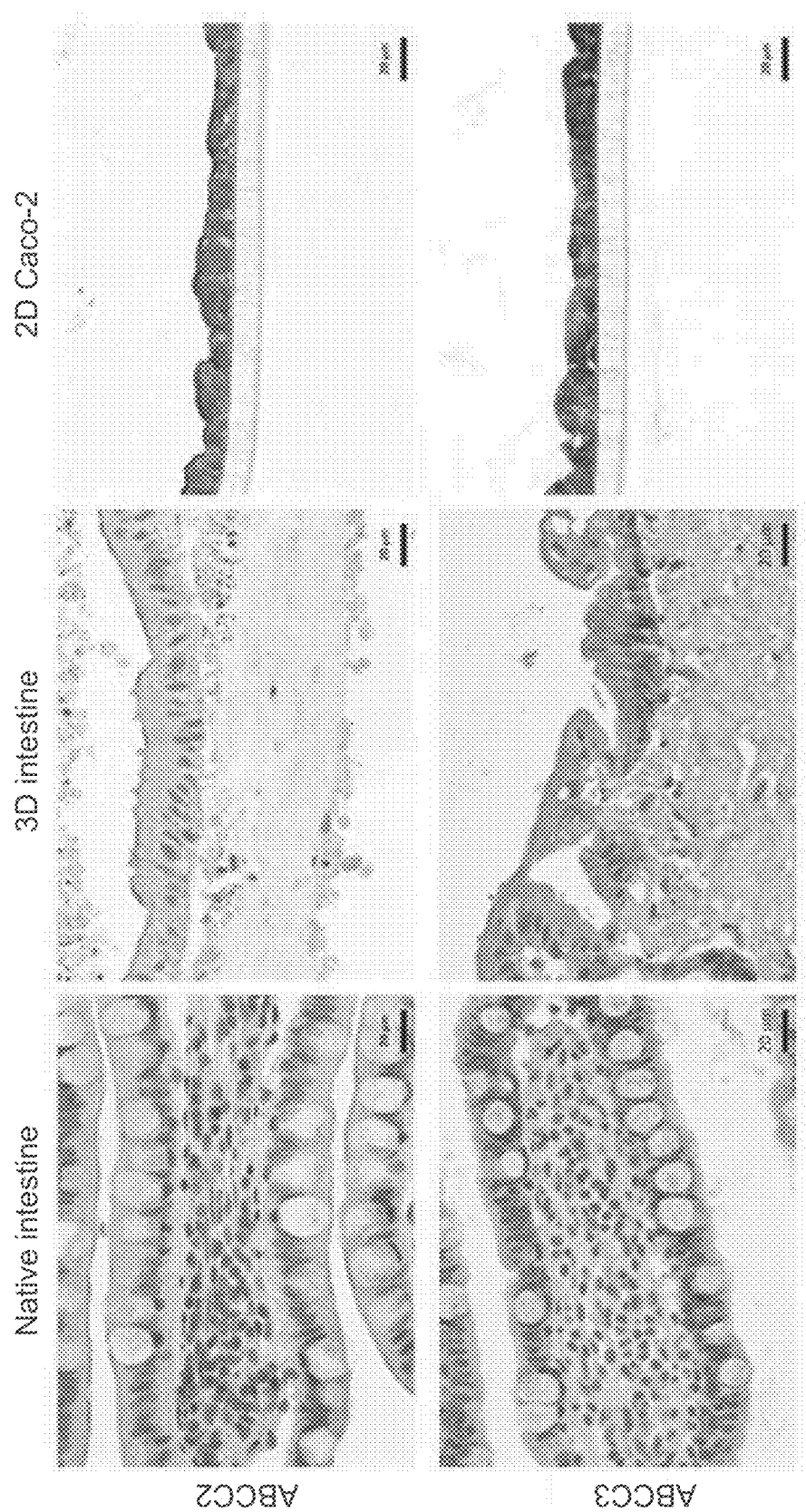
FIG. 31 shows MRP2 and MRP3 transporter expression. Native intestine, 3D bioprinted intestinal tissue, and Caco-2 monolayers were compared for expression of MRP2 (ABCC2) and MRP3 (ABCC3). Similar levels of MRP staining were observed between normal intestine tissue and 3D bioprinted intestinal tissue with higher levels seen in Caco-2 monolayers.

Immunohistochemical staining was used to confirm the correct polarized expression patterning of key efflux transporters P-gp (ABCB1, MDR1) and BCRP (ABCG2) at the apical surface. Staining demonstrated that expression was continuous across the apical surface similar to native tissue, whereas apical expression in Caco-2 cells appeared in patches across the monolayer (FIGS. 25A-25B). Histological staining also confirmed correct apical MRP2 and basolateral MRP3 expression patterning in 3D bioprinted intestinal tissues similar to native intestine. In contrast, Caco-2 monolayers appeared to overexpress MRP2 and MRP3 transporters consistent with gene expression data (FIG. 31).

Figure 25C:
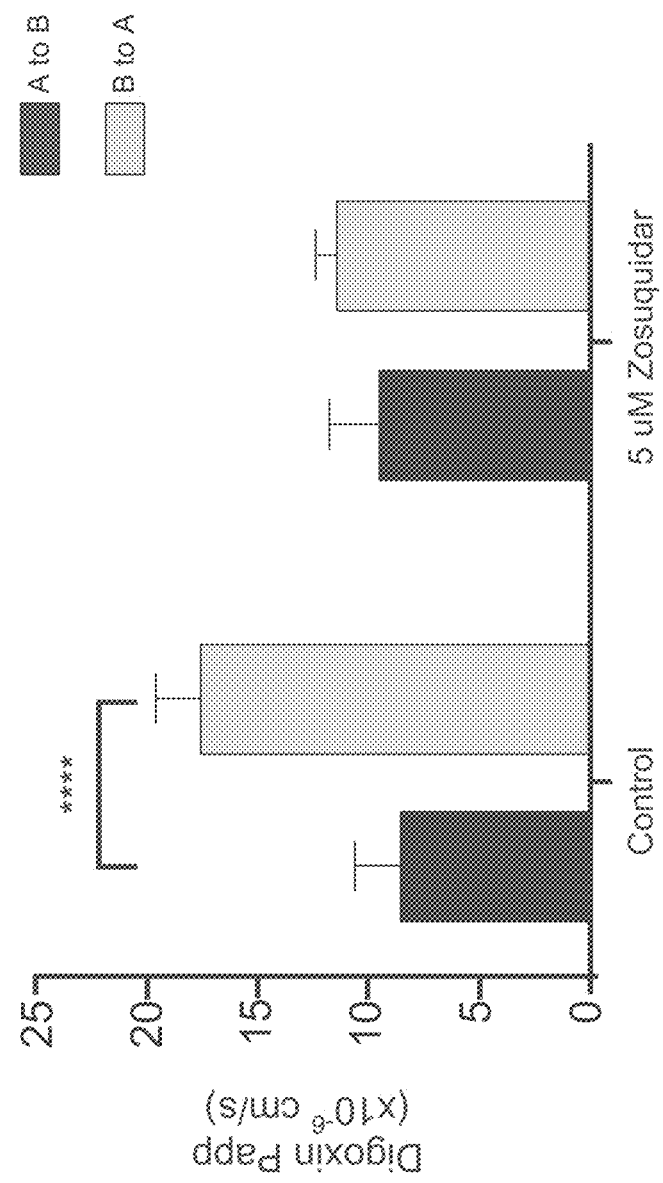
Figure 25D:
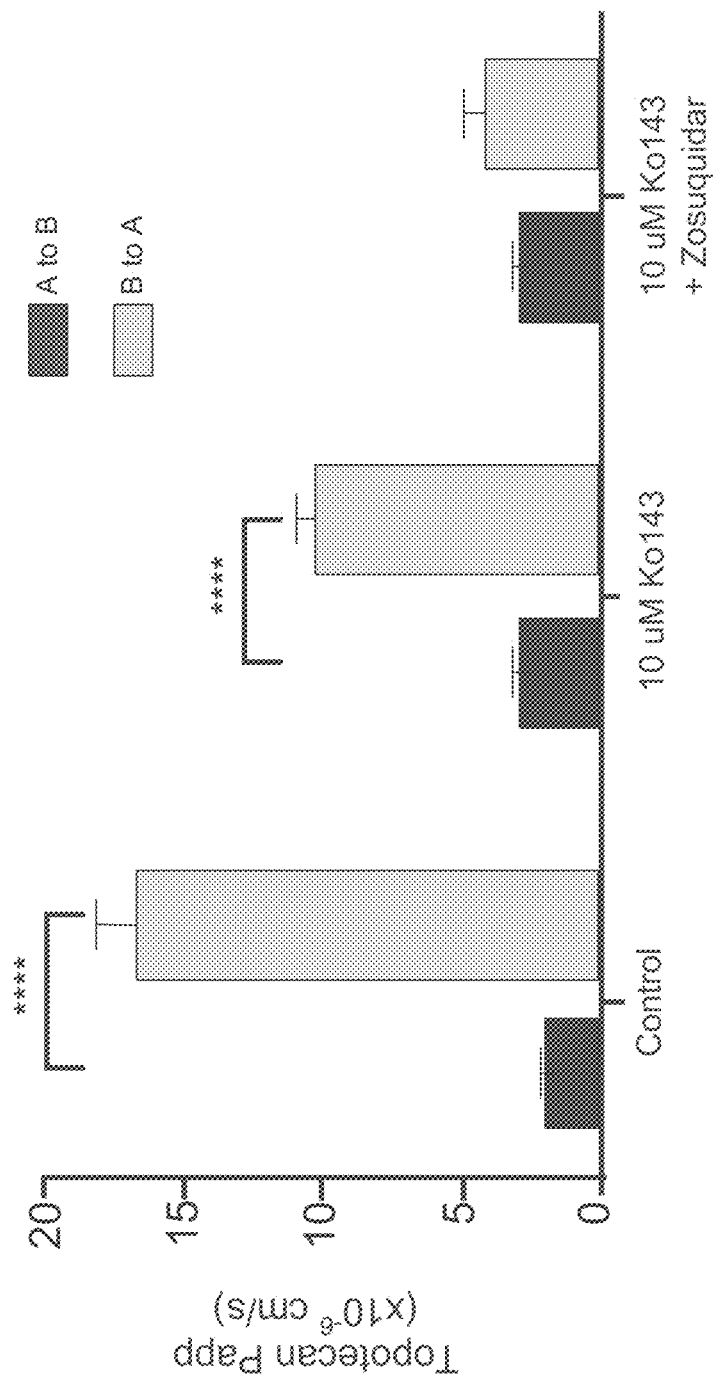
Figure 30:
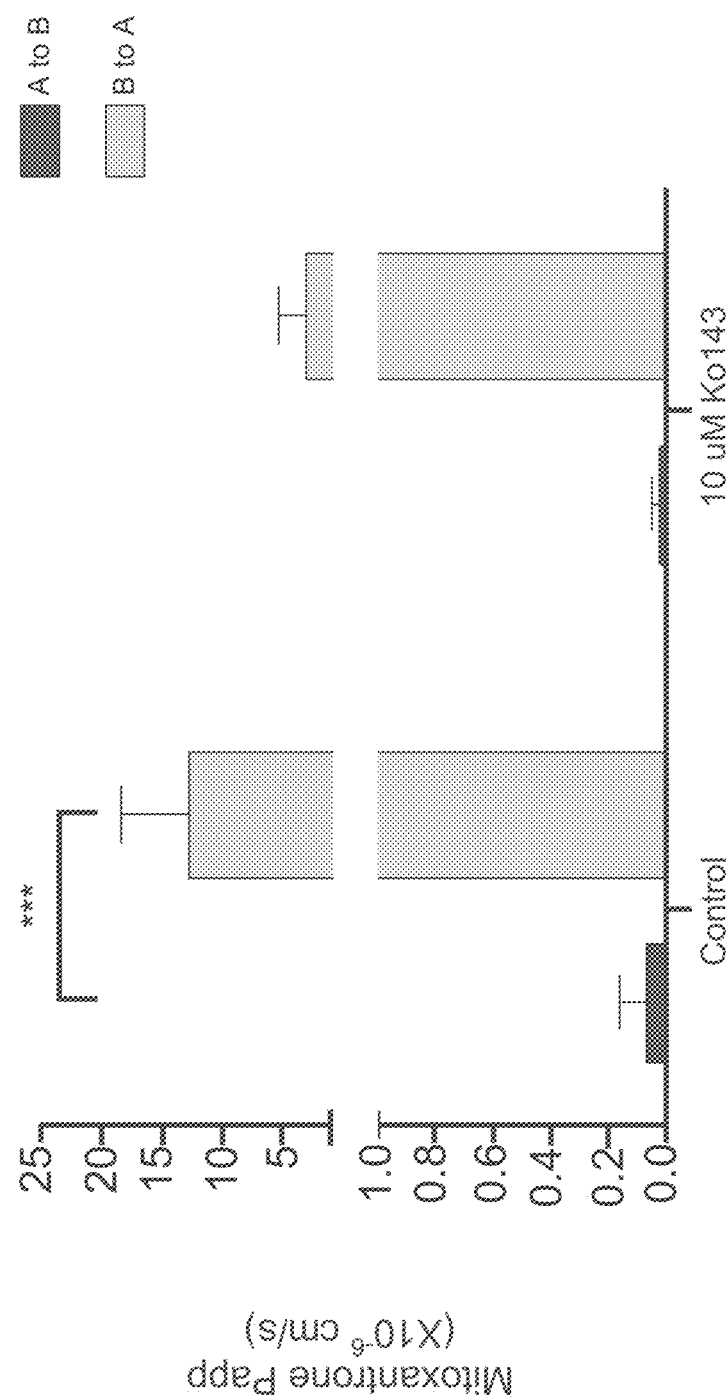
FIG. 30 shows BCRP efflux of Mitoxantrone. Low permeability A to B of mitoxantrone, a BCRP substrate, was observed with much higher permeability in the B to A direction, efflux ratio=190. In the presence of BCRP inhibitor Ko143. Mitoxantrone permeability B to A decreased and efflux ratio reduced to 145. Note: samples for A to B were near or below limit of detection. (n=4) Level of significance: ***$P<0.001$ by two-way ANOVA.

Assessing bi-directional transport enables prediction of whether a compound undergoes active efflux. P-gp and BCRP function were tested in the 3D bioprinted intestinal tissue model by measuring bi-directional transport with and without inhibition (FIG. 25C). Under control conditions, asymmetric permeability of P-gp substrate Digoxin was observed with an efflux ratio greater than 2. Inhibition of P-gp by Zosuquidar decreased the rate of B to A transport, reducing the efflux ratio to 1.2, and confirming the activity of P-gp in 3D bioprinted intestinal tissue. BCRP function was confirmed by efflux of topotecan (FIG. 25D) and mitoxantrone (FIG. 30). BCRP/P-gp substrate Topotecan and BCRP substrate mitoxantrone were preferentially transported in the B to A direction with efflux ratios of 8.8 and 129, respectively. Furthermore, subsequent inhibition of topotecan transport by BCRP inhibitor Ko143 reduced the efflux ratio to 3.6 and dual inhibition with Ko143 and Zosuquidar further decreased efflux ratio to 1.4. Collectively, these results demonstrate that the 3D bioprinted intestinal tissue model expresses clinically relevant P-gp and BCRP transporters with proper localization and function.

Demonstration of Cytochrome P450 Metabolic Function in the 3D Bioprinted Intestinal Tissue Model of Example 4.

Figure 26A:
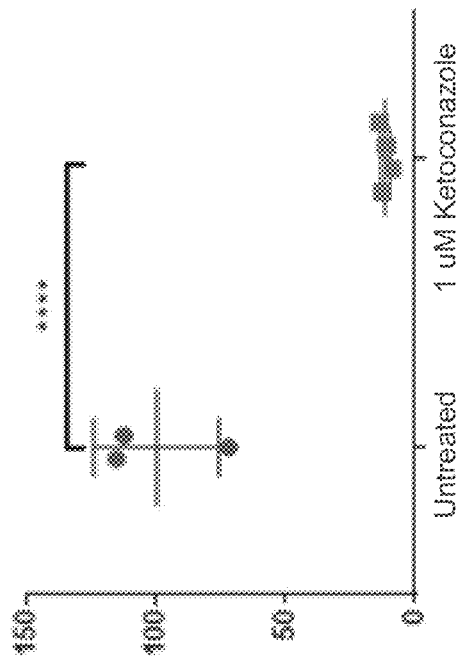
FIGS. 26A-26E show cytochrome P450 metabolism in 3D bioprinted intestinal tissue.
Figure 26B:
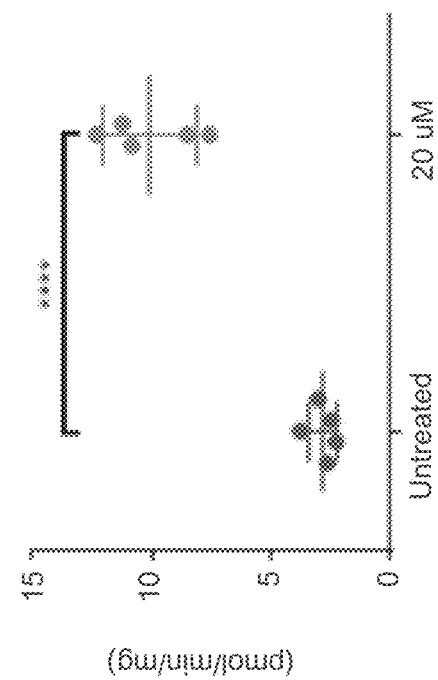
Figure 26C:
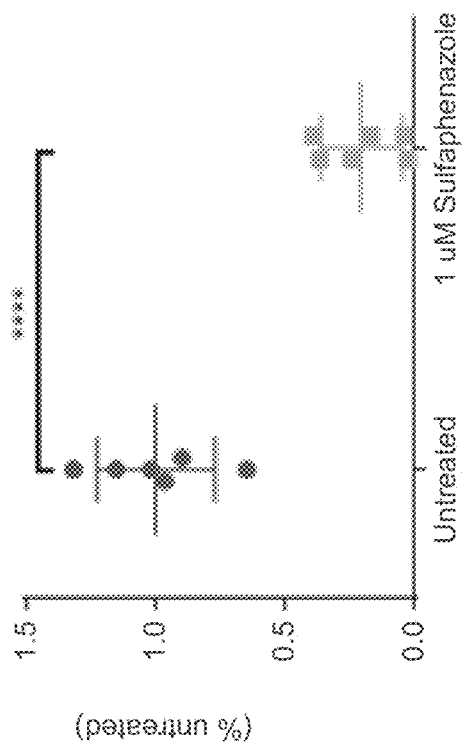
Figure 26D:
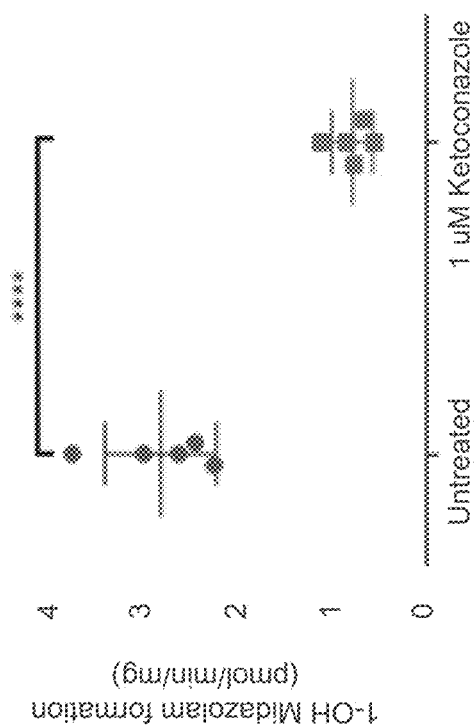
Figure 26E:
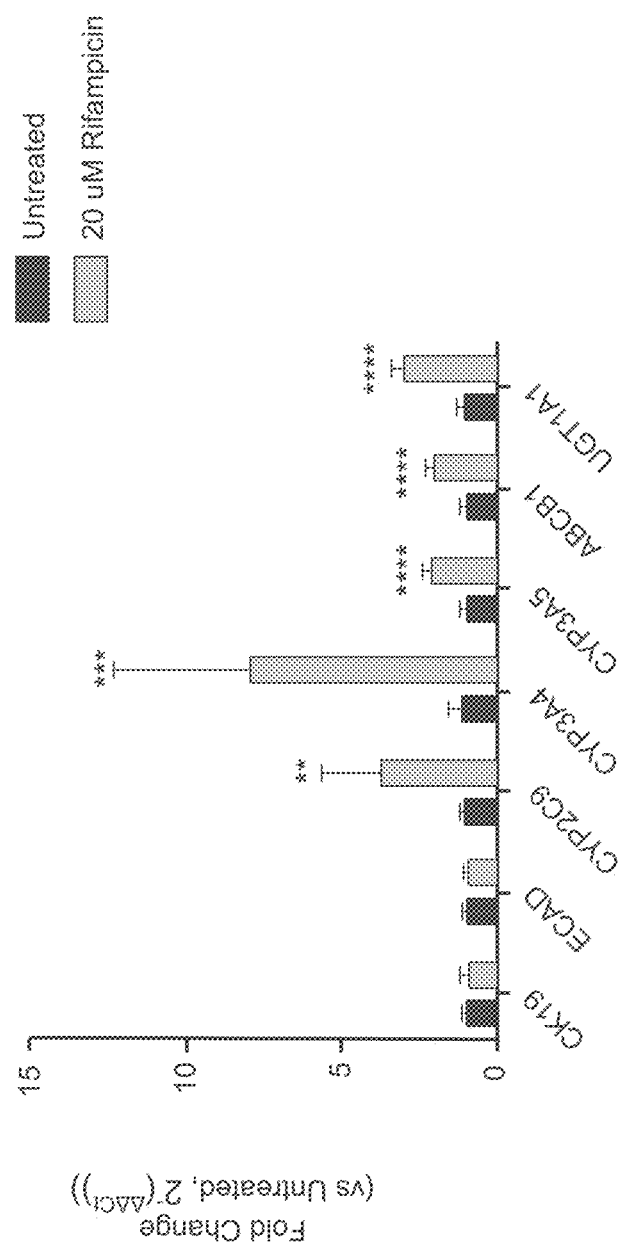

Gene expression analysis identified expression of key intestinal cytochrome P450 enzymes CYP3A4 and CYP2C9 in 3D bioprinted intestinal tissues (FIG. 23B). Functional assays were performed on CYP3A4 and CYP2C9 to confirm their activity and specificity (FIG. 26). CYP2C9 activity was readily detected in 3D bioprinted intestinal tissue by luminogenic P450 substrate conversion and could be significantly inhibited by sulfaphenazole (FIG. 26A). CYP3A4 activity and specific inhibition by ketoconazole was confirmed by both a luminogenic P450 substrate conversion (FIG. 26B) and by Midazolam metabolite formation (FIG. 26). Rifampicin treatment was associated with significantly higher turnover of Midazolam in treated tissues and significant upregulation in gene expression of PXR-inducible genes including CYP2C9, CYP3A4, CYP3A5, P-gp, and UGT1A1 while epithelial marker genes CK19 and ECAD remained stable (FIG. 26D-26E). Comparison of CYP3A4 activity for three separate sets of 3D bioprinted intestinal tissues fabricated from three separate donors showed consistency of ketoconazole inhibition and Rifampicin induction between donors despite expected interindividual variation in basal CYP3A4 activity (FIG. 32).

Characterization of the 3D Bioprinted Intestinal Tissues (Example 4) as a Model for Gastrointestinal Toxicity.

Figure 27A:
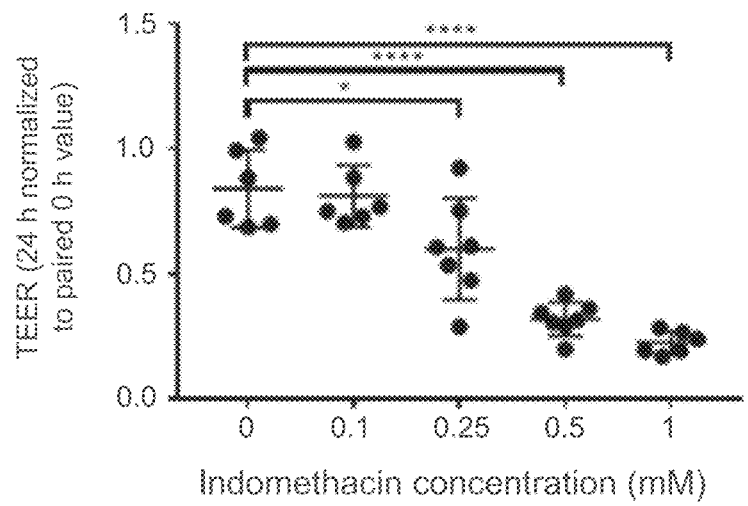
FIGS. 27A-27D show indomethacin toxicity in 3D bioprinted intestinal tissue.
Figure 27B:
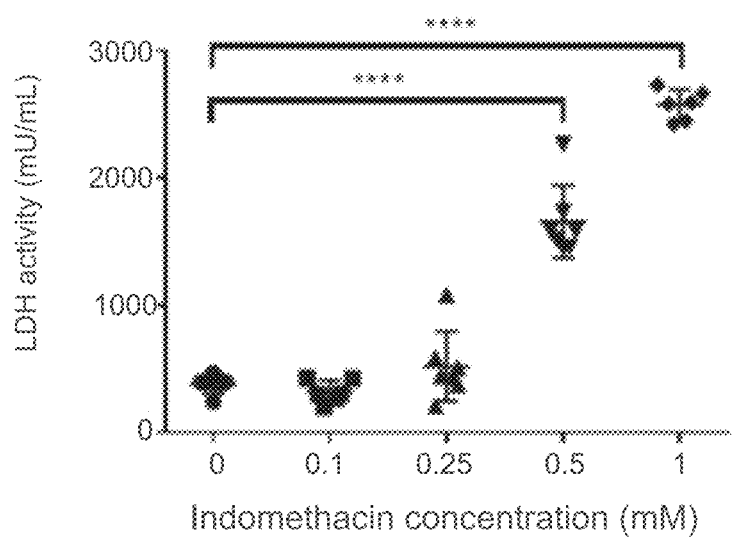
Figure 27C:
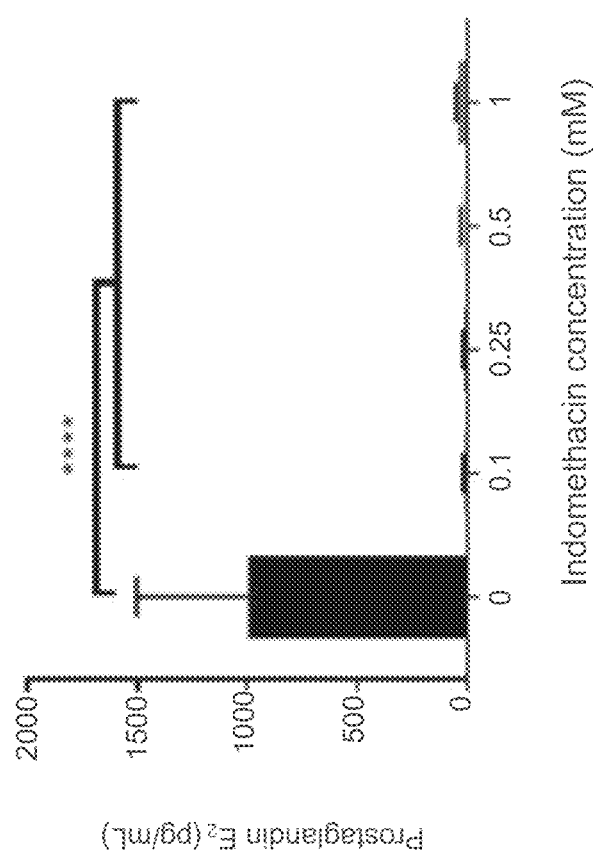
Figure 27D:
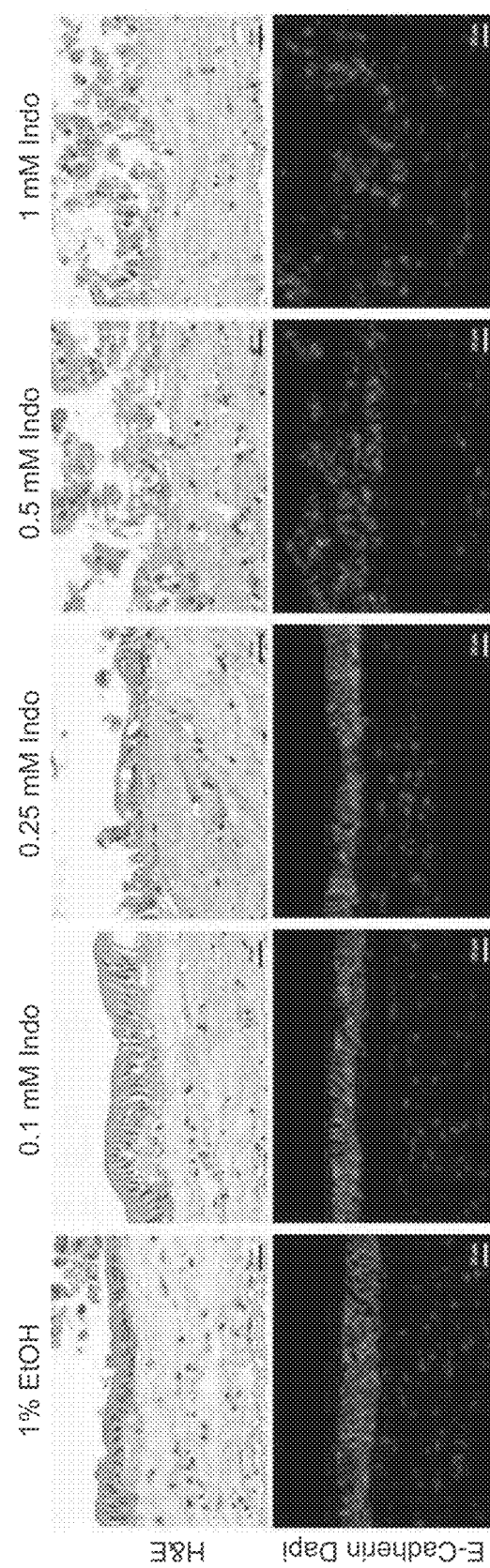

The utility of the 3D bioprinted intestinal model for compound toxicity applications was evaluated by the NSAID indomethacin, a prostaglandin $E_2$ (PGE2) oxygenase inhibitor and known GI toxicant that results in reduced intestinal epithelial barrier function through enterocyte apoptosis and necrosis. The 3D bioprinted intestinal tissue showed a dose-dependent decrease in barrier function as measured by TEER in response to 24 hour treatment (FIG. 27A). Injury to the intestinal cells was detected by LDH release and was significantly increased in the presence of indomethacin doses above 0.25 mM (FIG. 27B). Demonstrated inhibition of prostaglandin $E_2$ synthesis in the presence of indomethacin supported known the mechanism of activity (FIG. 27C). Utilization of histological analysis, an advantage of a 3D bioprinted intestinal tissue model, confirmed increased disruption of the epithelial layer and decreased expression of E-Cadherin correlated with increasing indomethacin dosing and consistent with loss in barrier function (FIG. 27D).

Figure 28A:
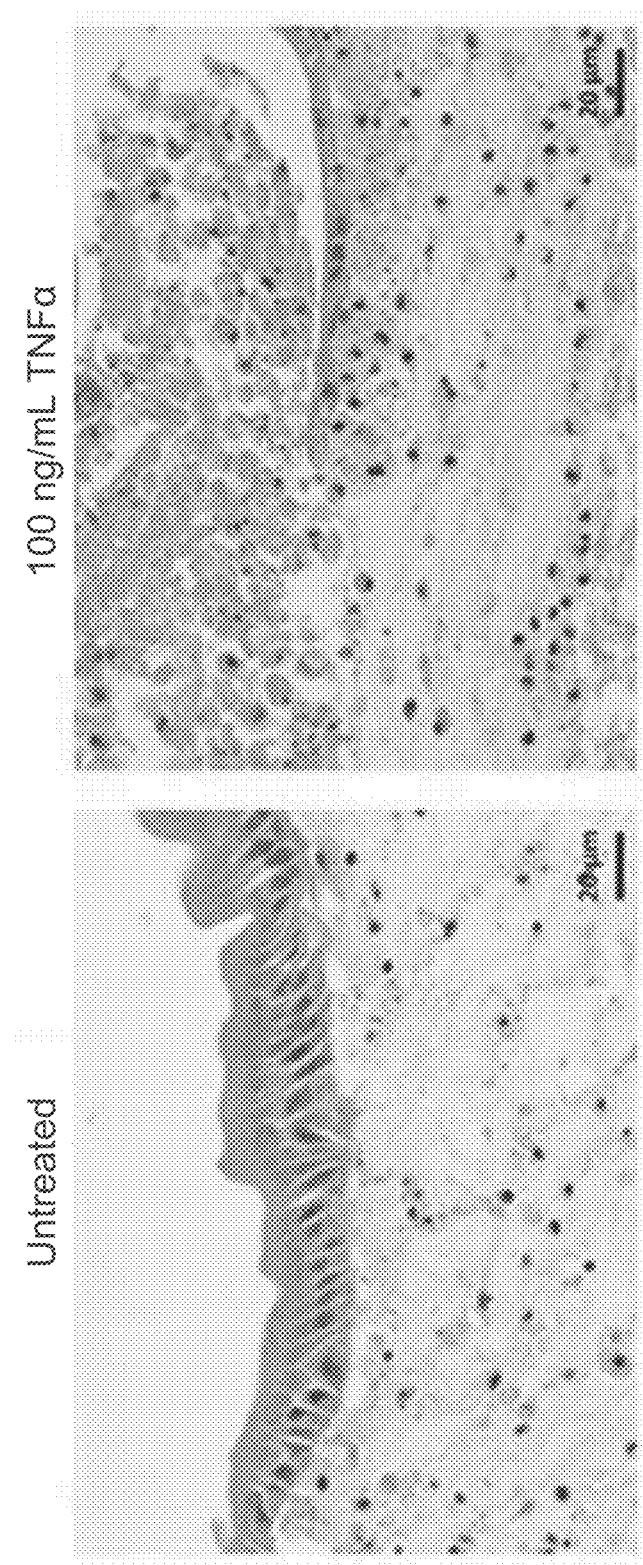
FIGS. 28A-28C show TNFα induced toxicity in 3D bioprinted intestinal tissue.
Figure 28C:
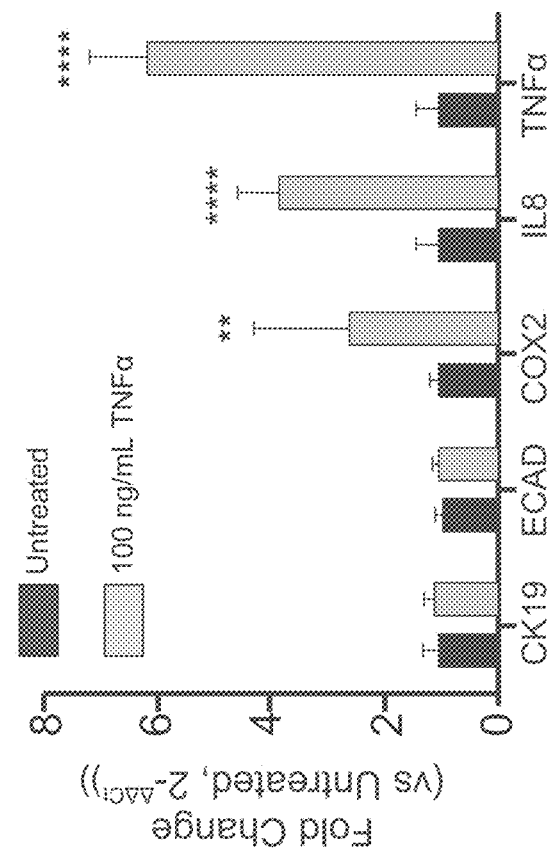
Figure 28B:
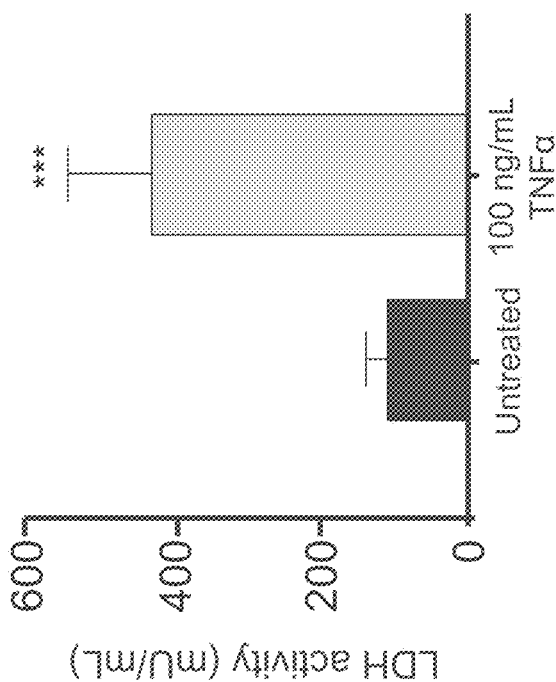

To characterize the 3D bioprinted intestinal model response to inflammation, commonly associated with GI toxicity as well as chronic disease conditions, tissues were treated with a high dose of pro-inflammatory cytokine TNFα for 24 hours and evaluated for changes in morphology, LDH release, and gene expression (FIG. 28). Treatment with TNFα altered epithelial morphology and resulted in dissociation of cells from the interstitial layer. This was accompanied by a significant increase in LDH release from 3D bioprinted intestinal tissue, suggesting a cytotoxic response and enterocyte death. Gene expression for COX-2. IL-8, and TNFα was also upregulated, demonstrating activation of inflammatory pathways. The data collectively demonstrate that 3D bioprinted intestinal tissues can be used to detect and quantify histologic and biochemical aspects of GI toxicity in vitro, including barrier disruption and inflammation.

Advantages of 3D Bioprinted Intestinal Tissue Model

Current preclinical models are limited in their ability to capture the complexities and function of human intestinal tissue [1-5]. Cell monolayers lack native context of cell-cell and cell-matrix interactions and are phenotypically limited, while genetic disparity of animal models may not provide a high correlation with human outcomes [16]. The fully human bioprinted human 3D intestinal tissue model was engineered using primary human cells and was able to recapitulate multiple facets of intestinal biology and function in order to bridge gaps and address translational challenges associated with poor predictability in drug development. The bioprinting platform allows for an automated approach that can reproducibly generate multicellular 3D bioprinted tissues through spatially controlled cellular deposition to better mimic native tissue structure and function compared to traditional 2D models [18, 19]. The 3D complexity allows for both interrogation of the tissues via standard biochemical approaches as well as histological endpoints. The 3D bioprinted intestinal tissue is a highly cellular structure with laminar architecture to allow for access to apical and basal compartments.

The 3D microenvironment promotes crosstalk between primary human myofibroblasts and primary human epithelial cells to support the development and maintenance of a polarized epithelium over a 17 day culture period. Histological analysis confirmed correct polarization of the epithelium with columnar epithelial morphology, tight junctions, and apical brush border formation. Histology and gene expression analyses also demonstrated the presence of specialized cell subpopulations and evidence of mucus production in 3D bioprinted intestinal tissues that was notably absent in standard Caco-2 monolayers. The identification of Mucin-2 positive goblet cells and mucin staining together with the presence of Paneth cells suggests that these tissues could be used to characterize additional aspects of intestinal biology including mucosal barrier function and antimicrobial or microbiome function. While mucin-2 gene expression is decreased compared to native intestine, this may be due in part to differences in temporal regulation at the transcriptional level or a phenotype that can be modulated by altering culture conditions [11]. Chromogranin positive cells suggest that 3D intestinal tissues could also be used to study enteroendocrine function in the gut including GLP-1 signaling. This data indicates that stem cell populations within the isolate can differentiate within 3D intestinal tissues as they mature in culture akin to the composition achieved through organoid cell culture [9, 10, 21], and may be able to undergo directed differentiation by modification of culture conditions [11]. Although adult primary cells were utilized to fabricate tissues in this study, iPSCs can also be considered as a potential alternative cell source to facilitate achieving a more specialized phenotype. The maturity, however, of iPS derived intestinal epithelial cells more closely resembles a fetal stage phenotype [14].

An advantage of the laminar architecture of the 3D bioprinted tissue over organoid systems is compatibility with barrier function and directional transport assessments using standard methodologies. Although organoid researchers have utilized approaches to expose the organoid lumen, efforts require a complex bioreactor set-up [22] and can result in monolayers with non-physiological TEER [23, 24]. Physiological barrier function by TEER was successfully demonstrated in 3D intestinal tissues by day 10 that was maintained through a 21 day culture period. The 3D intestinal tissues have TEER values consistent with reported monolayer cultures of adult intestinal epithelial cells [25], however primary human intestinal epithelial monolayers can suffer from low CYP expression compared to native intestine [26]. This may be due in part to the absence of other relevant cell types like intestinal myofibroblasts to support the epithelium and sustain function. The 3D bioprinted intestinal tissues maintain barrier function for over two weeks in culture. Furthermore, tissues could successfully differentiate between low and high permeability substrates such as paracellular marker Lucifer yellow and transcellular marker propranolol. Functionality over an extended time in culture and the ability to distinguish between compounds can enable both acute and chronic studies with clinically relevant endpoints. Caco-2 monolayer protocols, which require a three week maturation period, exhibited artificially high TEER values, which may be due in part to observed elevated E-Cadherin expression [20]. With the advantage of physiological TEER values, models with human intestinal epithelial cells may yield a better correlation with in vivo permeability than Caco-2 monolayers [25].

Intestinal efflux and influx transporters are key mediators of absorption. Gene expression analysis and immunohistochemistry confirmed the presence of intestinal transporters in the 3D bioprinted intestinal tissues and demonstrated expression levels similar to that of native donor tissue. Clinically relevant P-gp and BCRP, efflux transporters which can significantly affect the net fraction of compound absorbed 12, 61, were correctly expressed in the apical epithelium and functional in response to known substrates digoxin and topotecan, respectively. Expression of functional transporters suggests that this system could be applied to assess the relative contributions of efflux transporters to drug disposition, or used as a potential model for increased absorption by targeting uptake transporters such as PEPT1 and OATP2B1.

A broad gene panel was used to compare expression of 3D bioprinted intestinal tissues to native intestine and Caco-2 cells. The 3D bioprinted intestinal tissue closely matched enzyme and transporter expression of native intestine while Caco-2 monolayers were more divergent, consistent with previous reports [7, 26]. This divergence may be due in part to the cancer origin of Caco-2 cells or the tissue area of origin of the groups compared. Expression of key metabolic enzymes and transporters is known to vary depending on the location in the gastrointestinal tract [2, 27]. Both native intestinal tissue and the 3D bioprinted intestinal model were derived from the ileum whereas Caco-2 cells are derived from the colon. The 3D bioprinted intestinal tissue demonstrated expression of genes including key xenobiotic nuclear receptors VDR, PXR (NR1I2), and CAR (NR1I3) as well as expression of cytochrome P450 and phase II enzymes required for metabolism in the intestine. Activity assays for CYP2C9 and CYP3A4 confirmed that the enzymes were functional. The 3D bioprinted intestinal tissue responded to rifampicin treatment with both increased gene expression and activity of CYP3A4, consistent with PXR activation. It is important to note that both CYP3A4 and PXR are not functional or absent in Caco-2 monolayers [8]. Furthermore, the robustness of the 3D model was demonstrated by midazolam metabolism in tissues fabricated from multiple donors. Donor comparison showed interindividual variation as expected [27] with values similar to those shown for intestinal slices [28] and much higher than those reported for 2D systems [8, 26]. These data suggest suitability of this model for drug induced metabolic and transporter studies that cannot be achieved by previous adult, fetal, or Caco-2 monolayers [8, 26]. The dual presence of transporters and enzymes in the 3D bioprinted intestinal tissue model suggests that it could be used to shed light on complex interactions, such as those seen with overlapping P-gp/CYP3A4 substrates [29].

Gastrointestinal toxicity is a common clinical adverse event in drug development often associated with a high prevalence of diarrhea, an outcome that cannot be accurately predicted or characterized with current in vitro models or in vivo models [4, 5, 30]. NSAID indomethacin was used to successfully validate a toxicity response of the 3D bioprinted intestinal tissue. Tissues responded in a dose-dependent manner with decreased TEER and increased cell disruption, correlating with a decrease in barrier function similar to that reported in in vitro [31] and in vivo outcomes [4]. The 3D bioprinted intestinal tissue also responded to the toxic inflammatory stimulus TNFα, a clinical target [30], with decreased barrier function and upregulation of inflammatory genes, consistent with previous 2D models [32]. These data suggest that the 3D bioprinted intestinal model may be applied to screen other known classes of compounds, such as chemotherapeutics [5], that have off target toxicity in the intestine and combined with long term viability, indicates that the model is amenable to dosing and recovery studies. Furthermore, upregulation of inflammation markers suggests that future applications could include modeling chronic disease such as inflammatory bowel disease (IBD), Crohn's disease, and colitis [4, 5, 30]. Additional complexity can be achieved by incorporating immune cells and/or using intestinal cells isolated by diseased donors [13, 24].

In summary, disclosed is a novel in vitro 3D bioprinted intestinal tissue model with increased complexity and function compared to standard models. The fully human 3D bioprinted intestinal model recapitulates the intestinal mucosa, with physiological barrier function and expression of key functional transporters and metabolic enzymes. The 3D bioprinted intestinal tissue provides a flexible platform compatible with assays for barrier function, permeability, metabolism, transport, and toxicity.

Additional applications of the 3D bioprinted intestinal tissue model include utilization as a disease model to characterize therapeutic targets for multiple applications including inflammation, infectious disease, and endocrine biology. High expression of enzymes involved in fatty acid metabolism in the 3D bioprinted intestinal tissue indicate a potential application for evaluating compounds targeting these enzymes to combat obesity [33]. Furthermore, the interstitium of the 3D bioprinted intestinal model provides a platform for characterizing fibrogenesis, including injury and regeneration such as wound healing, a disease phenotype that cannot be adequately modeled in 2D. To better mimic the native microenvironment, additional applications can utilize cells from different segments of the GI tract for comparison to the ileum such as the duodenum, colon and rectum and could integrate laminar flow. The 3D bioprinted intestinal model could be specialized by addition of a variety of cellular inputs to add complexity by incorporating, for example, endothelial cells to model vasculature, smooth muscle cells to more accurately model the submucosa and gastrointestinal motility, and immune cells to model disease states. Cancer cells can also be added to model tumor behavior in a 3D environment. Because of the native tissue-like multicellularity and architecture, bioprinted 3D intestinal tissues provide a unique opportunity to study complex multifaceted processes including secretion, transport, cell-cell interactions and pathogenic processes across multiple applications in a controlled system.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention.

All patents, patent applications and publications cited herein are fully incorporated by reference herein.

REFERENCES

1. Alqahtani, S., L. A. Mohamed, and A. Kaddoumi, Experimental models for predicting drug absorption and metabolism. Expert Opin Drug Metab Toxicol, 2013. 9(10): p. 1241-54.
2. Peters, S. A., et al., Predicting Drug Extraction in the Human Gut Wall: Assessing Contributions from Drug Metabolizing Enzymes and Transporter Proteins using Preclinical Models. Clin Pharmacokinet, 2016. 55: p. 673-96.

3. Jones. C. R., et al., Gut Wall Metabolism. Application of Pre-Clinical Models for the Prediction of Human Drug Absorption and First-Pass Elimination. Aaps j, 2016. 18(3): p. 589-604.
4. Boelsterli, U. A., M. R. Redinbo, and K. S. Saitta, Multiple NSAID-Induced Hits Injure the Small Intestine: Underlying Mechanisms and Novel Strategies. Toxicol Sci, 2013. 131(2): p. 654-67.
5. Aprile, G., et al., Treatment-related gastrointestinal toxicities and advanced colorectal or pancreatic cancer; A critical update. World J Gastroenterol, 2015. 21(41); p. 11793-803.
6. Bentz, J., et al., Variability in P-Glycoprotein Inhibitory Potency (IC(50)) Using Various in Vitro Experimental Systems: Implications for Universal Digoxin Drug-Drug Interaction Risk Assessment Decision Criteria. Drug Metab Dispos, 2013. 41(7): p. 1347-66.
7. Prueksaritanont, T., et al., Comparative studies of drug-metabolizing enzymes in dog, monkey, and human small intestines, and in Caco-2 cells. Drug Metab Dispos. 1996. 24(6): p. 634-42.
8. Yamaura, Y., et al., Functional Comparison of Human Colonic Carcinoma Cell Lines and Primary Small Intestinal Epithelial Cells for Investigations of Intestinal Drug Permeability and First-Pass Metabolism. Drug Metab Dispos, 2016. 44(3): p. 329-35.
9. Sato, T., et al., Long-term expansion of epithelial organoids from human colon, adenoma, adenocarcinoma, and Barrett's epithelium. Gastroenterology, 2011. 141(5): p. 1762-72.
10. Yin, X., et al., Niche-independent high-purity cultures of Lgr5+ intestinal stem cells and their progeny. Nat Methods, 2014. 11(1): p. 106-12.
11. Watson, C. L., et al. An in vivo model of human small intestine using pluripotent stem cells. Nat Med, 2014. 20(11): p. 1310-4.
12. Wang, X., et al., Cloning and variation of ground state intestinal stem cells. Nature, 2015. 522(7555): p. 173-8.
13. Fatehullah, A., S. H. Tan, and N. Barker, Organoids as an in vitro model of human development and disease. Nat Cell Biol, 2016. 18(3): p. 246-54.
14. Sinagoga, K. L. and J. M. Wells, Generating human intestinal tissues from pluripotent stem cells to study development and disease. Embo j, 2015. 34(9): p. 1149-63.
15. Li, M., I. A. de Graaf, and G. M. Groothuis, Precision-cut intestinal slices: alternative model for drug transport, metabolism, and toxicology research. Expert Opin Drug Metab Toxicol, 2016. 12(2): p. 175-90.
16. Musther, H., et al., Animal versus human oral drug bioavailability; do they correlate? Eur J Pharm Sci, 2014. 57: p. 280-91.
17. Lahar, N., et al., Intestinal subepithelial myofibroblasts support in vitro and in vivo growth of human small intestinal epithelium. PLoS One, 2011. 6(11): p. e26898.
18. Nguyen, D. G., et al., Bioprinted 3D Primary Liver Tissues Allow Assessment of Organ-Level Response to Clinical Drug Induced Toxicity In Vitro. PLoS One, 2016. 11(7): p. e0158674.
19. King, S. M., et al., 3D Proximal Tubule Tissues Recapitulate Key Aspects of Renal Physiology to Enable Nephrotoxicity Testing. Front Physiol, 2017. 8: p. 123.
20. Srinivasan, B., et al., TEER measurement techniques for in vitro barrier model systems. J Lab Autom, 2015. 20(2): p. 107-26.
21. Spence, J. R., et al., Directed differentiation of human pluripotent stem cells into intestinal tissue in vitro. Nature, 2011. 470(7332): p. 105-9.
22. Schweinlin, M., et al., Development of an Advanced Primary Human In Vitro Model of the Small Intestine. Tissue Eng Part C Methods, 2016. 22(9): p. 873-83.
23. Kauffman, A. L., et al., Alternative functional in vitro models of human intestinal epithelia. Front Pharmacol, 2013. 4.
24. VanDussen, K. L., et al., Development of an enhanced human gastrointestinal epithelial culture system to facilitate patient-based assays. Gut, 2015. 64(6): p. 911-20.
25. Takenaka, T., et al., Application of a Human Intestinal Epithelial Cell Monolayer to the Prediction of Oral Drug Absorption in Humans as a Superior Alternative to the Caco-2 Cell Monolayer. J Pharm Sci, 2016. 105(2): p. 915-24.
26. Takenaka, T., et al., Human small intestinal epithelial cells differentiated from adult intestinal stem cells as a novel system for predicting oral drug absorption in humans. Drug Metab Dispos, 2014. 42(11): p. 1947-54.
27. Paine, M. F., et al. Characterization of interintestinal and intraintestinal variations in human CYP3A-dependent metabolism. J Pharmacol Exp Ther, 1997. 283(3): p. 1552-62.
28. van de Kerkhof. E. G., et al., Innovative methods to study human intestinal drug metabolism in vitro: precision-cut slices compared with using chamber preparations. Drug Metab Dispos, 2006. 34(11); p. 1893-902.
29. Kim, R. B., et al., Interrelationship between substrates and inhibitors of human CYP3A and P-glycoprotein. Pharm Res, 1999. 16(3): p. 408-14.
30. Peyrin-Biroulet, L., Anti-TNF therapy in inflammatory bowel diseases: a huge review. Minerva Gastroenterol Dietol, 2010. 56(2): p. 233-43.
31. Tomisato, W., et al., NSAIDs induce both necrosis and apoptosis in guinea pig gastric mucosal cells in primary culture. Am J Physiol Gastrointest Liver Physiol, 2001. 281(4): p. G1092-100.
32. Cui, W., et al., Tumor necrosis factor alpha increases epithelial barrier permeability by disrupting tight junctions in Caco-2 cells. Braz J Med Biol Res, 2010. 43(4): p. 330-7.
33. Shi, Y. and D. Cheng, Beyond triglyceride synthesis: the dynamic functional roles of MGAT and DGAT enzymes in energy metabolism. Am J Physiol Endocrinol Metab, 2009. 297(1): p. E10-8.

What is claimed is:

1. A method of assessing the ability of a candidate therapeutic agent to reverse or reduce an intestinal disorder or injury, the method comprising:
   a. contacting a bioprinted intestinal tissue model with the candidate therapeutic agent, wherein the intestinal tissue model has a phenotype of an intestinal disorder or injury and comprises:
      i. a layer of intestinal interstitial tissue comprising intestinal myofibroblasts; and
      ii. a layer of intestinal epithelial cells on in contact with the apical surface of the layer of intestinal interstitial tissue;
   b. determining the viability or functionality of the intestinal tissue model; and
   c. assessing the ability of the candidate therapeutic agent to reverse or reduce an intestinal disorder or injury based on the determined viability or functionality of the intestinal tissue model compared to a control intestinal tissue model that has not been contacted with the candidate therapeutic agent.

2. The method of claim 1, wherein at least one of the layer of intestinal interstitial tissue and layer of intestinal epithelial cells further comprises at least one type of immune cell.

3. The method of claim 2, wherein the at least one type of immune cell is a myeloid cell and/or lymphoid cell.

4. The method of claim 3, wherein the myeloid cell and/or lymphoid cell is a monocyte, macrophage, neutrophil, basophil, eosinophil, dendritic cell, megakaryocyte, or a combination thereof.

5. The method of claim 1, wherein the phenotype comprises fibrosis and fibrotic scar formation.

6. The method of claim 1, wherein the intestinal tissue model is a model of Crohn's disease, ulcerative colitis, or inflammatory bowel disease.

7. The method of claim 1, wherein the method further comprises inducing the phenotype of the intestinal disorder or injury by: contacting the intestinal tissue model with a treatment, compound, or infectious agent that gives rise to the phenotype.

8. The method of claim 1, wherein at least one of the layer of intestinal interstitial tissue and layer of intestinal epithelial cells comprises cells from a donor with a disease phenotype.

9. The method of claim 8, wherein the layer of intestinal interstitial tissue comprises intestinal myofibroblasts from a donor with the disease phenotype and/or the layer of intestinal epithelial cells comprises primary epithelial cells from a donor with the disease phenotype.

10. The method of claim 8, wherein the disease phenotype is celiac disease, Crohn's disease, ulcerative colitis, irritable bowel syndrome, hemorrhoids, diverticulitis, inflammatory bowel disease, microscopic colitis, lymophocytic colitis, collagenous colitis, endocrine disorders, metabolic disorders, obesity, diabetes, dyslipidemia, intestinal cancer, or colorectal cancer.

11. The method of claim 1, wherein the intestinal tissue model comprises a tumor, tumor fragment, tumor cell, or immortalized cell.

12. The method of claim 1, wherein the intestinal myofibroblasts are adult primary intestinal myofibroblasts and/or the intestinal epithelial cells are adult primary intestinal epithelial cells.

13. The method of claim 1, wherein the density of the layer of intestinal interstitial tissue is at least about $5 \times 10^6$ cells per milliliter.

14. The method of claim 1, wherein the intestinal tissue model is viable for greater than 14 days in culture.

15. A method of assessing the effect of a potential toxic agent on intestinal function, the method comprising:
   a. contacting a bioprinted intestinal tissue model with the potential toxic agent, wherein the intestinal tissue model comprises:
      i. a layer of intestinal interstitial tissue comprising intestinal myofibroblasts; and
      ii. a layer of intestinal epithelial cells in contact with the apical surface of the layer of intestinal interstitial tissue;
   b. measuring the effect of the potential toxic agent on the viability or functionality of the intestinal tissue model.

16. The method of claim 15, wherein the intestinal tissue model is contacted first with the potential toxic agent and then the potential toxic agent is removed.

17. The method of claim 15, wherein at least one of the layer of intestinal interstitial tissue and layer of intestinal epithelial cells further comprises at least one type of immune cell.

18. A method of predicting the effective dosing concentration and dosing schedule of a candidate therapeutic agent, the method comprising:
   a. contacting a bioprinted intestinal tissue model with varying concentrations or amounts of the candidate therapeutic agent, wherein the intestinal tissue model comprises:
      i. a layer of intestinal interstitial tissue comprising intestinal myofibroblasts; and
      ii. a layer of intestinal epithelial cells in contact with the apical surface of the layer of intestinal interstitial tissue;
   b. measuring the effect of the agent on the viability or functionality of the intestinal tissue model over time; and
   c. measuring the recovery of the intestinal tissue model over time to determine the minimum timing between doses that provide efficacy.

19. The method of claim 18, further comprising:
   d. removing the agent; and
   e. assessing whether the absence of the agent results in improved viability or functionality of the intestinal tissue model.

20. The method of claim 18, wherein at least one of the layer of intestinal interstitial tissue and layer of intestinal epithelial cells further comprises at least one type of immune cell.

21. A method of assessing the ability of a potential toxic agent to induce an intestinal disorder or injury, the method comprising:
   a. contacting a bioprinted intestinal tissue model with the potential toxic agent, wherein the intestinal tissue model comprises:
      i. a layer of intestinal interstitial tissue comprising intestinal myofibroblasts; and
      ii. a layer of intestinal epithelial cells on in contact with the apical surface of the layer of intestinal interstitial tissue;
   b. determining the viability or functionality of the intestinal tissue model; and
   c. assessing the ability of the potential toxic agent to induce an intestinal disorder or injury based on the determined viability or functionality of the intestinal tissue model compared to a control intestinal tissue model that has not been contacted with the potential toxic agent.

22. A method of assessing the ability of a candidate therapeutic agent to reduce or prevent an intestinal disorder or injury, the method comprising:
   a. contacting a bioprinted intestinal tissue model with the candidate therapeutic agent, wherein the intestinal tissue model comprises:
      i. a layer of intestinal interstitial tissue comprising intestinal myofibroblasts; and
      ii. a layer of intestinal epithelial cells on the layer of intestinal interstitial tissue;
   b. contacting the intestinal tissue model with a treatment, compound, or infectious agent that is capable of giving rise to a phenotype of an intestinal disorder or injury in the intestinal tissue model;
   c. determining the viability or functionality of the intestinal tissue model; and d. assessing the ability of the candidate therapeutic agent to reduce or prevent an intestinal disorder or injury based on the determined viability or functionality of the intestinal tissue model compared to a control intestinal tissue model that has not been contacted with the candidate therapeutic agent.

* * * * *

UNITED STATES PATENT AND TRADEMARK OFFICE
CERTIFICATE OF CORRECTION

PATENT NO. : 12,365,877 B2
APPLICATION NO. : 17/695538
DATED : July 22, 2025
INVENTOR(S) : Kelsey Nicole Retting et al.

Page 1 of 1

It is certified that error appears in the above-identified patent and that said Letters Patent is hereby corrected as shown below:

In the Claims

In Column 66, Claim 1, Line 59, delete "cells on in contact" and insert --cells in contact--, therefor.

In Column 68, Claim 21, Line 41, delete "cells on in contact" and insert --cells in contact--, therefor.

Signed and Sealed this
Sixteenth Day of September, 2025

Coke Morgan Stewart
*Acting Director of the United States Patent and Trademark Office*